US009494519B2

(12) United States Patent
Selden et al.

(10) Patent No.: US 9,494,519 B2
(45) Date of Patent: Nov. 15, 2016

(54) METHODS FOR RAPID MULTIPLEXED AMPLIFICATION OF TARGET NUCLEIC ACIDS

(75) Inventors: Richard F. Selden, Lincoln, MA (US); Eugene Tan, Arlington, MA (US); Heung Chuan Lam, Newton, MA (US); Heidi Susanne Giese, Newburyport, MA (US); Gregory John Kellogg, Cambridge, MA (US); John A. Wright, Billerica, MA (US)

(73) Assignee: NetBio, Inc., Waltham, MA (US)

( * ) Notice: Subject to any disclaimer, the term of this patent is extended or adjusted under 35 U.S.C. 154(b) by 0 days.

(21) Appl. No.: 13/040,156

(22) Filed: Mar. 3, 2011

(65) Prior Publication Data
US 2011/0312614 A1 Dec. 22, 2011

Related U.S. Application Data

(62) Division of application No. 12/080,746, filed on Apr. 4, 2008.

(60) Provisional application No. 60/921,802, filed on Apr. 4, 2007, provisional application No. 60/964,502, filed on Aug. 13, 2007, provisional application No. 61/028,073, filed on Feb. 12, 2008.

(51) Int. Cl.
| C12Q 1/68 | (2006.01) |
| C12P 19/34 | (2006.01) |
| G01N 21/64 | (2006.01) |
| B01L 3/00 | (2006.01) |
| G01N 27/447 | (2006.01) |
| B01L 7/00 | (2006.01) |

(52) U.S. Cl.
CPC ..... *G01N 21/6486* (2013.01); *B01L 3/502753* (2013.01); *G01N 21/6452* (2013.01); *G01N 27/44726* (2013.01); *G01N 27/44782* (2013.01); *G01N 27/44791* (2013.01); *B01L 7/52* (2013.01); *B01L 2200/0684* (2013.01); *B01L 2200/10* (2013.01); *B01L 2300/069* (2013.01); *B01L 2300/0816* (2013.01); *B01L 2300/0887* (2013.01); *B01L 2400/0421* (2013.01); *G01N 21/6428* (2013.01); *Y10T 436/2575* (2015.01)

(58) Field of Classification Search
USPC ................................. 435/6.12, 91.2
See application file for complete search history.

(56) References Cited

U.S. PATENT DOCUMENTS

| 4,170,616 A | 10/1979 | Jebens |
| 4,811,218 A | 3/1989 | Hunkapiller et al. |
| 4,832,815 A | 5/1989 | Kambara et al. |
| 4,855,225 A | 8/1989 | Fung et al. |
| 4,865,707 A | 9/1989 | Karger |
| 4,881,812 A | 11/1989 | Ohkubo et al. |
| 4,945,135 A | 7/1990 | Grubbs |
| 5,112,460 A | 5/1992 | Karger |
| 5,126,022 A | 6/1992 | Soane et al. |
| 5,126,629 A | 6/1992 | Chopy |
| 5,164,055 A | 11/1992 | Dubrow |
| 5,171,534 A | 12/1992 | Smith et al. |
| 5,198,511 A | 3/1993 | Brown-Wensley |
| 5,234,809 A | 8/1993 | Boom et al. |
| 5,273,638 A | 12/1993 | Konrad et al. |
| 5,281,516 A | 1/1994 | Stapleton et al. |
| 5,290,418 A | 3/1994 | Menchen et al. |
| 5,307,148 A | 4/1994 | Kambara et al. |
| 5,312,940 A | 5/1994 | Grubbs |
| 5,332,666 A | 7/1994 | Prober et al. |
| 5,334,424 A | 8/1994 | Hani et al. |
| 5,342,909 A | 8/1994 | Grubbs |
| 5,462,995 A | 10/1995 | Hosaka et al. |
| 5,468,365 A | 11/1995 | Menchen et al. |
| 5,561,208 A | 10/1996 | Takahashi et al. |
| 5,582,989 A | 12/1996 | Caskey et al. |
| 5,587,128 A | 12/1996 | Wilding et al. |
| 5,644,162 A | 7/1997 | Beilstein et al. |
| 5,663,129 A | 9/1997 | Emert |
| 5,681,741 A | 10/1997 | Atwood et al. |
| 5,723,294 A | 3/1998 | Glass et al. |
| 5,750,015 A | 5/1998 | Soane et al. |
| 5,770,029 A | 6/1998 | Nelson et al. |
| 5,779,868 A | 7/1998 | Parce et al. |
| 5,786,182 A | 7/1998 | Catanzariti et al. |
| 5,800,996 A | 9/1998 | Lee et al. |

(Continued)

FOREIGN PATENT DOCUMENTS

| EP | 0488769 | 6/1992 |
| EP | 1 026 258 A2 | 8/2000 |

(Continued)

OTHER PUBLICATIONS

Henegariu et al. BioTechniques, 1997, vol. 23(3), p. 504-511.*
Oda et al. Anal. Chem. 1998, vol. 70, p. 4361-4368.*
U.S. Appl. No. 13/044,485.
Invitation to Pay Additional Fees for PCT/2010/001741 mailed Oct. 8, 2010.
International Search Report and Written Opinion for PCT/2010/001741 mailed Dec. 2, 2010.

(Continued)

*Primary Examiner* — Kenneth R. Horlick
*Assistant Examiner* — Joyce Tung
(74) *Attorney, Agent, or Firm* — Proskauer Rose LLP

(57) ABSTRACT

A fast, multiplexed PCR system is described that can rapidly generate amplified nucleic acid products, for example, a full STR profile, from a target nucleic acid. Such systems include, for example, microfluidic biochips and a custom built thermal cycler, which are also described. The resulting STR profiles can satisfy forensic guidelines for signal strength, inter-loci peak height balance, heterozygous peak height ratio, incomplete non-template nucleotide addition, and stutter.

28 Claims, 22 Drawing Sheets

(56) References Cited

U.S. PATENT DOCUMENTS

| | | | |
|---|---|---|---|
| 5,821,058 A | 10/1998 | Smith et al. |
| 5,840,338 A | 11/1998 | Roos |
| 5,843,660 A | 12/1998 | Schumm et al. |
| 5,847,162 A | 12/1998 | Lee et al. |
| 5,858,187 A | 1/1999 | Ramsey et al. |
| 5,858,188 A | 1/1999 | Soane et al. |
| 5,858,195 A | 1/1999 | Ramsey |
| 5,861,256 A | 1/1999 | Glass et al. |
| 5,876,675 A | 3/1999 | Kennedy |
| 5,882,856 A | 3/1999 | Shuber et al. |
| 5,897,842 A | 4/1999 | Dunn et al. |
| 5,925,517 A | 7/1999 | Tyagi et al. |
| 5,976,336 A | 11/1999 | Dubrow |
| 5,989,499 A | 11/1999 | Catanzariti et al. |
| 5,994,056 A | 11/1999 | Higuchi et al. |
| 5,994,064 A * | 11/1999 | Staub et al. ............... 435/6.11 |
| 5,994,066 A | 11/1999 | Bergeron et al. |
| 6,017,434 A | 1/2000 | Simpson et al. |
| 6,017,765 A | 1/2000 | Yamada et al. |
| 6,100,541 A | 8/2000 | Nagle |
| 6,103,476 A | 8/2000 | Tyagi et al. |
| 6,120,667 A | 9/2000 | Hayashizaki et al. |
| 6,143,152 A | 11/2000 | Simpson |
| 6,150,097 A | 11/2000 | Tyagi et al. |
| 6,150,180 A | 11/2000 | Parce |
| 6,153,073 A | 11/2000 | Dubrow et al. |
| 6,156,181 A | 12/2000 | Parce |
| 6,156,512 A | 12/2000 | Schumm et al. |
| 6,167,910 B1 | 1/2001 | Chow |
| 6,180,372 B1 | 1/2001 | Franzen |
| 6,207,031 B1 | 3/2001 | Adourian et al. |
| 6,211,955 B1 | 4/2001 | Basiji et al. |
| 6,221,598 B1 | 4/2001 | Schumm et al. |
| 6,224,732 B1 | 5/2001 | Imasaka et al. |
| 6,225,061 B1 | 5/2001 | Becker et al. |
| 6,225,636 B1 | 5/2001 | Ginestet |
| 6,228,634 B1 | 5/2001 | Blumenfeld et al. |
| 6,235,175 B1 | 5/2001 | Dubrow et al. |
| 6,235,479 B1 | 5/2001 | Rogers et al. |
| 6,251,247 B1 | 6/2001 | Mitsuhashi et al. |
| 6,280,589 B1 | 8/2001 | Manz et al. |
| 6,292,499 B1 | 9/2001 | Pearson et al. |
| 6,302,134 B1 | 10/2001 | Kellogg et al. |
| 6,312,886 B1 | 11/2001 | Lee et al. |
| 6,316,781 B1 | 11/2001 | Nagle |
| 6,321,791 B1 | 11/2001 | Chow |
| 6,329,661 B1 | 12/2001 | Perov |
| RE37,606 E | 3/2002 | Guttman |
| 6,358,387 B1 | 3/2002 | Kopf-Sill |
| 6,361,672 B1 | 3/2002 | Zhu et al. |
| 6,372,142 B1 | 4/2002 | Gjerde et al. |
| 6,391,541 B1 | 5/2002 | Petersen et al. |
| 6,403,367 B1 | 6/2002 | Cheng et al. |
| 6,407,395 B1 | 6/2002 | Perov |
| 6,409,900 B1 | 6/2002 | Parce |
| 6,410,275 B1 | 6/2002 | Kluttz et al. |
| 6,413,766 B2 | 7/2002 | Landers |
| 6,413,782 B1 | 7/2002 | Parce |
| 6,420,143 B1 | 7/2002 | Kopf-Sill et al. |
| 6,428,987 B2 | 8/2002 | Franzen |
| 6,429,007 B1 | 8/2002 | Kluttz et al. |
| 6,431,476 B1 | 8/2002 | Taylor et al. |
| 6,432,290 B1 | 8/2002 | Harrison et al. |
| 6,440,725 B1 | 8/2002 | Pourahmadi et al. |
| 6,444,461 B1 | 9/2002 | Knapp et al. |
| 6,458,537 B1 | 10/2002 | White et al. |
| 6,471,916 B1 | 10/2002 | Noblett |
| 6,472,155 B1 | 10/2002 | McKinney |
| 6,472,156 B1 | 10/2002 | Wittwer et al. |
| 6,479,235 B1 | 11/2002 | Schumm et al. |
| 6,479,299 B1 | 11/2002 | Parce |
| 6,485,625 B1 | 11/2002 | Simpson et al. |
| RE37,941 E | 12/2002 | Guttman |
| 6,494,230 B2 | 12/2002 | Chow |
| 6,498,353 B2 | 12/2002 | Nagle |
| 6,524,830 B2 | 2/2003 | Kopf-Sill |
| 6,531,044 B1 | 3/2003 | Anazawa et al. |
| 6,531,282 B1 | 3/2003 | Dau et al. |
| 6,563,584 B1 | 5/2003 | Yurino et al. |
| 6,586,253 B1 | 7/2003 | Harrison et al. |
| 6,598,545 B2 | 7/2003 | Ryaboy et al. |
| 6,602,472 B1 | 8/2003 | Zimmermann |
| 6,605,472 B1 | 8/2003 | Skinner et al. |
| 6,606,273 B1 | 8/2003 | Guo et al. |
| 6,630,063 B1 | 10/2003 | Li et al. |
| 6,630,680 B2 | 10/2003 | Hakamata et al. |
| 6,633,785 B1 | 10/2003 | Kasahara et al. |
| 6,635,487 B1 | 10/2003 | Lee |
| 6,646,271 B2 | 11/2003 | Yokokawa |
| 6,648,015 B1 | 11/2003 | Chow |
| 6,664,057 B2 | 12/2003 | Albertson et al. |
| 6,664,080 B1 | 12/2003 | Pfeffer |
| 6,664,104 B2 | 12/2003 | Pourahmadi et al. |
| 6,709,869 B2 | 3/2004 | Mian et al. |
| 6,733,645 B1 | 5/2004 | Chow |
| 6,733,648 B2 | 5/2004 | Okano et al. |
| 6,764,512 B2 | 7/2004 | Keller |
| 6,774,616 B2 | 8/2004 | Huhn et al. |
| 6,787,016 B2 | 9/2004 | Tan |
| 6,790,952 B2 | 9/2004 | Groen et al. |
| 6,800,438 B2 | 10/2004 | Noolandi et al. |
| 6,824,024 B2 | 11/2004 | Ingenhoven et al. |
| 6,826,524 B1 | 11/2004 | Kim et al. |
| 6,830,936 B2 | 12/2004 | Anderson et al. |
| 6,849,407 B2 | 2/2005 | Espy et al. |
| 6,857,449 B1 | 2/2005 | Chow |
| 6,864,050 B2 | 3/2005 | Su et al. |
| 6,864,571 B2 | 3/2005 | Arik et al. |
| 6,893,879 B2 | 5/2005 | Petersen et al. |
| 6,893,897 B2 | 5/2005 | Sweterlitsch |
| 6,916,614 B1 | 7/2005 | Takenaka |
| 6,929,730 B2 | 8/2005 | Lee |
| 6,949,376 B2 | 9/2005 | Kluttz et al. |
| 6,952,008 B2 | 10/2005 | Corson |
| 6,958,210 B2 | 10/2005 | Smith et al. |
| 6,960,286 B2 | 11/2005 | Manz et al. |
| 6,987,018 B2 | 1/2006 | Taylor et al. |
| 6,991,713 B2 | 1/2006 | Adourian et al. |
| 7,008,771 B1 | 3/2006 | Schumm et al. |
| 7,029,562 B2 | 4/2006 | Anazawa et al. |
| 7,033,474 B1 | 4/2006 | Dubrow |
| 7,038,775 B2 | 5/2006 | Sakai |
| 7,060,948 B2 | 6/2006 | Cho et al. |
| 7,069,952 B1 | 7/2006 | McReynolds |
| 7,074,598 B2 | 7/2006 | Cockerill, III et al. |
| 7,074,599 B2 | 7/2006 | Uhl et al. |
| 7,141,372 B2 | 11/2006 | Spivack et al. |
| 7,142,738 B2 | 11/2006 | Lee et al. |
| 7,150,299 B2 | 12/2006 | Hertzler et al. |
| 7,199,376 B2 | 4/2007 | Prange et al. |
| 7,205,111 B2 | 4/2007 | Christensen et al. |
| 7,261,859 B2 | 8/2007 | Andersson et al. |
| 7,264,950 B1 | 9/2007 | Lee et al. |
| 7,277,284 B2 | 10/2007 | Lee et al. |
| 7,280,204 B2 | 10/2007 | Robinson et al. |
| 7,288,405 B2 | 10/2007 | Shuler et al. |
| 7,300,199 B2 | 11/2007 | Andersson et al. |
| 7,306,924 B2 | 12/2007 | Gomez et al. |
| 7,307,802 B2 * | 12/2007 | Unger ............... 359/793 |
| 7,312,036 B2 | 12/2007 | Sampath et al. |
| 7,312,611 B1 | 12/2007 | Harrison et al. |
| 7,326,779 B2 | 2/2008 | Nakano et al. |
| 7,332,126 B2 | 2/2008 | Tooke et al. |
| RE42,325 E | 5/2011 | Wittwer et al. |
| 2001/0041332 A1 | 11/2001 | Hillebrand et al. |
| 2001/0046667 A1 | 11/2001 | Cloyd et al. |
| 2002/0001801 A1 * | 1/2002 | Fan et al. ............... 435/6 |
| 2002/0009741 A1 | 1/2002 | Simpson |
| 2002/0037520 A1 | 3/2002 | Nikiforov et al. |
| 2002/0042125 A1 | 4/2002 | Petersen et al. |
| 2002/0042151 A1 | 4/2002 | Chen |
| 2002/0046949 A1 | 4/2002 | Nakamura et al. |
| 2002/0055167 A1 | 5/2002 | Pourahmadi et al. |
| 2002/0056639 A1 | 5/2002 | Lackritz et al. |

(56) References Cited

U.S. PATENT DOCUMENTS

| | | |
|---|---|---|
| 2002/0060156 A1 | 5/2002 | Mathies et al. |
| 2002/0076927 A1 | 6/2002 | Henderson et al. |
| 2002/0146734 A1 | 10/2002 | Ortyn |
| 2002/0155485 A1 | 10/2002 | Kao |
| 2003/0007898 A1 | 1/2003 | Bohm |
| 2003/0008286 A1 | 1/2003 | Zou et al. |
| 2003/0020022 A1 | 1/2003 | Kuwabata et al. |
| 2003/0021016 A1 | 1/2003 | Grier |
| 2003/0058440 A1 | 3/2003 | Scott et al. |
| 2003/0082080 A1 | 5/2003 | Zimmermann |
| 2003/0087300 A1 | 5/2003 | Knapp et al. |
| 2003/0089605 A1 | 5/2003 | Timperman |
| 2003/0118477 A1 | 6/2003 | Liljestrand et al. |
| 2003/0134431 A1 | 7/2003 | Parce |
| 2003/0143575 A1 | 7/2003 | Caria et al. |
| 2003/0146145 A1 | 8/2003 | Krotz et al. |
| 2003/0152927 A1 | 8/2003 | Jakobsen et al. |
| 2003/0155966 A1 | 8/2003 | Harrison et al. |
| 2003/0175782 A1 | 9/2003 | Fukushima et al. |
| 2003/0180724 A1 | 9/2003 | Schumm et al. |
| 2003/0186272 A1 | 10/2003 | Dau et al. |
| 2003/0190608 A1 | 10/2003 | Blackburn |
| 2003/0211631 A1 | 11/2003 | Skinner et al. |
| 2004/0048270 A1 | 3/2004 | Zeltz et al. |
| 2004/0062468 A1 | 4/2004 | Lee |
| 2004/0105932 A1 | 6/2004 | Goldberg et al. |
| 2004/0109793 A1 | 6/2004 | McNeely et al. |
| 2004/0115094 A1 | 6/2004 | Gumbrecht et al. |
| 2004/0126279 A1 | 7/2004 | Renzi et al. |
| 2004/0137504 A1 | 7/2004 | Schumm et al. |
| 2004/0168916 A1 | 9/2004 | Fuchs et al. |
| 2004/0178071 A1 | 9/2004 | Harrison et al. |
| 2004/0197816 A1 | 10/2004 | Empedocles et al. |
| 2004/0209354 A1 | 10/2004 | Mathies et al. |
| 2004/0259237 A1* | 12/2004 | Kellogg .............. B01F 13/0064 435/287.1 |
| 2005/0019902 A1 | 1/2005 | Mathies et al. |
| 2005/0053952 A1 | 3/2005 | Hong et al. |
| 2005/0064575 A1 | 3/2005 | Belgrader et al. |
| 2005/0074784 A1 | 4/2005 | Vo-Dinh et al. |
| 2005/0106612 A1 | 5/2005 | Amirkhanian et al. |
| 2005/0109621 A1 | 5/2005 | Hauser et al. |
| 2005/0129582 A1 | 6/2005 | Breidford et al. |
| 2005/0135655 A1 | 6/2005 | Kopf-Sill et al. |
| 2005/0158725 A1* | 7/2005 | Yukimasa et al. ................ 435/6 |
| 2005/0179901 A1 | 8/2005 | Ostlin |
| 2005/0194316 A1 | 9/2005 | Pourahmadi et al. |
| 2005/0287572 A1 | 12/2005 | Mathies et al. |
| 2006/0009106 A1 | 1/2006 | Nishimura et al. |
| 2006/0030796 A1 | 2/2006 | Xu et al. |
| 2006/0035231 A1 | 2/2006 | Van Beuningen et al. |
| 2006/0057629 A1 | 3/2006 | Kim et al. |
| 2006/0068431 A1 | 3/2006 | Lee et al. |
| 2006/0105354 A1 | 5/2006 | Remacle et al. |
| 2006/0134616 A1 | 6/2006 | Belgrader et al. |
| 2006/0141446 A1 | 6/2006 | Murphy et al. |
| 2006/0166223 A1 | 7/2006 | Reed et al. |
| 2006/0213964 A1 | 9/2006 | Excoffier et al. |
| 2006/0216737 A1* | 9/2006 | Bodeau et al. .................... 435/6 |
| 2006/0246501 A1 | 11/2006 | Northrup |
| 2006/0246580 A1 | 11/2006 | Kim et al. |
| 2006/0257958 A1 | 11/2006 | Bruno |
| 2006/0260941 A1 | 11/2006 | Tan et al. |
| 2006/0286552 A1 | 12/2006 | Goldsmith |
| 2007/0116607 A1 | 5/2007 | Wang et al. |
| 2007/0154355 A1 | 7/2007 | Berndt et al. |
| 2007/0154881 A1 | 7/2007 | Koo |
| 2007/0154895 A1 | 7/2007 | Spaid et al. |
| 2007/0184547 A1 | 8/2007 | Handique et al. |
| 2007/0206187 A1 | 9/2007 | Lundquist et al. |
| 2007/0224605 A1 | 9/2007 | An et al. |
| 2008/0003588 A1 | 1/2008 | Hasson et al. |
| 2008/0085521 A1 | 4/2008 | Knapp et al. |
| 2009/0020427 A1 | 1/2009 | Tan et al. |
| 2009/0023603 A1 | 1/2009 | Selden et al. |
| 2009/0059222 A1 | 3/2009 | Tan et al. |
| 2009/0087857 A1 | 4/2009 | Carell et al. |
| 2009/0229983 A1 | 9/2009 | Tan et al. |
| 2010/0285578 A1 | 11/2010 | Selden et al. |
| 2011/0312614 A1 | 12/2011 | Selden et al. |

FOREIGN PATENT DOCUMENTS

| | | |
|---|---|---|
| EP | 1 614 466 A2 | 1/2006 |
| EP | 1 710 017 A1 | 10/2006 |
| JP | 2003-180350 | 12/2001 |
| JP | 2005117988 | 5/2005 |
| WO | WO 89/09437 A1 | 10/1989 |
| WO | WO 99/19717 A1 | 4/1999 |
| WO | WO 99/39005 A1 | 8/1999 |
| WO | WO 01/41931 A2 | 6/2001 |
| WO | WO 01/88204 A1 | 11/2001 |
| WO | WO 01/92575 A1 | 12/2001 |
| WO | WO 02/24322 A2 | 3/2002 |
| WO | WO 02/35223 A1 | 5/2002 |
| WO | WO 02/056004 A2 | 7/2002 |
| WO | WO 02/063288 A1 | 8/2002 |
| WO | WO 02/097398 A2 | 12/2002 |
| WO | WO 2004/052527 A1 | 6/2004 |
| WO | WO 2005/029062 A2 | 3/2005 |
| WO | WO 2005/073691 A1 | 8/2005 |
| WO | WO 2006/032044 A2 | 3/2006 |
| WO | WO 2006/116362 A2 | 11/2006 |
| WO | WO 2006/124842 A2 | 11/2006 |
| WO | WO 2006/128321 A1 | 12/2006 |
| WO | WO 2007/021814 A2 | 2/2007 |
| WO | WO 2008/124104 A1 | 10/2008 |
| WO | WO 2008/124116 A1 | 10/2008 |
| WO | WO 2009/049268 A1 | 4/2009 |
| WO | WO 2009/108260 A2 | 9/2009 |
| WO | WO 2010/147654 A2 | 12/2010 |
| WO | WO 2011/112746 A2 | 9/2011 |

OTHER PUBLICATIONS

[No Author Listed] Micronics licenses "molecular beacons" from UMDNJ's PHRI properties. http://www.technologytransfertactics.com/content/2009/06/10/micronics-licenses-molecular-beacons-from-umdnjs-phri-properties/. 2009.

Albarghourhi et al., Polymeric matrices for DNA sequencing by capillary electrophoresis. Electrophoresis. 2000;21;4096-4111.

Ali et al., DNA hybridization and discrimination of single-nucleotide mismatches using chip-based microbead arrays. Anal Chem. 2003;75(18);4732-9.

Alonso et al., Real-time PCR designs to estimate nuclear and mitochondrial DNA copy number in forensic and ancient DNA studies. Forensic Sci Int. 2004;139(2-3):141-9.

Auroux et al., Micro total analysis systems. 2. Analytical standard operations and applications. Anal Chem. 2002;74:2637-2652.

Becker et al., Polymer microfabrication methods for microfluidic analytical applications. Electrophoresis. 2000;21 : 12-26.

Becker et al., Polymer microfabrication technologies for microfluidic systems. Anal and Bioanal Chem. 2008;390(1):89.

Beckman et al., Survey of human and rat microsatellites. Genomics. 1992;12:627-631.

Bhattacharyya et al., Thermoplastic microfluidic device for on-chip purification of nucleic acids for disposable diagnostics. Anal Chem. Feb. 1. 2006;78(3):788-92.

Blazej et al., Microfabricated bioprocessor for integrated nanoliter-scale Sanger DNA sequencing. Proc Natl Acad Sci U S A. May 9, 2006;103(19):7240-5. Epub Apr. 28, 2006.

Bosserhoff et al., Use of capillary electrophoresis for high throughput screening in biomedical applications, a minireview. Combinational Chemistry and High Throughput Screening. 2000;3:455-66.

Botstein et al., Construction of a genetic linkage map in man using restriction fragment length polymorphisms. Am J Hum Genet. May 1980;32(3):314-31.

Budowle et al., CODIS and PCR based short tandem repeat loci: law enforcement tools. Second European Symposium on Human Identification. 1998:73-88.

(56) References Cited

OTHER PUBLICATIONS

Budowle et al., Using a CCD camera imaging system as a recording device to quantify human DNA by slot blot hybridization. Biotechniques. 2001;30(3):680-5.
Burns et al., An integrated nanoliter DNA analysis device. Science. 1998;282:484-487.
Chen et al., Thermally-actuated, phase change flow control for microfluidic systems. Lab on a Chip. 2005;5:1277-1285.
Chiou et al., A closed-cycle capillary polymerase chain reaction machine. Anal Chem. 2001;73:2018-2021.
Clayton, Go with the microflow. Nature Materials. 2005;2(8):621-626.
Dittrich et al., Micro total analysis systems. Latest advancements and trends. Anal Chem. 2006;78:3887-3907.
Duewer et al., NIST mixed stain studies #1 and #2: interlaboratory comparison of DNA quantification practice and short tandem repeat multiplex performance with multiple-source samples. J Forensic Sci. 2001;46(5):1199-210.
Easley et al., A fully integrated microfluidic genetic analysis system with sample-in-answer-out capability. PNAS. 2006;;103(51):19272-7.
Edwards et al., Automated DNA sequencing methods for detection and analysis of mutations: applications to the Lesch-Nyhan syndrome. Trans Assoc Am Physicians. 1989;102:185-194.
Edwards et al., DNA typing and genetic mapping with trimeric and tetrameric tandem repeats. Am J Hum Genet. 1991;49(4):746-756.
Espy et al., Real-time PCR in clinical microbiology: applications for routine laboratory testing. Clin Microbiol Rev. 2006;19:165-256.
Ewing et al., Base-calling of automated sequencer traces using Phred I. Accuracy Assessment. Genome Res. 1998;8:175-185.
Ewing et al., Base-calling of automated sequencer traces using Phred II. Error Probabilities. Genome Res. 1998;8:186-194.
Ferrance et al., Exploiting sensitive laser-induced fluorescence detection on electrophoretic microchips for executing rapid clinical diagnostics. Luminscence. 2001;16:79-88.
Fiorini et al., Disposable microfluidic devices: fabrication, function, and application. BioTechniques. 2005;38:429-446.
Fox et al., Development, characterization, and validation of a sensitive primate-specific quantification assay for forensic analysis. BioTechniques. 2003: 314-8, 320, 322.
Geiss et al., Direct multiplexed measurement of gene expression with color-coded probe pairs. Nature Biotech. 2008;26(3):317-325.
Gerstner et al., Near-infrared dyes for six-color immunophenotyping by laser scanning cytometry. Cytometry. 2002;48(3):115-123.
Giese et al., Fast multiplexed polymerase chain reaction for conventional and microfluidic short tandem repeat analysis. J Forensic Sci. 2009;54(6):1287-1296.
Gill et al., Application of low copy number DNA profiling. Croat Med J. 2001;42:229-32.
Goedecke et al., A high-performance multilane microdevice system designed for the DNA forensics laboratory. Electrophoresis. 2004;25:1678-1686.
Harrison et al., Capillary electrophoresis and sample injection systems integrated on a planar glass chip. Anal Chem. 1992;64:1926-1932.
Hawkins, Nonlinear decrease of background fluorescence in polymer thin-films—a survery of materials and how they can complicate fluorescence detection in μTAS. Lab Chip. 2003;3(4):24852.
Hayn et al., Evaluation of an automated liquid hybridization method for DNA quantitation. J Forensic Sci. 2004;49(1):87-91.
Heid et al., Real time quantitative PCR. Genome Res. 1996;6:986-994.
Henegariu et al., Multiplex PCR: critical parameters and step-by-step protocol. Biotechniques. 1997;23:504-11.
Hill et al., A 26plex autosomall STR assay to aid human identity testing. J Forensic Sci. 2009;54(5):1008-1015.
Holland et al., Detection of specific polymerase chain reaction product by utilizing the 5'—3' exonuclease activity of Thermus aquaticus DNA polymerase. PNAS. 1991;88(16):7276-80.
Holt et al., TWGDAM validation of AplFISTR PCR amplification kits for forensic DNA casework. 2002. J Forensic Sci. 2002;47(1):66-96.
Hopwood et al., Forensic response vehicle: rapid analysis of evidence at the scene of a crime. International Congress Series. 2006;1288:639-641.
Hopwood et al., Rapid quantification of DNA samples extracted from buccal scrapes prior to DNA profiling. Biotechniques. 1997;23(1):18-20.
Horsman et al., Forensic DNA analysis on microfluidic devices: a review. J Forensic Sci. 2007;52:784-799.
Huang et al., An integrated microfluidic chip for DNA/RNA amplification, electrophoresis separation, and on-line optical detection. Electrophoresis. 2006;27:3297-3305.
Ibrahim et al., Real-time microchip PCR for detecting single-base differences in viral and human DNA. Anal Chem. May 1, 1998;70(9):2013-7.
Janasek et al., Scaling and the design of miniaturized chemical-analysis systems. Nature. 2006;442:374-80.
Kamentsky et al., Slide-based laser scanning cytometry. Acta Cytologica. International Academy of Cytology. Chicago, IL. 1997;41(1):123-143.
Kan et al., DNA sequencing and genotyping in miniaturized electrophoresis systems. Electrophoresis. 2004;25:(21-22):3564-3588.
Kim et al., Rapid DNA hybridization analysis using a PDMS microfluidic sensor and a molecular beacon. Anal Sci. 2007;23:401-405.
Kline et al., NIST Mixed Stain Study 3: DNA quantitation accuracy and its influence on short tandem repeat multiplex signal intensity. Anal Chem. 2003;75(10):2463-9.
Krasnoperov et al., Luminescent Probes for Ultrasensitive Detection of Nucleic Acids. Bioconjug. Chem. 2010;21:319-327.
Krenke et al., Validation of a 16-locus fluorescent multiplex system. J Forensic Sci. 2002;47(4):773-85.
Lafountain et al., TWGDAM validation of the AmpFISTR profiler plus and AmpFISTR COFiler STR multiplex systems using capillary electrophoresis. J Forensic Sci. 2001;46(5):1191-8.
LeClair et al., Systemic analysis of stutter percentages and allele peak height and peak area ratios at heterozygous STR loci to forensic casework and database samples. J Forensic Sci. 2004;49:968-80.
Li et al., An estimate of the crosstalk matrix in four-dye fluroescence-based DNA sequencing. Electrophoresis. 1999;20(1):1433-1442.
Liu et al., Automated parallel DNA sequencing on multiple channel microchips. PNAS. 2000;97(10):5369-5374.
Liu et al., DNA amplification and hybridization assays in integrated plastic monolithix devices. Anal Chem. 2002;74:3063-3070.
Liu et al., Integrated microfluidic systems for high-performance genetic analysis. Trends Biotechnol. Oct. 2009;27(10):572-81. Epub Aug. 24, 2009.
Liu et al., Integrated portable polymerase chain reaction-capillary electrophoresis microsystem for rapid forensic short tandem repeat typing. Anal Chem. 2007;79:1881-9.
Liu et al., Self-contained, fully integrated biochip for sample preparation, polymerase chain reaction amplification, and DNA microarray detection. Anal Chem. Apr. 1, 2004;76(7):1824-31.
Mandrekar et al., Development of a human DNA quantitation system. Croat Med J. 2001;42(3):336-9.
Maxam et al. A new method for sequencing DNA. PNAS. 1977;74:560-564.
McCormick et al., Microchannel electrophoretic separations of DNA in injeection-molded plastic substrates. Anal Chem. 1997;69(14):2626-2630.
Metzker et al., Emerging technologies in DNA sequencing. Genome Res. 2005;15:1767-1776.
Milligan et al., Current concepts in antisense drug design. J Med Chem. 1993;36:1923-1937.
Mitnik et al., High-speed analysis of multiplexed short tandem repeats with an electrophoretic microdevice. Electrophoresis. 2002;23:719-26.

(56) References Cited

OTHER PUBLICATIONS

Mittag et al., Polychromatic (eight-color) slide-based cytometry for the phenotyping of leukocyte, NK, and NKT subsets. Cytometry. 2005-06;65A(2):103-115.
Moretti et al., Validation of short tandem repeats (STRs) for forensic usage: performance testing of fluorescent multiplex STR systems and analysis of authentic and simulated forensic samples. J Forensic Sci. 2001;46(3):647-60.
Nazarenko et al., A closed tube format for amplification and detection of DNA based on energy transfer. Nucleic Acids Res. 1997;25(12):2516-21.
Nicklas et al., Development of an Alu-based, QSY 7-labeled primer PCR method for quantitation of human DNA in forensic samples. J Forensic Sci. 2003;48(2):282-91.
Nicklas et al., Development of an Alu-based, real-time PCR method for quantitation of human DNA in forensic samples. J Forensic Sci. 2003;48(5):936-44.
Nicklas et al., Quantification of DNA in forensic samples. Anal Bioanal Chem. 2003;376(8):1160-7.
Paegel et al., High throughput DNA sequencing with a microfabricated 96-lane capillary array electrophoresis bioprocessor. 2002. PNAS. 99(2):574-579.
Pal et al., An integrated microfluidic device for influenza and other genetic analyses. Lab Chip. 2005;5:1024-1032.
Pursika et al. The autofluorescence of plastic materials and chips measured under laser irradiation. Lab Chip. 2005;5(12):1348-1354.
Read et al., Rapid multi-locus sequence typing using microfluidic biochip. PLoS ONE. 2010: e10595.
Reyes et al., Micro total analysis systems. 1. Introduction, theory, and technology. Anal Chem. 2002;74:2623-2636.
Ruiz-Martinez et al., DNA sequencing by capillary electrophoresis with replaceable linear polyacrylamide and laser-induced fluorescence detection. Anal Chem. 1993;65:2851-58.
Rye et al., Fluorometric assay using dimeric dyes for double- and single-stranded DNA and RNA with picogram sensitivity. Anal Biochem. 1993;208(1):144-50.
Sanger et al., DNA sequencing with chain-terminating inhibitors. PNAS. 1977;74:5463-5467.
Sassi et al., Rapid, parallel separations of D1S80 alleles in a plastic microchannel chip. J Chromatogr A. 2000;894(1-2):203-213.
Schmidt et al., Low-volume amplification on chemically structured chips using the powerplex 16 DNA amplification kit. Int J Legal Med. 2006;120:42-48.
Scientific Working Group on DNA Analysis Methods, Short Tandem Repeat (STR) Interpretation Guidelines. Forensic Science Communications. 2000;2(3)>.
Shewale et al., Human genomic DNA quantitation system, H-Quant: development and validation for use in forensic casework. J Forensic Sci. 2007;52(2):364-70.
Shi et al., High-resolution single stranded DNA analysis on 4.5 cm plastic electrophoretic microchannels. Electrophoresis. 2003;24(19-20):3371-3377.
Shi, DNA sequencing and multiplex STR analysis on plastic microfluidic devices. Electrophoresis. 2006;27(10):3703-3711.
Shrinivasan et al., A low-cost, low-power consumption, miniature laser-induced fluorescence system for DNA detection on a microfluidic device. Clin Lab Med. 2007;27:173-181.
Sifis et al., A more sensitive method for the quantitation of genomic DNA by Alu amplification. J Forensic Sci. 2002; 47(3):589-92.
Simpson et al., High-throughput genetic analysis using microfabricated 96-sample capillary array electrophoresis microplates. PNAS. 1998;95:2256-2261.
Singer et al., Characterization of PicoGreen reagent and development of a fluorescence-based solution assay for double-stranded DNA quantitation. Anal Biochem. 1997; 249(2):228-38.
Situma et al., Immobilized molecular beacons: a new strategy using UV-activated poly(methyl methacrylate) surface to provide large fluorescence sensitivities for reporting on molecular association events. Anal Biochem. 2007;363:35-45.
Skelley et al., Development and evaluation of a microdevice for amino acid biomarker detection and analysis on Mars. PNAS. 2005;102(4):1041-1046.
Strauss-Soukup et al., Effects of neutralization pattern and stereochemistry on DNA bending by methylphosphonate substitutions. Biochem. 1997;36:8692-8698.
Summit et al., Pressure enhances thermal stability of DNA polymerase from three thermophilic organisms. Extremeophiles. 1998;2:339-345.
Swango et al., A quantitative PCR assay for the assessment of DNA degradation in forensic samples. Forensic Sci Int. 2006;158(1):14-26.
Swango et al., Developmental validation of a multiplex qPCR assay for assessing the quantity and quality of nuclear DNA in forensic samples. Forensic Sci Int. 2007;170(1):35-45.
Takahashi et al., Evaluation of the NanoChip 400 system for detection of influenza A and B, respiratory synctial and parainfluenza viruses. J Clin Microbiol. May 2008;46(5):1724-7.
Tanious et al., DAPI (4',6-diamidino-2-phenylindole) binds differently to DNA and RNA: minor-groove binding at AT sites and intercalation at AU sites. Biochemistry.1992;31(12):3103-12.
Tomsey et al., Comparison of PowerPlex 16, PowerPlex1.1/2.1, and ABI AmpfISTR Profiler Plus/COfiler for forensic use. Croat Med J. 2001;42(3):239-43.
Tsao et al., Bonding of thermoplastic polymer microfluidics. Microfluid Nanofluid. 2009;6:1-16.
Vallone et al., Uses of the NIST 26plex STR assay for human identity testing. Forensic Science International: Genetics Supplement. 2009;2:29-30.
Van Dyke et al., Automated systems for the fluorometric determination of nucleic acids by the ethidium bromide technique. Anal Biochem. 1968;23(1):109-16.
Verheggen et al., Simple sampling device for capillary isotachophoresis and capillary zone electrophoresis. Journal of Chromatography. 1988;452:615-622.
Wabuyele et al., Single molecule detection of double-stranded DNA in poly(methylmethacrylate) and polycarbonate microfluidic devices. Electrophoresis. 2001;22(18):3939-40.
Walsh et al., A rapid chemiluminescent method for quantitation of human DNA. Nucleic Acids Res.1992;20(19):5061-5.
Walsh et al., Amplification of alleles: mechanisms and solutions. PCR Methods Appl. 1992;1:241-250.
Walsh et al., Sequence analysis and characterization of stutter products at the tetranucleotide repeat locus of vWA. Nucleic Acids Res. 1996;24(14):2807-12.
Wang et al., A disposable microfluidic cassette for DNA amplification and detection. Lab on a Chip. 2006;6:46-53.
Wang et al., Self-actuated, thermo-responsive hydrogel valves for lab on a chip. Biomed Microdevices. 2005;7(4):313-322.
Whitcombe et al., Detection of PCR products using self-probing amplicons and fluorescence. Nat Biotechnol. 1999; 17(8):804-7.
Wittwer et al., Continuous fluorescence monitoring of rapid cycle DNA amplification. Biotechniques. 1997;22(1):130-1, 134-8.
Woolley et al., High-speed DNA genotyping using microfabricated capillary array electrophoresis chips. Anal Chem. 1997;69(11):2181-2186.
Woolley et al., Ultra-high-speed DNA sequencing using capillary electrophoresis chips. Anal Chem. 1995;67(20):3676-3680.
Yeung et al., Rapid and high-throughput forensic short tandem repeat typing using a 96-lane microfabricated capillary array electrophoresis microdevice. J Forensic Sci. Jul. 2006;51(4):740-7.
Yuen et al., Microchip module for blood sample preparation and nucleic acid amplification reactions. Genome Res. 2001;11:405-12.
Zhang et al., Miniaturized PCR chips for nucleic acid amplification and analysis: latest advances and future trends. Nuclei Acids Research. 2007;1-15.

\* cited by examiner

METHODS FOR RAPID MULTIPLEXED AMPLIFICATION OF TARGET NUCLEIC ACIDS

CROSS-REFERENCE TO RELATED APPLICATIONS

This application is a divisional of U.S. patent application Ser. No. 12/080,746 filed 4 Apr. 2008, which claims the benefit of the filing date, under 35 U.S.C. §119(e), of U.S. Provisional Application Ser. No. 60/921,802 filed 4 Apr. 2007; U.S. Provisional Application Ser. No. 60/964,502 filed 13 Aug. 2007; and U.S. Provisional Application Ser. No. 61/028,073 filed 12 Feb. 2008, each of that is hereby incorporated by reference in its entirety. This application also incorporates by reference, in their entireties, two U.S. patent applications filed 4 Apr. 2008; the first entitled "INTEGRATED NUCLEIC ACID ANALYSIS", U.S. patent application Ser. No. 12/080,751, now published as US 2009/0059222; and the second entitled "PLASTIC MICROFLUIDIC SEPARATION AND DETECTION PLATFORMS", U.S. patent application Ser. No. 12/080,745, now published as US 2009/0020427.

FIELD OF THE INVENTION

The present invention generally relates to methods for the rapid amplification of one or more loci within a nucleic acid sample, as well as thermal cyclers and systems useful for performing the methods.

BACKGROUND OF THE INVENTION

The polymerase chain reaction (PCR) is an enzymatic reaction that facilitates rapid exponential amplification of nucleic acid sequences in vitro. In forensics, PCR can be utilized to identify individuals based on the amplification of small regions of the human genome containing a class of repeated DNA known as Short Tandem Repeats (STRs). The unit length of a given STR repeat ranges between 2-10 base pairs, and STRs generally fall within non-coding and flanking sequences but occasionally within coding regions (Edwards et al., *Am. J. Hum. Genet.* 1991, 49, 746-756). There are several hundred thousand STR loci in the human genome, occurring on average every 6-10 kb (Beckman and Weber, Genomics 1992, 12, 627-631) and appearing to be highly polymorphic (Edwards et al., *Trans. Assoc. Am. Physicians* 1989, 102, 185-194). STR analysis has become a major tool in the forensic armamentarium with a growing set of applications including paternity testing, human identification in mass disasters, and routine typing of children.

While several commercially available STR kits have been developed for synthesizing the desired PCR products with high specificity, there are significant areas in which current STR technologies can be improved. Most importantly, the average time to complete multiplex PCR using commercial STR typing kits is approximately 2.14 hours; the time-consuming and labor-intensive nature of these assays has contributed to backlogs in forensic laboratories. While the advent of automated instrumentation to simultaneously process multiple samples has helped to alleviate a significant bottleneck in typing throughput, the increasing number of samples to be analyzed will require further acceleration of the process. Furthermore, there is a need to increase the sensitivity of STR assays as well as to improve the detection of the amplified products (Gill, *Croat. Med. J.* 2001, 42, 229-32). Currently available STR kits contain nine to sixteen loci and work is underway in the field to increase the number of loci that can be detected. Certain applications of STR analysis in the field can be conducted using 4 or more loci.

PCR can also be applied in a wide range of clinical settings. For example, PCR can be utilized to diagnose bacterial infections such as those caused by Group A Streptococci, methicillin resistant *S. aureus*, and vancomycin resistant Enterococci and is generally more sensitive than culture-based diagnostic techniques. Fungal infections can be similarly diagnosed. PCR can be used to diagnose respiratory viruses (e.g., respiratory syncytial virus, adenovirus, and influenza and parainfluenza viruses), genito-urinary viruses (e.g., herpes simplex virus and typing human papilloma viruses), meningitis (e.g., herpes simplex virus, Epstein-Ban virus, varicella-zoster virus, and enteroviruses), and hepatitis (e.g., hepatitis B and C). PCR is also useful in preimplantation genetic diagnosis including the assessment of aneuploidy as well as the diagnosis of inherited diseases. From oncology to rheumatology and from hematology to gastroenterology, it would be difficult to find an area of medicine not impacted by PCR.

PCR has also been applied in a variety of non-clinical settings including veterinary identification (analogous to human STR typing), veterinary diagnostics, assessment of food safety, detection of agricultural pathogens and pharmacogenomics. An application of growing importance concerns the identification of biological weapons agents in clinical and environmental samples. Real-time PCR, a close relative of PCR that allows quantitation of the amount of product present in a reaction following each amplification cycle, is utilized in essentially the same applications as PCR itself (see, Espy et al., *Clinical Microbiology Reviews* 2006, 19, 1656-256).

Most commercially available thermal cycling instruments are limited in that they receive temperature feedback directly from and control the block temperature as opposed to the PCR solution temperature. As a consequence, the temperature profile of the solution, which is critical to the success of the PCR, is likely to be grossly different from the desired profile.

Moreover, much of the literature on increasing PCR speed and sensitivity has focused on amplification of one particular locus at a time ("singleplex assays") and only limited success has been reported in simultaneous amplification of multiple loci ("multiplex assays") as required for forensic STR typing, clinical diagnostic and non-clinical applications. For example, a 160 nL chamber coupled to an integrated heater has been shown to be capable of amplification and separation of 4 STRs contained in a Y-STR assay in 80 minutes with a detection limit of 20 copies of template DNA. (Liu et al., *Anal. Chem.* 2007, 79, 1881-1889). Increased PCR sensitivity due to reduced PCR reaction volume has also been reported for the PowerPlex® 16 System, although no attempt was made to increase reaction speed (Schmidt et al., *Int. J. Legal Med.* 2006, 120, 42-48). However, neither report provided for the significantly shorter amplification times needed in the art. Hopwood et al., (*International Congress Series* 1288 (2006) 639-641) report a one hundred minute amplification using a set of 11 STR primers. With respect to clinical diagnostics, a panel of seven common respiratory viruses was amplified using a nanochip system in a PCR assay requiring 97.5 minutes (Takahashi et al., *J. Clin. Microbiol.* 2008, doi:10.1128/JCM.01947-07).

Many of the applications of PCR (and real time PCR) such as forensic human identification by STR typing, clinical diagnostics, and biological weapons agent detection are extremely time sensitive and many of the applications are best performed in a multiplex setting. In addition, many of these applications are utilized in settings in which limited sample is available (e.g., a small number of pathogens from a clinical or environmental sample or a small number of human cells from a forensic sample) and sensitivity of the reaction is critical.

Notably, Horsman et al., (*J. Forensic Sci.*, 2007, 52, 784-799) Id. at 792 stated that "PCR has been a common pursuit among analytical microchip researchers, as demonstrated by the wealth of literature on the topic. However, for forensic DNA analysis, there remain a number of avenues for development. Extensive work has not been shown using the commercially available forensic STR kits or, further, multiple STR amplifications on a single device. When fully developed, however, microchip PCR will undoubtedly be a considerable time and cost savings to the forensic community." Therefore, there exists a need in the art for rapid and sensitive methods to successfully provide simultaneous amplification of a plurality of loci within a nucleic acid sample for a broad range of applications.

SUMMARY OF THE INVENTION

The instruments, biochips, methods and systems of the invention provide the capability of heating and cooling a PCR solution rapidly, controllably, and reproducibly through monitoring and controlling the thermal cycler based on, at least in part, the actual temperature of the solution. The inventive instruments, biochips, methods and systems disclosed herein provide the ability to monitor and/or accurately control the reaction temperature of a solution within a biochip to avoid over- or under-heating through the specific incorporation of thermosensors that are not present in commercial thermal cyclers. The ability to rapidly heat and cool reaction solutions to such temperatures allows ramping and settling times to be minimized and incubation time at the desired temperature to dominate the total step time. Further, the instruments, biochips, methods and systems of the invention provided herein impart the ability to rapidly alter and equilibrate the temperature of a reaction solution, thereby greatly increasing the speed at which an amplification reaction may proceed.

Fast multiplex PCR amplification times as short as seventeen minutes have been achieved using instruments, biochips, methods and systems of the invention. Additional time reductions are possible based on the teachings of this invention. Further, the fast PCR methods of the invention are effective over a wide dynamic range, are extremely sensitive and are compatible with a wide range of commercially available enzymes and reagents. For forensic applications, the instruments, biochips, methods and systems of the invention enable significant reductions in the time required to generate full profiles that satisfy interpretation guidelines for STR analysis.

In a first aspect, the invention provides thermal cyclers comprising a temperature control element (TCE) wherein a first surface of said TCE is adapted to receive a sample chamber containing a solution and a sensing chamber containing a thermosensor, wherein the thermosensor provides feedback to the TCE to set or maintain the sample at a desired temperature. In a second aspect, the invention provides thermal cyclers further comprising a second thermosensor positioned to monitor the temperature of the first surface of the TCE.

In a second aspect, the invention provides systems comprising a biochip comprising one or a plurality of reaction chambers comprising a portion of the biochip having a volume, wherein each reaction chamber further comprises a microfluidic inlet channel and a microfluidic outlet channel, wherein each reaction chamber is less than 200 µm from a contact surface of the biochip substrate; the system further comprising a thermal cycler, comprising a temperature control element (TCE) wherein a first surface of the TCE is adapted to receive a substrate containing a sample, and a thermosensor positioned to measure the temperature of sample in the substrate and provide feedback to the TCE to set or maintain the sample at a desired temperature said thermal cycler in thermal communication with the contact surface of the biochip substrate.

In a third aspect, the invention provides systems comprising a biochip, comprising one or a plurality of reaction chambers, wherein each reaction chamber comprising a portion of the biochip having a volume, further comprising a microfluidic inlet channel and a microfluidic outlet channel, wherein each reaction chamber is less than 100 µm from a contact surface of the biochip substrate; and a thermal cycler, comprising a temperature control element (TCE) wherein a first surface of the TCE is adapted to receive a substrate containing a sample, and a thermosensor positioned to measure the temperature of sample in the substrate and provide feedback to the TCE to set or maintain the sample at a desired temperature, said thermal cycler in thermal communication with the contact surface of the biochip substrate.

In a fourth aspect, the invention provides methods for simultaneously amplifying of a plurality of loci in a nucleic acid solution comprising providing one or a plurality of reaction chambers wherein each reaction chamber comprises (i) a nucleic acid solution comprising at least one copy of at least one target nucleic acid to be amplified; (ii) one or more buffers; (iii) one or more salts; (iv) a primer set corresponding to each of the plurality of loci to be amplified; (v) a nucleic acid polymerase; and (vi) nucleotides, sequentially thermally cycling the temperature of the nucleic acid solution in each reaction chamber between a denaturing state, an annealing state, and an extension state for a predetermined number of cycles at heating and a cooling rates of about 4-150° C./sec, to yield a plurality of amplified loci in each reaction chamber in about 97 minutes or less.

In a fifth aspect, the invention provides methods for simultaneously amplifying of a plurality of loci in a nucleic acid solution comprising providing one or a plurality of reaction chambers wherein each reaction chamber comprises (i) a nucleic acid solution comprising at least one copy of at least one target nucleic acid to be amplified; (ii) one or more buffers; (iii) one or more salts; (iv) a primer set corresponding to each of the plurality of loci to be amplified; (v) a nucleic acid polymerase; and (vi) nucleotides, sequentially thermally cycling the temperature of the nucleic acid solution in each reaction chamber for a predetermined number of cycles at heating and a cooling rates of about 4-150° C./sec, to yield a plurality of amplified loci in each reaction chamber in about 97 minutes or less.

In a sixth aspect, the invention provides methods for simultaneously amplifying 5 or more loci in a nucleic acid solution comprising providing one or a plurality of reaction chambers wherein each reaction chamber comprises (i) a nucleic acid solution comprising at least one copy of at least one target nucleic acid to be amplified; (ii) one or more buffers; (iii) one or more salts; (iv) a primer set corresponding to the 5 or more loci to be amplified; (v) a nucleic acid polymerase; and (vi) nucleotides, sequentially thermally cycling the temperature of the nucleic acid solution in each reaction chamber between a denaturing state, an annealing state, and an extension state for a predetermined number of cycles at heating and a cooling rates of about 4-150° C./sec, to yield 5 or more amplified loci in each reaction chamber.

In a seventh aspect, the invention provides integrated biochips systems comprising a biochip comprising at least two reaction chambers in microfludic communication, wherein a first reaction chamber is in thermal communication with a thermal cycler, comprising: a temperature control element (TCE) wherein a first surface of the TCE is adapted to receive a substrate containing a sample, and a thermosensor positioned to measure the temperature of sample in the substrate and provide feedback to the TCE to set or maintain the sample at a desired temperature wherein a contact surface of the biochip is in thermal communication with the first surface of the thermal cycler; and a second reaction chamber in fluid connection with the first reaction chamber and adapted for nucleic acid extraction, nucleic acid purification, pre-PCR nucleic acid cleanup, post-PCR cleanup, pre-sequencing cleanup, sequencing, post-sequencing cleanup, nucleic acid separation, nucleic acid detection, reverse transcription, pre-reverse transcription cleanup, post-reverse transcription cleanup, nucleic acid ligation, nucleic acid hybridization, or quantification, wherein the first reaction chamber is less than 200 μm from a contact surface of the biochip.

Specific preferred embodiments of the present invention will become evident from the following more detailed description of certain preferred embodiments and the claims.

DETAILED DESCRIPTION OF THE INVENTION

Figure 1A:
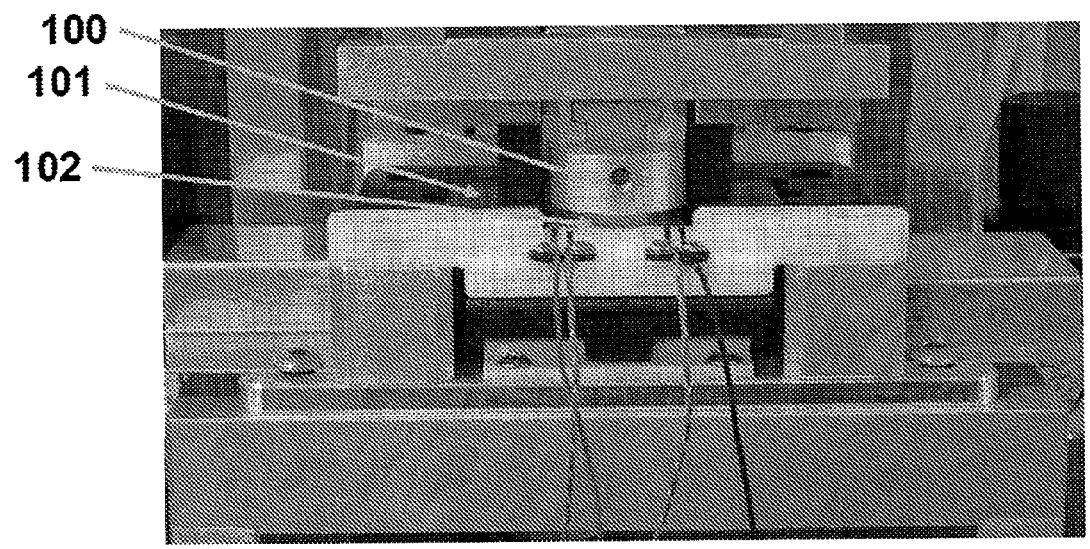
FIG. 1A is a photograph of an embodiment of the thermal cycler of the invention comprising a chip compression element and thermal control element (100), biochip (101) and thermo sensor (102).

In order to achieve fast multiplexed nucleic acid amplification, such as PCR, the invention provides thermal cycling instrumentation, reaction vessels, and reaction conditions that can be used to amplify a plurality of loci within a target nucleic acid sample. As is illustrated by the examples provided herein, fast thermal cycling methods of the invention can be performed in microfluidic biochips using the thermal cycler of the invention and the methods described herein.

The methods provided by the invention are capable of rapid multiplex amplification in applications in addition to those utilizing the biochips and thermal cyclers described herein. For example, the use of thin walled tubes in conventional thermal cyclers (for example block based thermal cyclers and the Roche LightCycler™) and the use of amplification methods other than temperature cycled PCR (for example isothermal PCR or rolling circle amplification) are specifically contemplated.

The methods, biochips, and thermal cyclers provided by the invention are capable of amplifying a plurality of loci in under 100 minutes within a given nucleic acid solution present at amounts of at least 0.006 ng of human genomic DNA (the approximate amount of DNA in a single nucleated human cell) containing the target nucleic acid locus or loci). In other embodiments the amplification occurs in less than 90 min., less than 80 min., less than 70 min., less than 60 min., less than 50 min., less than 40 min., less than 30 min., less than 20 min., less that 17.7 min., less than 15 min., less than 10 min., or less than 5 min.

In other embodiments, a plurality of loci within a bacterial, viral, fungal, animal, or plant-derived genome can be amplified starting from at least one copy of the target nucleic acid locus or loci. For example, a sample to be analyzed can comprise less than 1000 copies, less than 400 copies, less than 200 copies, less than 100 copies, less than 50 copies, less than 30 copies, less than 10 copies or at least 1 copy of a target nucleic acid prior to the multiplexed amplification reaction. In addition, less than a single genome equivalent of DNA can be utilized for amplification if the target nucleic acid locus is present in more than one copy in the genome. Generally, at least two loci, and up to approximately 250 loci can be simultaneously amplified within each target nucleic acid in a sample according to the methods described herein. Further, at least two loci and up to approximately 250 loci can be simultaneously amplified in a plurality of target nucleic acids according to the methods described herein.

The target nucleic acids utilized herein can be any nucleic acid, for example, human nucleic acids, bacterial nucleic acids, or viral nucleic acids. The target nucleic acid sample can be, for example, a nucleic acid sample from one or more cells, tissues, or bodily fluids such as blood, urine, semen, lymphatic fluid, cerebrospinal fluid, or amniotic fluid, or other biological samples, such as tissue culture cells, buccal swabs, mouthwashes, stool, tissues slices, biopsy aspiration, and archeological samples such as bone or mummified tissue. Target nucleic acids can be, for example, DNA, RNA, or the DNA product of RNA subjected to reverse transcription. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one source or different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples. Types of forensics samples include blood, dried blood, bloodstains, buccal swabs, fingerprints, touch samples (e.g., epithelial cells left on the lip of a drinking glass, the inner rim of a baseball cap, or cigarette butts), chewing gum, gastric contents, saliva, nail scrapings, soil, sexual assault samples, hair, bone, skin, and solid tissue. Types of environmental samples include unfiltered and filtered air and water, soil, swab samples from surfaces, envelopes, and powders.

For example, the methods herein can provide amplified nucleic acid samples whose analysis yields data suitable for forensic interpretation, and in particular, data that satisfies forensic interpretation guidelines. Such guidelines include signal strength, inter-loci peak height balance, heterozygous peak height ratio (PHR), incomplete non-template nucleotide addition (NTA), and stutter (Scientific Working Group on DNA Analysis Methods, *Short Tandem Repeat (STR) Interpretation Guidelines*. Forensic Science Communications, 2000, 2(3)).

The phrase "fluid communication" as used herein, refers to two chambers, or other components or regions containing a fluid, connected together so that a fluid can flow between the two chambers, components, or regions. Therefore, two chambers that are in "fluid communication" can, for example, be connected together by a microfluidic channel between the two chambers, such that a fluid can flow freely between the two chambers. Such microfluidic channels can optionally include one or more valves therein which can be closed or occluded, in order to block and/or otherwise control fluid communication between the chambers.

The term "poly(methyl methacrylate) or "PMMA," as used herein, means the synthetic polymers of methyl methacrylate, including but not limited to, those sold under the tradenames Plexiglas™, Limacryl™, R-Cast™, Perspex™, Plazcryl™, Acrylex™, ACrylite™, ACrylplast™, Altuglas™, Polycast™ and Lucite™, as well as those polymers described in U.S. Pat. Nos. 5,561,208, 5,462,995, and 5,334,424, each of which are hereby incorporated by reference.

The term "polycarbonate" as used herein means a polyester of carbonic acid and glycol or a divalent phenol. Examples of such glycols or divalent phenols are p-xylyene glycol, 2,2-bis(4-oxyphenyl)propane, bis(4-oxyphenyl) methane, 1,1-bis(4-oxyphenyl)ethane, 1,1-bis(oxyphenyl) butane, 1,1-bis(oxyphenyl)cyclohexane, 2,2-bis(oxyphenyl) butane, and mixtures thereof, including but not limited to, those sold under the tradenames Calibre™, Makrolon™, Panlite™, Makroclear™, Cyrolon™, Lexan™ and Tufak™.

As used herein the term "nucleic acid" is intended to encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-$N^6$-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGONUCLEOTIDES AND ANALOGUES, A PRACTICAL APPROACH, edited by F. Eckstein, IRL Press at Oxford University Press (1991); Antisense Strategies, Annals of the New York Academy of Sciences, Volume 600, Eds. Baserga and Denhardt (NYAS1992); Milligan, 1993, *J. Med. Chem.* 36:1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

The term "via" as used herein means a through-hole formed in a solid material to allow fluidic connection between the top and bottom surfaces of the material.

The terms "locus" and "loci" (plural) as used herein mean one or more specific positions on one or more nucleic acids (e.g., one or more chromosomes), as defined herein.

The terms "STR locus" and "STR loci" as used herein means a nucleotide sequence consisting of a repeating pattern of two or more nucleotides at a given locus of a target nucleic acid. The repeating pattern can range in length from 2 to 10 base pairs (bp), and is typically in the non-coding intron region.

According to one aspect of the invention, a thermal cycler is provided having the capability of heating and cooling a reaction solution rapidly, controllably, and reproducibly. An example of an embodiment of the thermal cycler of the invention is shown in FIG. 1A. The ability to rapidly heat and cool the reaction solution temperatures allows ramping and settling times to be minimized and incubation time at the desired temperature to dominate the total step time, enabling minimization of multiplex cycling times.

Figure 12:
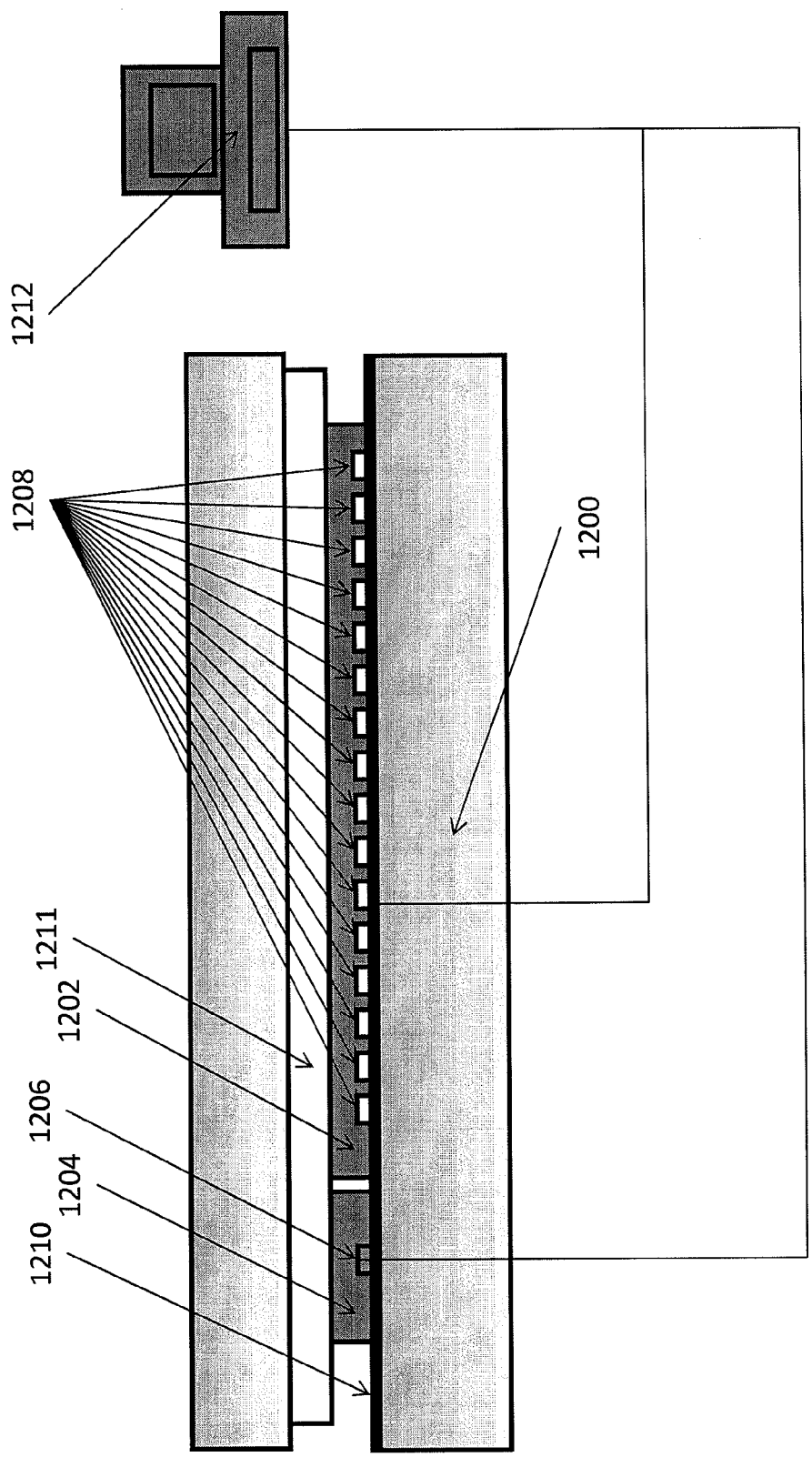
FIG. 12A is a schematic drawing of a first embodiment of a thermal cycler system comprising: a temperature control element (TCE) (1200) comprising a heating/cooling surface (1210); a biochip (1202) comprising reaction chambers (1208); an enclosure (1204) on the TCE separate from the biochip simulating the conditions within at least one reaction chamber; a thermo sensor (1206) associated with the enclosure (1204); a chip compression element (CCE) (1211) configured to provide a force to the biochip to hold it securely in contact with the heating/cooling surface (1210) of the TCE; and a controller (1212)
FIG. 12B is a schematic drawing of a second embodiment of a thermal cycler system comprising: a temperature control element (TCE) (1200) comprising a heating/cooling surface (1210); a biochip (1202) comprising a reaction chambers (1208), and a thermosensor (1206) within a sensing chamber (1205) on the biochip simulating the conditions within at least one reaction chamber; a thermo sensor (1206) associated with the sensing chamber (1205); a chip compression element (CCE) (1211) configured to provide a force to the biochip to hold it securely in contact with the heating/cooling surface (1210) of the TCE; and a controller (1212).
Figure 12:
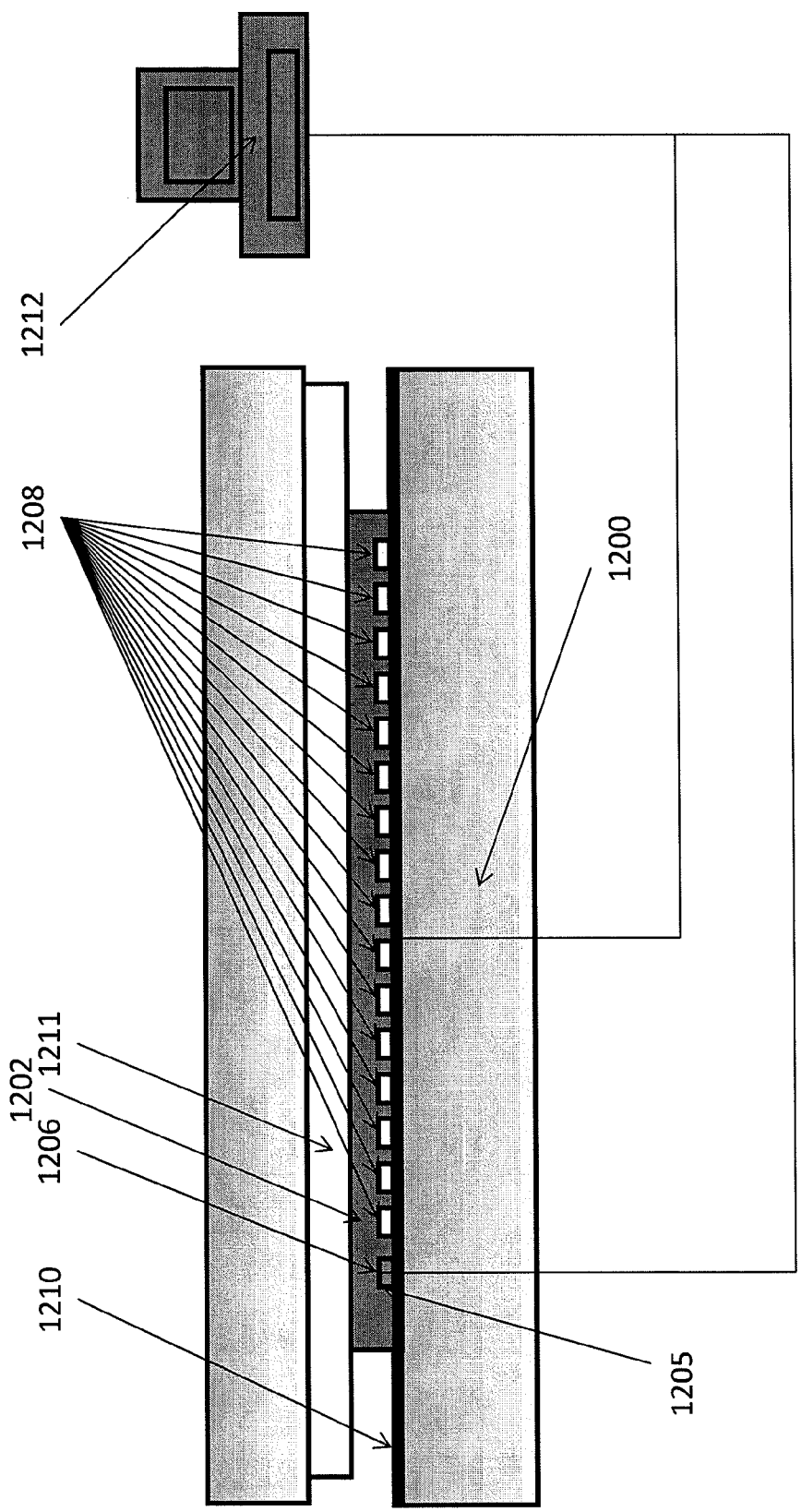

High heating and cooling rates can be achieved by utilizing a temperature control element (TCE), either alone or in fluid communication with a heat sink. A TCE comprises a means for heating and cooling, a thermosensor, a controller that receives signals from the thermosensor, and a power supply. In a preferred embodiment, a first surface of the TCE can be adapted to receive a sample chamber containing a solution and a sensing chamber containing an additional thermosensor. See FIG. 12B. In this setting, the thermosensor is positioned within the sensing chamber mounted to the TCE such that it simulates the conditions within the sample chamber. This sensing chamber is fabricated such that it has the same material stack-up as the sample chamber. A thermocouple mounted within the temperature sensor is embedded in the structure at an analogous position to that of the sample in the sample chamber. This sensor reports the effective temperature of the solutions in the sample chamber. Commercially-available Type-T or Type-K thermocouples (from Omega Engineering, Stamford, Conn.) are most applicable but other types of thermocouple and thermosensor may be used including thermisters, semiconductors, and infrared. The thermosensor within the sensing chamber provides feedback to the TCE to set or maintain the sample at the desired temperature. In this way, the sample temperature can be measured indirectly and controlled without inserting a thermosensor into the reaction chamber itself. Alternatively, a thermosensor can be placed directly into the reaction chamber and used to set and maintain sample temperature, eliminating the need for the sensing chamber. As one skilled in the art will appreciate, other types of sensors such as pressure sensors may be utilized according to the teachings of this invention.

The first surface of the TCE can be adapted to accept an essentially flat substrate by, for example, forming a recess in the first surface for accepting a substrate (e.g., a biochip, infra). Alternatively, the TCE can be adapted to accept one or more thin-walled tubes, defined as tubes with wall diameters with regions less than 200 µm thick. Preferably, the heat sink is a high efficiency heat sink, such as, but not limited to, fan-cooled heat sinks with copper bases and cooling fins. More preferably, the heat sink can be a fan cooled copper base and fins having a thermal resistance of about 0.4° C./W or less. A particular and non-limiting example of a high efficiency heat sink is E1U-N7BCC-03-GP (Coolermaster, Taiwan ROC).

The thermal cycler of the invention may further comprise a thermosensor positioned to monitor the temperature of the first surface of the TCE. Additional thermosensors can be added as desired to achieve further improvement in sample temperature control. The supplementary temperatures that can be monitored include those on multiple regions on and within the substrate, multiple regions on and within the heat sink, cooling air input and output, sample input and output, and ambient.

Good thermal communication between the TCE and the heat sink is desired. When the two mating surfaces are properly prepared, intimate physical contact is sufficient to provide adequate thermal transfer between the two components. Thermal interface materials (TIMs) between the TCE and heat sink can be used to enhance thermal coupling. Such TIMs include but are not limited to adhesives, greases, phase-change materials (PCMs), metal thermal interface materials, ceramic thermal interface materials, soft metal alloys, indium, alumina nano-layer coatings, submicron films, glycol, water, oils, antifreeze, epoxy compounds, and others. Specific examples include Arctic Silver or Ceramique (Arctic Silver, Visalia, Calif.; compounds that have thermal resistances of <0.007° C. in$^2$/W), compressible heat spring HSD4 (Indium Corp, Utica, N.Y.), HITHERM (GrafTech International Holdings Inc., Lakewood, Ohio), or directly bonding of the TCE to the surface of the heat sink. Thermal contact can be further enhanced by physical clamping the components together with a average force of more than 2 psi, or more than 5 psi, or more than 10 psi, or more than 30 psi, or more than 60 psi or more than 100 psi or more than 200 psi, or by direct bonding of the surfaces.

Thermal transfer between the TCE and a substrate in contact therewith can be increased with respect to block thermal cyclers, such as the Eppendorf Mastercycler™ ep gradient S thermal cycler (which provide heat energy via a silver block with high thermal conductivity and low specific heat capacity), by placing the substrate directly on the TCE. Suitable TCEs include, but are not limited to, a high heating and cooling capacity heat pump, and high power output Peltier devices; examples of Peltier devices are 9500/131/150B (Ferrotec, Bedford N.H.), XLT2393 (Marlow, Dallas Tex.). When utilized as a part of the TCE for thermal cyclers of the invention, Peltier devices are advantageously powered by an H-bridge. An example of an H-bridge device is the 5R7-001 (Oven Industries).

When Peltier devices are used as a part of the TCE for thermal cyclers of the invention, it is advantageous to power the Peltier devices by an H-bridge with pulse width modulation for heating and cooling. Temperature feedback from the thermosensor which measures the sample temperature drives the TCE to set and maintain the desired sample temperature. Closed-loop temperature control algorithms for control of the TCE include, but are not limited to, PID control and fuzzy logic control.

Said thermal controllers comprise a control algorithm that provides the capacity for rapid transition from one target temperature state to another target temperature state. This transition can be divided into 3 distinct phases. In phase 1, there is a large difference between the actual temperature and target temperature (for example 1 to 20° C. or higher). In this phase, ramping takes place at or near the maximum rate of the TCE device. In phase 2, the transition phase, the actual temperature and target temperature are closer (less than approximately 1 to 20° C.). In this case the controller must reduce the power to the TCE in order to prevent overshoot of the solution temperature and allow for rapid achievement of target temperature with minimal deviations and oscillations. In phase 3, the target temperature has been achieved and the controller moderates power to the thermal cycler to maintain the solution within a narrow range about the target temperature. Measurement of the temperature with the sensor provides more accurate feedback of the actual temperature and also allows the temperature of the TCE surface temperature to be overdriven. Each of the above 3 phases may be further subdivided into multiple sub-phases to provide for faster response time, more accurate temperature control, increased stability, and increased tolerance to external variability.

In one example, the temperature of the substrate can be measured by placing a thin thermocouple into a channel on the substrate surface. In another example, the second thermosensor can be housed in an enclosure, formed from essentially the same material as the substrate being utilized, that holds the second thermosensor essentially the same distance from the TCE as a reaction chamber on a substrate in contact with the TCE. Such a second thermosensor can generally be separate from the substrate (i.e., a stand-alone sensor), and can be placed next to the substrate on the first surface of the TCE. See FIG. 12A.

The heat sink may, optionally, further comprise a variable speed cooling fan and/or a second heating element for controlling the temperature of the heat sink, where each additional element of the heat sink is in communication with the second control element. This allows the cooling efficiency of the heat sink to be adjusted, in particular to keep the heat sink temperature essentially constant and independent of environmental temperature changes. The heater can also precondition the heat sink to essentially the operating temperature.

To facilitate thermal coupling of a reaction solution in a substrate and the TCE, uniform thermal communication of a contact surface of the substrate with the first surface of the TCE can be provided by applying a force to the substrate to secure it thereto while the thermal cycler is in operation. Such forces are preferably applied by means that only temporarily hold the substrate to the first surface of the TCE and can be readily removed upon completion of thermal cycling. For example, a chip compression element (CCE) can be situated above the first surface of the TCE to allow the substrate to be placed between. The chip compression element can then be engaged to hold the substrate in place during operation of the thermal cycler, and released to allow removal of the substrate. Proper integration of the CCE, TCE and heat sink allows the CCE to improve thermal coupling between and among all three of these components.

The portion of the CCE in contact with a substrate can be formed from a low thermal mass insulating material, including, but not limited to, a foam, for example WF71 Rohcell foam (Inspec foams, Magnolia, Ark.). For embodiments discussed herein the Rohacell is preferred. It has a specific heat capacity of 1.4-1.6 (J/gK) [or less thermal mass] and a thermal conductivity of 0.0345 W/mK (or less).

Biochip compression elements include, but are not limited to, one or more clamps, springs, compressible foam, or a pressurized air bladder which can be inflated to provide force to hold the substrate onto the first surface of the TCE. Preferably, the chip compression element provides a substantially uniform force of about 5 to about 250 psia to a surface of the substrate, and more preferably, about 20 to about 50 psia to hold the substrate to the first surface of the TCE. Notably, thermal communication between the contact surface of the biochip substrate and the TCE can be provided in the absence of a thermal coupling solutions such as thermal grease or glycol, although such can be utilized as necessary.

The biochip compression elements provide a force on the biochip-thermoelectric cooler-heat sink. This force serves to ensure good thermal contact and hence heat transfer between the biochip and the top surface of the TCE.

In one embodiment, the low thermal mass insulator is an air bladder and is utilized to provide the low thermal mass and insulating properties. In another embodiment, the low thermal mass insulator is a foam pad. The clamping force can be applied to the foam pad by a pneumatic cylinder, or closed cell foam pads under compression or air pressure from an air bladder. In the latter case, the air bladder provides both the insulation and the compressive force.

As described above, the thermal cycler can have a heating and/or cooling rate at the first surface of the TCE surface about 4-150° C. per second, and preferably about 8-150° C./sec, and more preferably about 10-150° C./sec. The thermal cycler can also have a heating or cooling rate at a solution within a reaction chamber of a substrate in uniform thermal communication with the first surface of the TCE (e.g., a biochip) of about 4-150° C. per second and preferably about 8-150° C./sec, and more preferably about 10-150° C./sec. Further, the thermal cycler of the invention can have a temperature stability of +/−1.0° C., and preferably +/−0.50° C., and more preferably +/−0.25° C.

Biochip

Figure 1B:
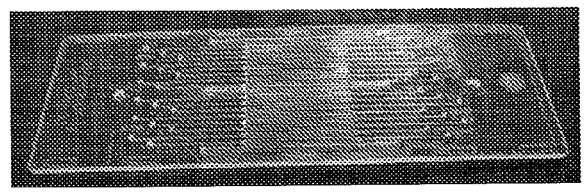
FIG. 1B is a photograph showing an embodiment of a 16-lane microfluidic biochip for use with the thermal cycler shown in FIG. 1A.

An embodiment of a biochip (i.e., a substrate for use with the thermal cycler of the invention) according to another aspect of the invention is shown for the sake of illustration in FIG. 1B as having 16 microfluidic systems, each comprising an inlet and an outlet in fluid communication with each of the reaction chambers formed within the biochip. However, such disclosure is not intended to be limiting, rather, one skilled in the art will readily recognize that the biochip can contain alternate numbers of microfluidic systems (infra) including biochips with one system and biochips with two or more systems. The term "plurality" as used herein, means two or more, four or more, eight or more, 16 or more, 32 or more, 48 or more, 64 or more, 96 or more, 128 or more, or 2-16, 2-32, 2-48, 2-64, 2-96, 2-128, 8-128, 8-64, or 8-32 microfluidic channels.

The biochip can comprise a substrate layer and a cover layer, where a portion of one or a plurality of microfluidic systems, comprising grooves and/or shaped depressions, are patterned into the substrate layer. A series of vias (i.e., through holes and/or inlets or outlets) can be formed in the cover layer to provide fluidic access to the microfluidic channels and reaction chambers, and can be located at any location about the biochip. Alternatively, vias can be formed in the substrate layer instead of the cover layer to achieve the same functionality. The top surface of the substrate layer can be bonded with the bottom surface of the cover layer to complete the microfluidic systems. Techniques for fabricating polymer-based microfluidic systems are reviewed extensively by Becker and Gartner (Becker, 2000, *Electrophoresis* 21, 12-26 and Becker, 2008, *Electrophoresis* 390, 89), which are hereby incorporated by reference in its entirety. Biochips can be fabricated using materials such as unsaturated, partially unsaturated or saturated cyclic olefin copolymers "COC", unsaturated, partially unsaturated, or saturated cyclic olefin polymers "COP", poly(methyl)methacrylate "PMMA", polycarbonate "PC", polypropylene "PP", polyethylene "PE", polyetheretherketone "PEEK", poly(dimethylsiloxane) "PDMA", polyimide "PI". It is important to select a plastic with a glass transition temperature greater than that of the maximal temperature to be utilized in the amplification reaction. Any number of these processes and materials can be used to fabricate the biochips described herein. In particular, the biochips can be prepared by injection molding of a plastic substrate, for example, a COC or COP based polymers (currently sold under the tradenames Topas™, Zeonex™, Zeonor™, and Apel™). In this fabrication methodology, an injection mold and mold insert consisting of the negative of the features to be formed is fabricated by machining and subsequent surface polishing. Together, the mold and insert allow the substrate layers to be fabricated and the formed substrate to comprise the channels, reaction chamber features and vias. The substrate and cover layers can be diffusion bonded by the application of heat and pressure.

Alternatively, the biochips can be prepared by hot embossing of thin thermoplastic films with a master die of the negative of the structure to be produced. The master die can be prepared by using electroforming to replicate the device prepared in a solid substrate. The solid substrate can be glass sheets that are patterned by standard photolithographic and chemical etching methods known to those skilled in the art. The substrate and cover layers are diffusion bonded by the application of heat and pressure.

The substrate and cover layers of the biochip can be constructed from a variety of plastic substrates including, but not limited to, polyethylene, poly(acrylates) (e.g., poly (methyl methacrylate)), poly(carbonate)s, and unsaturated, partially unsaturated or saturated cyclic olefin polymers (COP), or an unsaturated, partially unsaturated, or saturated cyclic olefin copolymers (COC). The thickness of plastic substrate and cover layers utilized in the present process is kept thin to minimize the mass thereof to thereby maximize thermal transfer between the thermal cycler and the reaction solution contained in each reaction chamber during their use. The plastic substrate and cover layers can each, independently, have a thickness of less than 2 mm, less than 1 mm, less than 750. m, less than 650 µm, less than 500 µm, less than 400 µm, less than 300 µm, less than 200 µm, or less than 100 µm; or plastic substrate and cover layers can each, independently, comprise a plastic having a thickness ranging from 25-2000 µm, 25-1000, 25-750 µm, 25-650 mm, 25-500 µm, 25-400 µm, 25-300 µm, 25-200 µm, or 25-100 µm. Preferably, at least one of the substrate and cover layers has a thickness of less than about 200 µm to maximize thermal transfer to the reaction solution contained in the reaction chambers of the biochip. More preferably, a contact surface of the biochip which is in contact with the first surface of the TCE has a thickness of less than about 200 µm.

Each reaction chamber can be formed to have a volume of, for example, less than 100 µL. Preferably, each reaction chamber has a volume of less than about 50 µL, or less than about 40 µL, or less than about 30 µL, or less than about 25 µL, or less than about 20 µL, or less than about 15 µL, or less than about 10 µL, or less than about 5 µL, or less than about 1 µL, or less than about 0.1 µL. Alternatively, each reaction chamber can be formed to have a volume ranging from about 0.1 µL, to about 100 µL. Preferably, each reaction chamber has a volume ranging from about 0.1 µL, to about 10 µL, or about 10 µL, to about 50 µL. The reaction chambers are generally not coated with a polymer or silane coating. Reaction chambers may be designed to have an inlet and an outlet channel. Alternatively, a single channel may be used for inlet and outlet.

The biochip design of the invention leverages the benefits of microfluidics including having a high surface to volume ratio and reduced diffusion times to maximize heat transfer, and uniform heating and cooling. The use of microfluidic technology also provides benefits with respect to a fully-integrated forensic analysis instrument. Further, biochips fabricated by diffusion bonding, and without the use of adhesives to bond the various layers (e.g. COC layers), were tested and demonstrated to be capable of withstanding from 100 to 1500 psi of pressure before failure based on the requirements of the desired application. For example, the biochips of the present invention withstand 450 psi, sufficient for the desired thermal cycling applications.

It is noted that the specific embodiments of the biochips of the invention set forth herein substantially lack any heating elements integrated into the biochip for heating and/or cooling the reaction chambers. Thermal cycling of the reaction chambers on the biochip is provided externally, for example, by the thermal cycler of the invention. Heating elements can be integrated into the biochips of the present invention, however.

In operation, one portion of the biochip can receive one or more reaction solutions, each independently comprising one or more reagents (e.g., for PCR) and or nucleic acid samples, through one or more inlets in fluid communication with one or more reaction chambers formed within the biochip. Simultaneous amplification of a plurality of samples can be performed by injecting each of the nucleic acid samples in a separate separation reaction chamber. An injector for simultaneously injecting a plurality samples into the plurality of sample or buffer wells can be provided with the biochip to enable simultaneous multiple sample amplification. Such injectors provide, for example, one sample of the plurality of samples to one reaction chamber of the plurality of reaction chambers. Injectors can introduce the samples to the channels according to any methods known to those skilled in the art, for example, by electrophoretic transport, pneumatic actuation or liquid actuation through a needle or tube or channel that connects the sample to the reaction chamber.

Following amplification (and optionally, nucleic acid extraction and quantification) the amplified nucleic acid product can be passed (e.g., to a Genebench-FX™100) through one or more outlets in fluid communication with the reaction chambers for fragment separation and generation of STR profiles.

The relatively low cost of plastic manufacture allows the biochips of the invention to be disposable, eliminating the labor required to reuse the biochip and essentially eliminating the possibility of contamination. A single-use disposable would be particularly advantageous for low copy number analyses in that no possibility of contamination (other than initial sample collection) would exist. In settings where neither contamination nor labor are major considerations, reusable plastic and glass biochips may be utilized.

Integration Methods

Using microfluidics allows fabrication of features to perform more than one function on a single biochip. These functions can include nucleic acid extraction, nucleic acid purification, pre-PCR nucleic acid cleanup, post-PCR cleanup, pre-sequencing cleanup, sequencing, post-sequencing cleanup, nucleic acid separation, nucleic acid detection, reverse transcription, pre-reverse transcription cleanup, post-reverse transcription cleanup, nucleic acid ligation, nucleic acid hybridization and quantification. Two or more of these functions can be connected microfluidically to enable sequential processing of a sample; this coupling is termed integration.

One form of microfluidic DNA extraction can be achieved by inserting a purification medium between an input and output channel. This purification medium can be silica fiber based and use chaotropic-salt reagents to lyse the biological sample, expose the DNA and bind the DNA to the purification media. The lysate is then transported via the input channel through the purification medium to bind the DNA. Bound DNA is washed by an ethanol based buffer to remove contaminants. This can be accomplished by flowing wash reagents via the input channel through the purification membrane. Bound DNA is then eluted from the membrane by flowing an appropriate low salt buffer (see, e.g., Boom, U.S. Pat. No. 5,234,809) via the input channel through the purification membrane and out the output channel.

One approach to DNA quantification in a microfluidic format is based upon real-time PCR. In this method of quantification, a reaction chamber is fabricated between an input and output channel. The reaction chamber is coupled to a thermal cycler and an optical excitation and detection system is coupled to the reaction chamber to allow fluorescence from the reaction solution to be measured. The amount of DNA in the sample is correlated to the intensity of the fluorescence from the reaction chamber per cycle (see, e.g., Heid et al., *Genome Research* 1996, 6, 986-994).

For further information about integration in microfluidic formats, see the U.S. patent application entitled "INTEGRATED NUCLEIC ACID ANALYSIS" filed 4 Apr. 2008, assigned U.S. patent application Ser. No. 12/080,751, now published as US 2009/0059222, which is hereby incorporated by reference in its entirety. For further information about separation and detection in microfluidic formats see the U.S. patent application entitled "Plastic Microfluidic Separation and Detection Platforms" filed U.S. patent application Ser. No. 12/080,745, now published as US 2009/0020427, which is hereby incorporated by reference in its entirety.

Microfluidic drives of the invention are means for transporting fluids within the reaction chambers of the integrated biochips. One type of microfluidic drive is effected by incorporated a membrane pump which transports the fluid by sequential application of positive and negative pressure to the membrane. Alternatively, a positive displacement pump can be connected to the input of the microfluidic chamber. A displacement of the pump forces the fluid through the microfluidic channel.

Integration can make use of microfluidic valves to gate fluid flow within the biochip. Valving can be accomplished with passive or active structures. Passive valving structures include capillary valves that stop fluid flow by utilizing capillary pressure. Fluids can flow through the capillary valving structure by the application of a pressure that is sufficiently large enough to overcome the capillary forces. Active valving structures include membrane valves which use flexible or semi-rigid structures at a point between two channels. The application of pressure on the membrane causes it to close the channel. The application of a vacuum to the membrane lifts it from the channel, allowing passage of fluids.

Amplification Methods

In yet another aspect, the invention provides methods for simultaneously amplifying a plurality of nucleic acid loci in one or more target nucleic acids via rapid polymerase chain reaction (PCR). Such methods comprise providing one or a plurality of reaction solutions to one or a plurality of reaction chambers, wherein each reaction solution comprises (i) at least one copy of at least one target nucleic acid, wherein each target nucleic acid is the same or different and each target nucleic acid independently comprises a plurality loci to be amplified; (ii) one or more buffers; (iii) one or more salts; (iv) a primer set corresponding to the plurality of loci to be amplified; (v) a nucleic acid polymerase; and (vi) nucleotides. Each of the reaction solutions, for example, each of the target nucleic acids, can be the same or different as necessary, for example, to run multiple simultaneous analyses on the same nucleic acid sample, or to simultaneously run multiple nucleic acid samples.

Each reaction chamber may be contained within a biochip of the invention as described above or thin-walled reaction tubes. Thin-walled reaction tubes preferably have a wall thickness of less than about 200 μm. Preferably, thin-walled reaction tubes preferably have a wall thickness of less than about 100 μm.

Primers for PCR amplification are oligonucleotide sequences that are specifically designed to hybridize to loci of the target DNA. These primers serve as starting points for polymerase extensions. To facilitate analysis of amplified fragments, labeled primers can also be used in PCR reactions. Labeled primers are oligonucleotide sequences that are coupled to a detectable moiety; a non-limiting example thereof is a fluorescent dye. When PCR is carried out with fluorescently labeled primers, amplicons with a fluorescent label are generated. The methods for performing fast PCR are compatible with both labeled and unlabeled primers, and fast multiplexed PCR have been demonstrated.

Primer sets can be any known to those skilled in the art for the amplification of a plurality of loci with a target nucleic acid, as described above. For example, primers useful in amplification of one or more loci in a human nucleic acid sample are described in U.S. Pat. No. 5,582,989; U.S. Pat. No. 5,843,660; U.S. Pat. No. 6,221,598; U.S. Pat. No. 6,479,235; U.S. Pat. No. 6,531,282; and U.S. Pat. No. 7,008,771; and US Patent Application Publication Nos. 2003/0180724; 2003/0186272; and 2004/0137504, each of which are hereby incorporated by reference.

Further, primers useful in amplification of one or more loci in a viral nucleic acid sample are described in, for example, U.S. Pat. No. 7,312,036; U.S. Pat. No. 6,958,210; U.S. Pat. No. 6,849,407; U.S. Pat. No. 6,790,952, and U.S. Pat. No. 6,472,155, each of which are hereby incorporated by reference.

Examples of primers useful in amplification of one or more loci in a bacterial nucleic acid sample are described in U.S. Pat. No. 7,326,779; U.S. Pat. No. 7,205,111; U.S. Pat. No. 7,074,599; U.S. Pat. No. 7,074,598; U.S. Pat. No. 6,664,080; and U.S. Pat. No. 5,994,066, each of which are hereby incorporated by reference.

Salts and buffers include those familiar to those skilled in the art, including those comprising $MgCl_2$, and Tris-HCl and KCl, respectfully. Buffers may contain additives such as surfactants (e.g., Tweens), dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphophate (dCTP), deoxyguanosine triphosphate (dGTP) and deoxythymidine triphosphate (dTTP) are also added to the synthesis mixture in adequate amount for amplification of the target nucleic acid.

The solutions can be optionally heated to and held at a first temperature for a first period of time suitable for hot-start activation of the nucleic acid polymerases. Generally, the first period of time is less than about 90 seconds. The first temperature can be about 95 to about 99° C. Polymerases with hot start mechanisms that can be activated in 60 seconds or less include those utilizing antibody mediated hot-start and aptmer mediated hot start mechanisms. Alternatively, hot-start polymerases need not be utilized in the present invention.

Subsequently, the temperature of the reaction solutions are sequentially cycled between a denaturing state, an annealing state, and an extension state for a predetermined number of cycles. Generally, the one or a plurality of reaction solutions are cooled from the denaturing state to the annealing state at a first cooling rate of about 1 to about 150° C./sec, or about 1 to about 100° C./sec; or about 1 to about 80° C./sec; or about 1 to about 60° C./sec; or about 1 to about 40° C./sec; or about 1 to about 30° C./sec; or about 1 to about 20° C./sec; about 4 to about 150° C./sec, or about 4 to about 100° C./sec; or about 4 to about 80° C./sec; or about 4 to about 60° C./sec; or about 4 to about 40° C./sec; or about 4 to about 30° C./sec; or about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. The one or a plurality of reaction solutions can be heated from the annealing state to the extension state at a first heating rate of about 1 to about 150° C./sec, or about 1 to about 100° C./sec; or about 1 to about 80° C.; or about 1 to about 60° C./sec; or about 1 to about 40° C./sec; about 1 to about 30° C./sec; about 1 to about 20° C./sec; 4 to about 150° C./sec, or about 4 to about 100° C./sec; or about 4 to about 80° C./sec; or about 4 to about 60° C./sec; or about 4 to about 40° C./sec; about 4 to about 30° C./sec; about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec; and/or the one or a plurality of reaction solutions are heated from the extension state to the denaturing state at a second heating rate of about 1 to about 150° C./sec, or about 1 to about 100° C./sec; or about 1 to about 80° C./sec; or about 1 to about 60° C./sec; or about 1 to about 40° C./sec; about 1 to about 30° C./sec; about 1 to about 20° C./sec; about 4 to about 150° C./sec, or about 4 to about 100° C./sec; or about 4 to about 80° C./sec; or about 4 to about 60° C./sec; or about 4 to about 40° C./sec; about 4 to about 30° C./sec; about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. Finally, the reaction solutions are held at a final state to provide one or a plurality of amplified nucleic acid products.

Denaturing states can range generally include from about 90 to 99° C. for times ranging from about 1 to 30 seconds. The actual times and temperatures are enzyme, primer and target dependent. For the Applied Biosystems (AB) multiplexed STR kit for amplifying human genomic DNA, about 95° C. for about 5 sec. being preferred.

The annealing temperature and time influence the specificity and efficiency of primer binding to a particular locus within a target nucleic acid and are particularly important for multiplexed PCR reactions. The correct binding of a complete set of primer pairs during the annealing step can allow production of multiplexed amplification of a plurality of loci, for example, one or a plurality of full STR profiles with acceptable PHR and inter-locus signal strength balance. For a given primer pair, annealing states can range from about 50° C. to 70° C. and times from about 1 to 30 seconds. The actual times and temperatures are enzyme, primer, and target dependent. For the AB multiplexed STR kit for amplifying human genomic DNA, about 59° C. for 15 seconds is preferred.

Extension temperature and time primarily impact the allele product yield and are an inherent property of the enzyme under study. It should be noted that the extension rates reported by the manufacturer are often provided for singleplex reactions; extension rates for multiplex reactions can be much slower. For a given enzyme, extension states can range from about 60 to 75° C. and times from about 1 to 30 seconds. The actual times and temperatures are enzyme, primer, and target dependent. For the AB multiplexed STR kit for amplifying human genomic DNA, about 72° C. for about 5 seconds is preferred. Preferably, for continuing a predetermined number of cycles, the reaction solution is heated from the extension state to the denaturing state at a third rate of about 1 to about 150° C./sec, or about 1 to about 100° C./sec; or about 1 to about 80° C./sec; or about 1 to about 60° C./sec; or about 1 to about 40° C./sec; or about 1 to about 30° C./sec; or about 1 to about 20° C./sec; 4 to about 150° C./sec, or about 4 to about 100° C./sec; or about 4 to about 80° C./sec; or about 4 to about 60° C./sec; or about 4 to about 40° C./sec; or about 4 to about 30° C./sec;

or about 4 to about 20° C./sec; or about 10 to about 150° C./sec; or about 10 to about 100° C./sec; or about 10 to about 80° C./sec; or about 10 to about 60° C./sec; of about 10 to about 40° C./sec; or about 10 to about 30° C./sec; or about 10 to about 20° C./sec. Generally, the predetermined number of cycles is chosen to be about 10 to about 50 cycles, although fewer or more cycles may be used as necessary.

Final extension times can be reduced significantly until incomplete NTA begins to increase. For a given enzyme, final extension temperatures can range from about 60 to 75° C. and times from about 0 to 300 seconds. The actual times and temperatures are enzyme, primer, and target dependent. For the AB multiplexed STR kit for amplifying human genomic DNA, about 72° C. for about 90 seconds is preferred.

In addition to the 3-step thermal cycling approach set forth above, this process is also amenable to 2-step thermal cycling approaches. In this approach, the reaction solutions are sequentially cycled between a denaturing state, and an annealing/extension state for a predetermined number of cycles. This approach utilizes primers designed to anneal at the extension temperature, allowing the annealing and extension steps to share the same temperature. The reduced number of temperature transition results in a further reduction in the cycle time.

In certain embodiments, a plurality of amplified nucleic acid products can be obtained in about 5 to about 20 minutes. In certain other embodiments, a plurality of amplified nucleic acid products can be obtained in about 5 to 10 minutes, about 1 to 5 minutes, or less than 5 minutes. Each amplified nucleic acid product can be generated starting from less than about 10 ng of a target nucleic acid. Preferably, amplified nucleic acid products can be generated starting from less than about 5 ng or less than about 2 ng of nucleic acid, or less than about 1 ng of nucleic acid, or less than about 0.5 ng of nucleic acid, or less than about 0.2 ng of nucleic acid, or less than about 0.1 ng of nucleic acid, or less than about 0.05 ng of nucleic acid, or less than about 0.006 ng of nucleic acid.

In other embodiments, such as the identification of biological weapons agents in clinical or environmental samples or the diagnosis of bacterial, viral, or fungal infections in humans, plants, and animals, amplified nucleic acid products can be generated starting from at least one copy of a target nucleic acid. For example, a sample to be analyzed can comprise less than 1000 copies (e.g., 1-1000 copies), less than 400 copies, less than 200 copies, less than 100 copies, less than 50 copies, less than 30 copies, less than 10 copies or 1 copy of a target nucleic acid prior to the multiplexed amplification reaction.

In addition, less than a single genome equivalent of DNA can be utilized for amplification if the target nucleic acid locus is present in more than one copy in the genome.

In any of the preceding methods, the thermal cycling can be performed for a predetermined number of cycles to achieve sufficient amplification of the loci in the target nucleic acid as can be readily determined by one skilled in the art. For example, the predetermined number of cycles can range between about 10 and about 50 cycles, and preferably between about 20 and 50 cycles. Further, in any of the preceding methods, at least 2 loci of one or a plurality of nucleic acids can be simultaneously amplified. Depending on the desired application, greater than four, 5 to 10, 10 to 20, 20 to 30 or about 10 to 250 loci are simultaneously amplified For example, for amplification of STR loci, 10-20 loci may be preferred.

Preferably, the temperature of the reaction solutions is cycled by a thermal cycler of the invention (supra). While it can be possible to utilize commercial block thermal cyclers for fast thermal cycling by the compensating for lagging response of the PCR solution by setting the block temperature higher than the desired solution temperature on heating steps and setting the block temperature lower than the desired solution temperature on cooling steps, this mode of operation is cumbersome to implement as the temperature setpoints required to compensate for the slow ramping response must be determined empirically. Furthermore, as feedback and control are still performed by the block and no monitoring of the solution temperature takes place, the repeatability and reproducibility of the profile can be influenced by external factors including the changes in the room temperature. Hence, the temperature profile of the solution is not reproducible.

Many commercially available polymerases can be adapted for use in fast PCR applications using the approaches described here. Typically, the nucleic acid polymerase has an extension rate of at least 100 bases/sec. A large number of polymerases available for PCR amplification including *Thermus aquaticus* (Taq), *Pyrccoccus furiosus* (Pfu), *Pyrococcus woesei* (Pwo), *Thermas flavus* (Tfl), *Themus thermophilus* (Tth), *Thermus litoris* (Tli) and *Thermotoga maritime* (Tma). These enzymes, modified version of these enzymes, and combination of enzymes, are commercially available from vendors including Roche, Invitrogen, Qiagen, Strategene, and Applied Biosystems. Representative enzymes include PHUSION (New England Biolabs, Ipswich, Mass.), Hot MasterTaq™ (Eppendorf), PHUSION Mpx (Finnzymes), PyroStart (Fermentas), KOD (EMD Biosciences), Z-Taq (TAKARA), and CS3AC/LA (KlenTaq, University City, Mo.). A widely used enzyme for PCR amplification for STR typing is the Taq polymerase, and the TaqGold variant is supplied with the Identifiler™, Profiler™, and COfiler™ kits.

In certain embodiments, the PCR conditions presented here can generate full STR profiles from a human target nucleic acid with high efficiency, although production of a full profile is not required. A full profile for autosomal STR can comprise loci such as amelogenin, D8S1179, D21S11, D7S820, CFS1PO, D3S1358, TH01, D13S317, D16S539, D2S1338, D19S433, vWA, TPOX, D18S51, D5S818, FGA, or a plurality thereof. Other STR loci including mini-STRs, and Y-STR analysis. The criteria for optimization of the protocols include the generation of full profiles, signal strength, dynamic range, inter-locus signal strength balance, PHR, incomplete NTA, stutter, and total cycle time.

According one embodiment, protocols using the SpeedSTAR enzyme and the thermal cycler of the invention can reduce the total cycling time for biochip and tube reactions to 17.3 and 19.1 min respectively, to generate full STR profiles. In the protocol, the denaturing state is about 98° C. for about 4 seconds, the annealing state is about 59° C. for about 15 seconds, the extension state is about 72° C. for about 7 seconds, and the final state is about 70° C. for about 90 seconds.

In certain embodiments, the total cycling time for at least 10, 20, or 30 multiplexed PCR cycles can range from about 1 minute to about 90 minutes. Preferably, total cycling time for at least 10, 20, or 30 multiplexed PCR cycles ranges from about 1 minute to about 90 minutes; or from about 1 minute to about 85 minutes; or from about 1 minute to about 80 minutes; or from about 1 minute to about 75 minutes; or from about 1 minute to about 70 minutes; or from about 1 minute to about 65 minutes; or from about 1 minute to about 60 minutes; or from about 1 minute to about 55 minutes; or from about 1 minute to about 50 minutes; or from about 1 minute to about 45 minutes; or from about 1 minute to about 40 minutes; or from about 1 minute to about 35 minutes; or from about 1 minute to about 30 minutes; or from about 1 minute to about 25 minutes; or from about 1 minute to about 20 minutes; or from about 1 minute to about 15 minutes; or from about 1 minute to about 10 minutes or from about 1 minute to about 5 minutes. In other embodiments, the total cycling time for at least 10, 20, or 30 multiplexed PCR cycles is less than about 90 minutes. Preferably, the total cycling time for at least 10, 20, or 30 multiplexed PCR cycles is less than about 89, 85, 80, 75, 70, 65, 60, 55, 50, 45, 40, 35, 30, 25, 20, 15, 10, 5, 4, 3, 2, or 1 minute.

The invention contemplates an integrated biochip comprising one or a plurality of microfluidic systems, for performing the multiplexed PCR amplification of a plurality of loci within a nucleic acid sample as well as at least one other sample preparation and/or analysis method within the same biochip platform. For example, within each microfluidic system on a biochip, each having a flow direction from an inlet port to an outlet port, the system can comprise a plurality of reaction chambers, wherein a first reaction chamber of the plurality of reaction chambers is in fluid communication with the inlet port, and an ultimate reaction chamber of the plurality of reaction chambers is in fluid communication with the outlet port, and at least one microchannel fluidly connecting each consecutive pair of reaction chambers along the flow direction. At least one reaction chamber in each microfluidic system can be less than 200 µm from a contact surface of the biochip substrate to facilitate thermal communication with a thermal cycler of the invention for performing multiplexed PCR within said reaction chamber.

Each of the remaining reaction chambers within each of the microfluidic systems of the biochip can be adapted for nucleic acid extraction, nucleic acid purification, nucleic acid hybridization, nucleic acid ligation, pre-PCR nucleic acid cleanup, post-PCR cleanup, pre-sequencing cleanup, sequencing, post-sequencing cleanup, separation and detection, reverse transcription, pre-reverse transcription cleanup, and/or post-reverse transcription cleanup, electrophoretic separation, nucleic acid detection. The term "cleanup" as used herein means the removal of reaction components (including anions, cations, oligonucleotides, nucleotides, preservatives, enzymes, or inhibitors) that may interfere with any of the reaction chamber processes listed above.

The Examples which follow are illustrative of specific embodiments of the invention, and various uses thereof. They set forth for explanatory purposes only, and are not to be taken as limiting the invention.

EXAMPLES

Example 1

Custom Thermal Cycler and Microfluidic Biochip

A thermal cycler of the invention, as shown in FIG. 1A, was used to perform fast cycling by allowing the PCR reaction solution temperatures to be heated and cooled rapidly, controllably, and reproducibly. This instrument accepts a 16-chamber microfluidic biochip and consists of a high output thermoelectric cooler/heater mounted to a high efficiency heat sink. Each of 16 PCR reaction solutions was placed into an individual chamber of the microfluidic biochip, coupled to the heat pump by applying a 0.2 MPa of compressive pressure with a clamping mechanism. FIG. 1B shows a photograph of the 16-sample disposable plastic microfluidic biochip. Each PCR chamber is 500 µm deep and approximately 1 mm wide and holds 7 µl of PCR reaction solution.

Instrumentation and Temperature Profiles

In the following examples, all amplification reactions in tubes were performed with an Eppendorf Mastercycler™ ep gradient S (Eppendorf North America, Westbury, N.Y.). Block temperature profiles of the above instrument were obtained using a 127 µm diameter type K thermocouple sensor which was attached directly to the block. For reaction solution profiles a 127 µm diameter type K thermocouple sensor was placed in the 20 µL reaction solution, within a thin-walled PCR tube. Data acquisition was performed with an Omega HH506RA Multilogger thermometer set to acquire data at a rate of 100 Hz.

Amplification reactions in biochips were performed using the thermal cycler of Example 1 with 16-sample plastic biochips as the reaction vessels. The solution temperature within the microfluidic biochip was monitored by inserting a thermocouple into a sensing chamber within the biochip.

PCR—Reaction Mix Components and Cycling Conditions

Multiplex PCR reactions were performed with the AmpFtSTR® Profiler Plus® ID PCR Amplification Kit (Profiler Plus ID kit) (Applied Biosystems, Foster City, Calif.) using 9947A genomic DNA (Promega, Madison, Wis.) as a template. Polymerases used for amplification were either AmpliTaq Gold® DNA Polymerase (TaqGold™) supplied with the Profiler Plus ID kit or other polymerases: SpeedSTAR HS DNA Polymerase (SpeedSTAR) (Takara BIO USA Inc., Madison, Wis.), KOD Hot Start DNA Polymerase (KOD) (EMD Biosciences Inc., Gibbstown, N.J.), or PyroStart™ Fast PCR Master Mix (PyroStart) (Fermentas Inc., Glen Burnie, Md.). Multiplex PCRs with other polymerases were carried out using the labeled multiplex primer set from the Profiler Plus ID kit in combination with the polymerase specific buffers and dNTPs. All tube PCRs were carried out in 0.2 mL thin-walled PCR tubes (Eppendorf North America, Westbury, N.Y.) using the Eppendorf Mastercycler™ ep gradient S. All biochip reactions were amplified in the thermal cycler of FIG. 1A using 16-sample biochips.

The following PCR reaction mixtures were prepared and used for thermal cycling:

Standard TaqGold™ Reactions:

Standard TaqGold™ multiplex reactions consisted of 9.55 µL Profiler Plus ID reaction mix, 1 ng 9947A genomic DNA, 5 µL Profiler Plus ID Primer set and 2.25 U TaqGold™ in a 25 µL reaction volume. Cycling conditions (block temperatures and times) were chosen following the manufacturers recommendations and set to an initial 95° C. for 11 min (hot start) followed by 28 cycles of 1 min at 94° C. (denaturing), 1 min at 59° C. (annealing), 1 min at 72° C. (extension) and a final extension of 45 min at 60° C.

Optimized TagGold™ Reactions:

TaqGold™ reactions optimized for fast cycling were carried out in a 10 µL reaction volume containing 3.82 µL Profiler Plus ID reaction mix, 1 ng 9947A genomic DNA, 2 µL, Profiler Plus ID Primer set and 0.9 U TaqGold™. Reactions were cycled at 95° C. for 11 min, 28 cycles 10 s, 98° C.; 45 s, 59° C.; 30 s, 72° C. and a final extension of 15 min at 72° C.

SpeedSTAR Tube Reactions:

SpeedSTAR PCR mix components for tube PCR were: 2 µL, Profiler Plus ID primer set, 9947A genomic DNA, 1.times. Fast Buffer I (Takara BIO USA Inc., Madison, Wis.), 200 µM dNTPs and 0.315 U SpeedSTAR in a 10 µL, reaction volume. Cycling conditions for fast performance were set to: 1 min at 95° C. (enzyme activation) followed by 28 cycles of 4 s at 98° C., 15 s at 59° C., 5 s at 72° C. and a 1 min at 72° C. final extension.

SpeedSTAR Biochip Reactions:

For biochip PCR the 7 µL reaction mix contained 1.4 µL, Profiler Plus ID primer set, 9947A genomic DNA, 1×Fast Buffer I buffer, 200 µM dNTPs and 0.42 U SpeedSTAR. Cycling parameters were set to 70 s at 95° C., 28 cycles of 4 s, 98° C.; 15 s, 59° C.; 7 s, 72° C. and a final extension of 1:30 min at 70° C.

KOD Reactions:

Amplification with KOD were performed with 2 µL, Profiler Plus ID primer set, 1×KOD buffer (EMD Biosciences Inc., Gibbstown, N.J.), 200 µM dNTPs, 1 ng 9947A genomic DNA, 1.5 mM MgSO$_4$, 0.2 U KOD in a 10 µL, reaction volume. Cycling conditions were: 2 min, 95° C. followed by 28 cycles of 4 s, 98° C.; 30 s, 59° C.; 10 s, 72° C. with a final extension of 1 min, 72° C.

PyroStart Reactions:

Reaction mixtures with PyroStart in a 1× final concentration also contained 20 µL, Profiler Plus ID primer set and 1 ng 9947A genomic DNA in a 10 µL, reaction and were cycled at: 1 min, 95° C. and 28 cycles of 4 s, 98° C.; 20 s, 59° C.; 30 s, 72° C. followed by a final extension of 1 min at 72° C.

Multiplex PCR with Other STR Typing Kits:

The suitability of SpeedSTAR to generate full STR profiles with other STR typing kits (AmpFlSTR® Identifiler® (Identifiler), AmpFlSTR® COfiler®PCR Amplification Kit (COfiler), (Applied Biosystems) was tested in tube and biochip with the reaction conditions as described above for SpeedSTAR with the Profiler Plus ID kit. In these reactions, the Profiler Plus ID primer sets were replaced with the primer set from each of the kits.

Reproducibility

Reproducibility studies in tube and biochip were performed with TaqGold™ and SpeedSTAR using 1 ng 9947A genomic DNA as a template. For tube reproducibility 5 individual reactions were prepared. Biochip reproducibility was determined in 3 biochip PCR runs with 8 reactions each.

Sensitivity

Sensitivity studies for SpeedSTAR amplification in tube and biochip were performed using the following amounts of 9947A template DNA: In tube: 4 ng, 2 ng, 1.5 ng, 1 ng, 0.5 ng, 0.25 ng, 0.125 ng, 0.1 ng, 0.05 ng, 0.03 ng, 0.02 ng, 0.01 ng, 0.006 ng; in biochip: 4 ng, 2 ng, 1.5 ng, 1 ng, 0.5 ng, 0.25 ng, 0.1 ng, 0.05 ng, 0.025 ng, 0.02 ng, 0.015 ng, 0.01 ng, 0.006 ng. The reactions at each template level were performed in duplicate.

STR Separation and Detection Instrumentation

Amplified products were separated and detected using the Network Biosystem Genebench-FX™ Series 100 (Pyzowski and Tan, *Advances in Biochip-Based Analysis: A Rapid Field-Based Approach* 59th Annual Meeting of the American Academy of Forensic Sciences San Antonio, Tex., Feb. 19-24, 2007). This instrument was developed and optimized specifically for STR analysis. To 2.7 µL of each amplified product 10.2 µL Hi-Di™ formamide and 0.1 µL of Genescan 500 LIZ internal lane standard (both Applied Biosystems, Foster City, Calif.) were added. After denaturation at 95° C. for 3 min and snap cooling on ice, samples were loaded into the separation chip and electrophoretically moved into the separation channels by applying a 350 V/cm electric field for 90 seconds. This was followed by the application of a 150 V/cm electric field along the separation channel to separate the DNA fragments. All separations were carried out at 50° C.

Data Analysis

Data was analyzed with the GeneMarker® HID STR Human Identification Software, Version 1.51 (SoftGenetics LLC, State College, Pa.). Signal strengths were normalized to the internal lane standard and the percentages of stutter, incomplete NTA as well as PHR were determined. PHR is calculated by dividing the lower signal strength allele by the higher signal strength allele within the locus. The level of incomplete NTA is calculated by dividing the signal strength of the template fragment (−A) by the signal strength of the adenylated fragment (+A).

Example 2

Figure 2A:
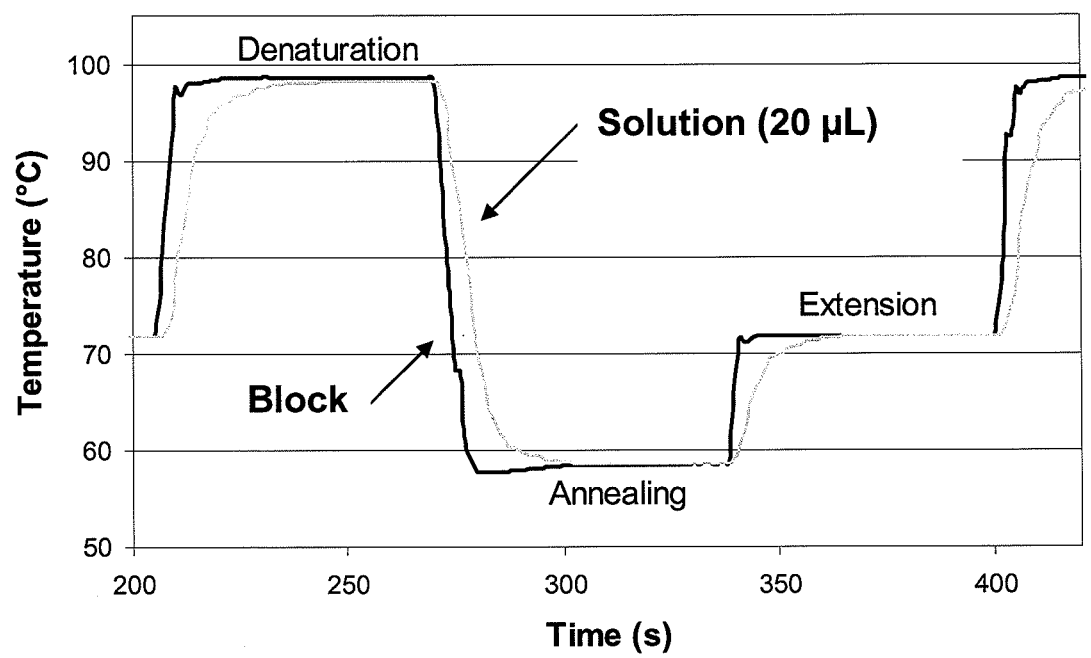
FIG. 2A is a graph showing the temperature profiles of block and reaction solution for one thermal cycle of the standard STR cycling protocol described herein (total cycling time: 145.1 minutes).

Temperature Profiles of Thermal Cycling Instruments and Reaction Solutions in Conventional PCR Tubes and Microfluidic Biochips Amplification reactions were performed in thin-walled PCR tubes using a commercial thermal cycler and in microfluidic biochips using the thermal cycler of Example 1. For tube reactions, the Eppendorf Mastercyler™ was utilized. FIG. 2A shows the temperature of the block and the reaction solution within a tube for one of the 28 thermal cycles using a conventional STR cycling protocol. The Mastercycler™ heating and cooling system is based on a heat pump with an integrated block for tube insertion. The time and temperature setpoints are 1 minute at 98° C. for denaturation, 1 minute at 59° C. for annealing, and 1 minute at 72° C. for extension. A comparison of the temperature profiles for the heat block and the reaction solution shows a lag in the response of the solution temperature relative to the block temperature. The measured heating and cooling rates of the block are 5.6° C./sec and 4.9° C./sec and of the solution are 4.8° C./sec and 3.3° C./sec. The block makes the temperature transition from extension (72° C.) to denaturation (98° C.) in 14 seconds, but the solution does not achieve the setpoint temperature for 39 seconds. Transitions between the denaturation and annealing steps (59° C.) take 10 and 27 seconds and between the annealing and extension steps take 7 and 24 seconds for the block and solution respectively.

Figure 2B:
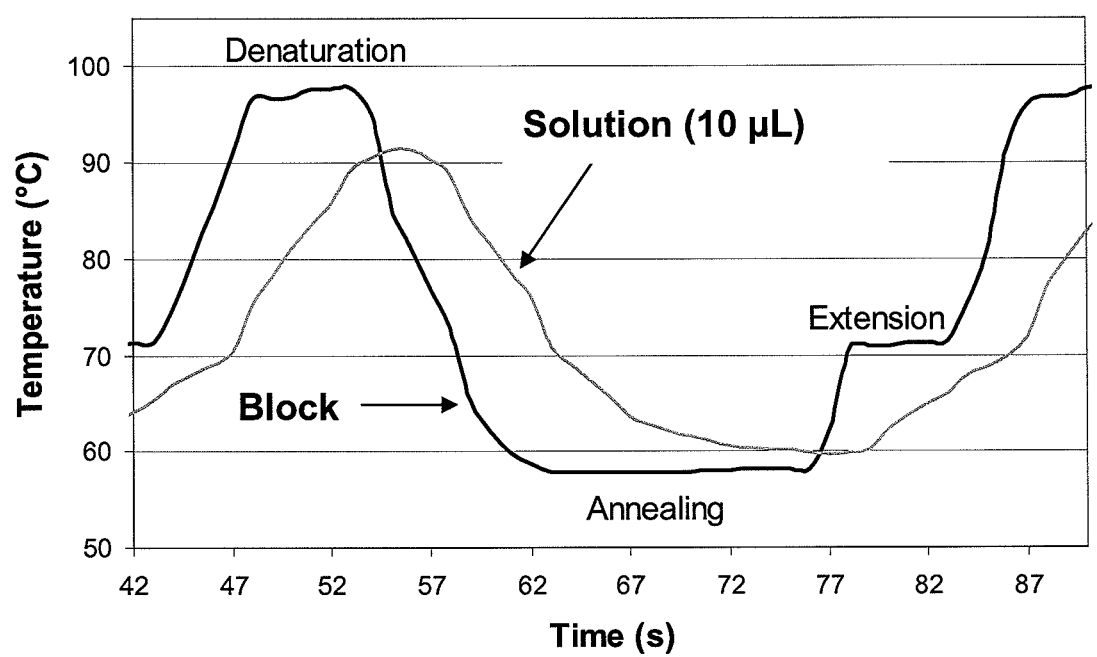
FIG. 2B is a graph showing the temperature profiles of block and reaction solution for one thermal cycle of the fast cycling protocol described herein (total cycling time: 19.56 minutes).

The temperature profiles of the Eppendorf Mastercyler™ block and the reaction solution for one of the 28 thermal cycles under fast cycling conditions are shown in FIG. 2B. The time and temperature setpoints are 5 seconds at 98° C. for denaturation, 15 seconds at 59° C. for annealing, and 5 seconds at 72° C. for extension. However, the delayed and dampened response of the solution prevents it from achieving the desired setpoint temperatures.

Figure 3:
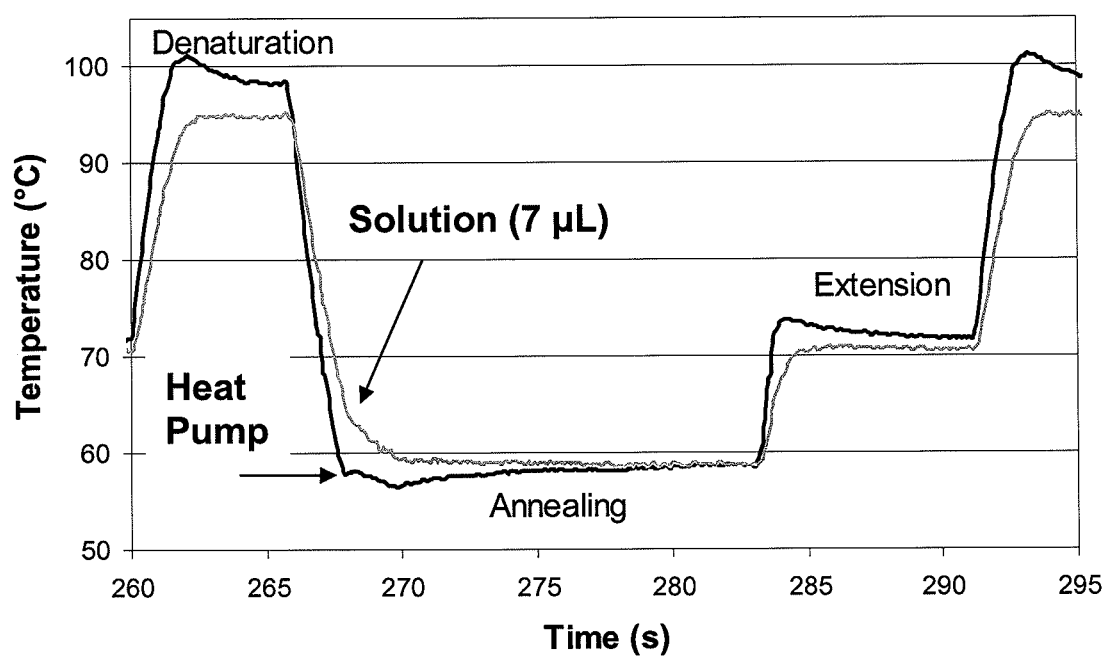
FIG. 3 is a graph showing temperature profiles of the heat pump and the reaction solution for one thermal cycle for a thermal cycler of the invention using fast cycling conditions (total cycling time: 17.3 minutes).

The temperature profiles of the heat pump and the reaction solution for one of the 28 thermal cycles for the thermal cycler of the invention using fast cycling conditions were also determined (FIG. 3). For the determination of the reaction solution temperature, a sensing chamber within the biochip was used. The time and temperature setpoints are 4 seconds at 95° C. for denaturation, 15 seconds at 59° C. for annealing, and 7 seconds at 72° C. for extension. The measured heating and cooling rates of the heat pump are 21.5° C./sec and 21.7° C./sec, and the measured heating and cooling rates of the reaction solution are 14.8° C./sec and 15.4° C./sec.

Accordingly, the thermal cycler of the invention is capable of heating and cooling the reaction solution at a rate that is 3 to 5 times faster than the commercial block-based cycler. The transition times between extension, denaturation, and annealing steps for the heat pump are 1.7, 2.1, and 0.7 seconds and for the solution 2.7, 4.5, and 2.2 seconds. The thermal cycler of the invention allows the reaction solution to reach the required temperatures approximately 7-fold faster than the block-based cycler, resulting in defined and controlled incubation temperatures and times under fast cycling conditions.

Example 3

Evaluation of PCR Enzymes in Tubes

A large number of polymerases were evaluated for potential use for fast, multiplexed STR analysis, and candidates were selected based in part on hot-start activation time and extension rate. The reported properties of the four polymerases selected for experimental evaluation compared with recommended conditions for TaqGold™ are presented in Table 1 (A).

from the Profiler Plus ID kit and vendor recommended buffers and enzyme concentrations, and resulting profiles were separated, detected, sized, and quantified using Genebench-FX™ Series 100. Various times and temperatures for the denaturation, annealing, and extension steps were determined to give total times for PCR amplification with signal strengths suitable for STR interpretation ranging from 19.13 minutes for SpeedSTAR to 71.7 minutes for TaqGold™ [Table 1(B)]. Method conditions of the invention allow amplification to be performed 2-10 fold more rapidly than recommended conditions for TaqGold™.

Further evaluation of the enzymes for forensically relevant performance includes signal strength, levels of stutter and incomplete NTA and PHR [Table 1(B)]. All enzymes are capable of performing highly multiplexed amplification using the Profiler Plus ID primers. Signal strengths for SpeedSTAR, Pyrostart, KOD, and optimized TaqGold™ reactions are all either approximately the same or higher than those generated using standard TaqGold™ PCR conditions.

TABLE 1A

Reported Polymerase characteristics

| Polymerase | ATG | SpeedSTAR | PyroStart | KOD |
|---|---|---|---|---|
| 3'-5' Exonuclease activity | No | Yes, <20% | No | Yes |
| Generation of 3'-dA overhangs | Yes | Yes, >80% | Yes | No |
| Hot Start mechanism | Chemical modified | Antibody | Chemical modified | Antibody |
| Initial activation | 95° C./11 min | 95° C./1 min | 95° C./1 min | 95° C./2 min |
| Elongation rate [nucleotides/sec] | 16.67 | 100-200 | 40 | 100 |

TABLE 1B

Optimized performance of polymerases in tube reactions

|  | Standard ATG | Optimized ATG | SpeedSTAR |
|---|---|---|---|
| Cycling conditions | 95° C./11 min<br>94° C./1 min<br>59° C./1 min ] ×28<br>72° C./1 min<br>60° C./45 min | 95° C./11 min<br>98° C./10 sec<br>59° C./45 sec ] ×28<br>72° C./30 sec<br>72° C./15 min | 95° C./1 min<br>98° C./4 sec<br>59° C./15 sec ] ×28<br>72° C./5 sec<br>72° C./1 min |
| Amplification time | 145.1 min | 71.67 min | 19.13 min |
| Signal Strength range [RFU] | 561-1655 | 600-3876 | 945-3669 |
| Stutter range | 4.18-11.16% | 3.91-13.77% | 6.49-13.56% |
| NTA range | 1.54-7.67% | 1.93-20.13% | 3.07-19.68% |
| PHR | 0.88-0.93% | 0.74-0.96% | 0.83-0.93% |

|  | PyroStart | KOD |
|---|---|---|
| Cycling conditions | 95° C./1 min<br>98° C./4 sec<br>59° C./20 sec ] ×28<br>12° C./30 sec<br>72° C./1 min | 95° C./2 min<br>98° C./4 sec<br>59° C./30 sec ] ×28<br>72° C./10 sec<br>72° C./1 min |
| Amplification time | 33.12 min | 29.47 min |
| Signal Strength range [RFU] | 751-3197 | 1091-3494 |
| Stutter range | 6.21-16.91% | 4.46-23.61% |
| NTA range | 3.01-23.09% |  |
| PHR | 0.71-0.94% | 0.61-0.94% |

The evaluated enzymes have reported extension rates ranging from approximately 15-200 nucleotides/second; in general, the reported extension rates are based on singleplex amplifications and may be somewhat lower for multiplex applications.

PCR conditions in tubes were initially investigated for these four enzymes with the goal of achieving full STR profiles in the least amount of time. For all reactions, 1 ng of human genomic DNA was amplified using primer pairs With respect to incomplete NTA, both SpeedSTAR and PyroStart as well as optimized TaqGold™ reactions exhibited levels that are up to three times higher than that of standard TaqGold™ reactions. For most alleles, levels fall below the 15% interpretation threshold. Those alleles having higher levels of incomplete NTA can be decreased to below the 15% interpretation threshold as discussed below. The KOD polymerase possesses 3'-5' exonuclease activity and does not generate fragments with A-overhangs; accordingly, all alleles were 1 nucleotide shorter than their allelic ladder counterpart.

The relative levels of stutter observed for optimized TaqGold™, SpeedSTAR and PyroStart reactions are similar to the range of stutter produced with standard TaqGold™ reactions; the range of stutter generated with KOD is slightly higher than the stutter for standard TaqGold™.

Example 4a

Fast PCR Protocol Using SpeedSTAR Polymerase in Tubes and Biochips

Based on the results presented above, the SpeedSTAR polymerase was selected for further evaluation in biochips with the goal of minimizing the total cycling time and achieving full STR profiles that satisfy signal strength, PHR, incomplete NTA and stutter interpretation requirements.

The time and temperature setpoints for amplification using SpeedSTAR in the microfluidic 16-sample biochip on the thermal cycler of the invention are 70 seconds 95° C. for hot-start activation followed by 28 cycles of 4 seconds at 95° C. for denaturation, 15 seconds at 59° C. for annealing, and 7 seconds at 72° C. for extension. A final extension of 90 seconds at 72° C. is performed for a total protocol time of 17.3 minutes. Tube reactions in the Eppendorf Mastercycler were performed in 19.13 minutes comprising of block times and temperatures set to an initial activation time of 1 minute at 95° C., 28 cycles of 4 seconds at 98° C., 15 seconds at 59° C. and 5 seconds at 72° C. followed by a final extension of 1 minute at 72° C.

Figure 4A:
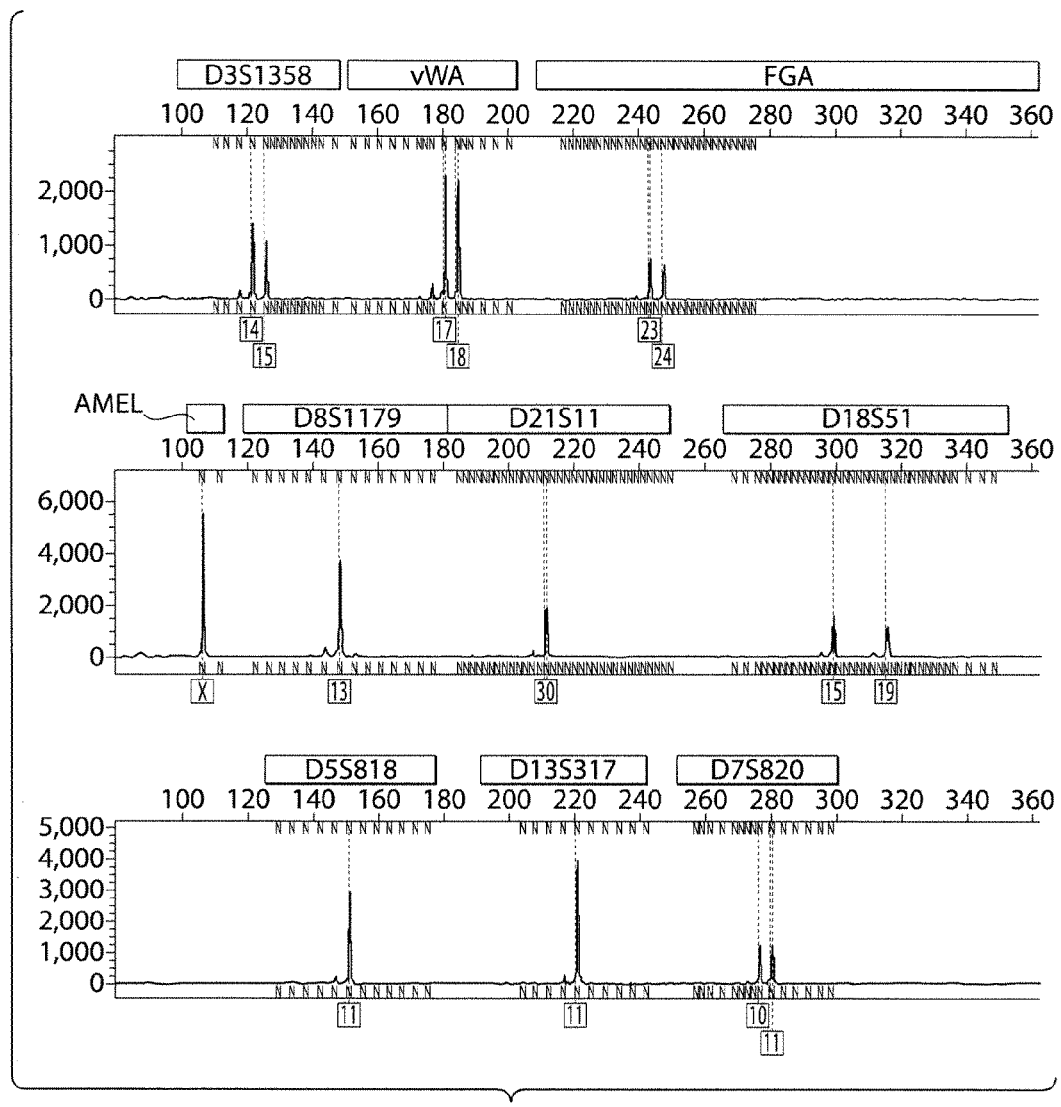
FIG. 4A is a graph showing the STR profile generated in biochip reactions according to the invention using 0.5 ng template DNA.
Figure 4B:
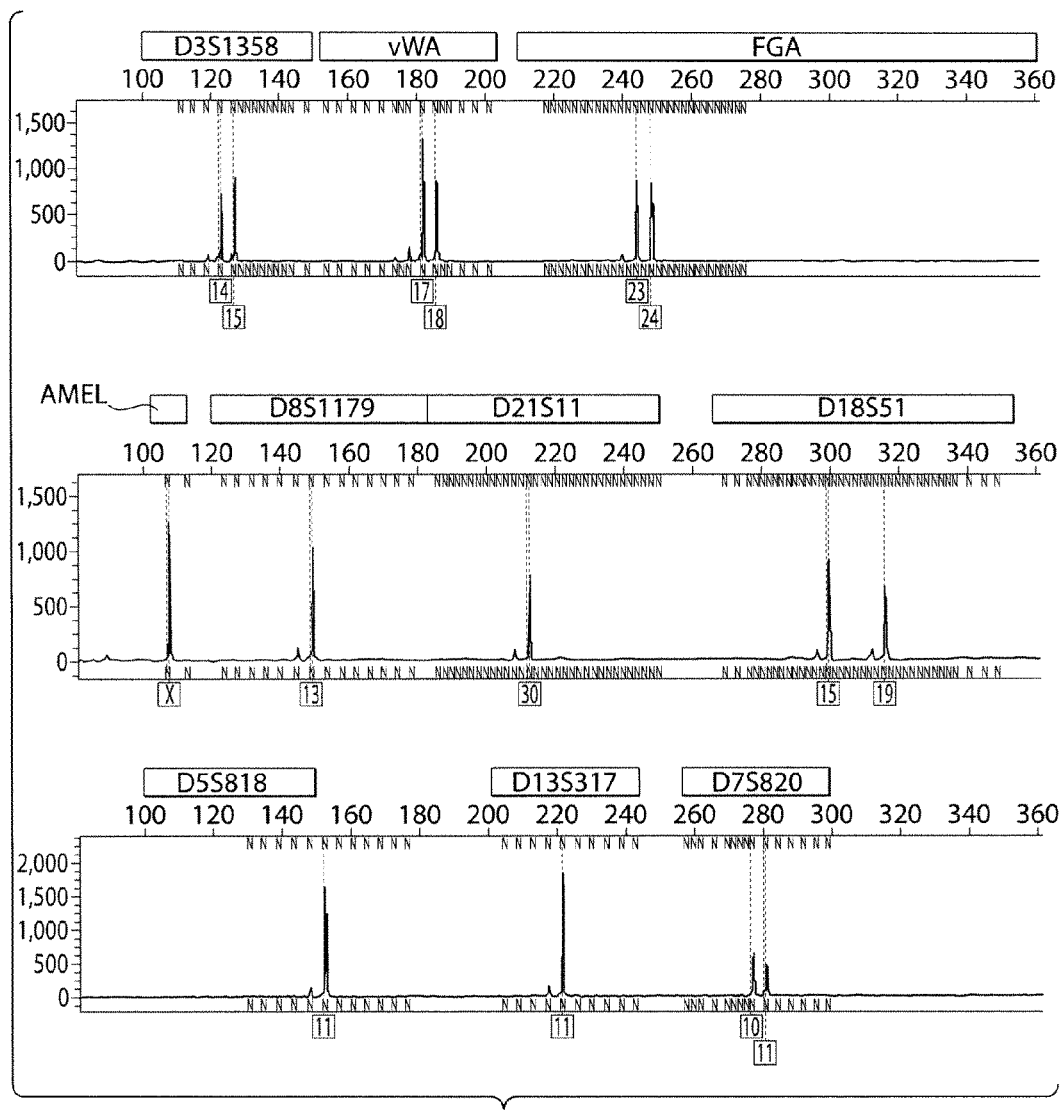
FIG. 4B is a graph showing the STR profile generated in tube reactions according to the invention using 0.5 ng template DNA.

FIGS. 4A and 4B show STR profiles generated with the preceding SpeedSTAR cycling conditions in (FIG. 4A) 7 µL biochip and (FIG. 4B) 10 µL, tube reactions using 0.5 ng of DNA and Table 2 presents signal strengths for all Profiler Plus ID alleles from the SpeedSTAR biochip and tube reactions as well as TaqGold™ in tubes using the standard protocol. Signal strengths of the 0.5 ng SpeedSTAR biochip reactions are on average approximately 2 times higher than those of the 1 ng standard TaqGold™ reactions, while the signal strengths of the 0.5 ng SpeedSTAR tube reactions are on average approximately the same as those of the TaqGold™ reactions.

TABLE 2

Comparison at signal strength. PHR, NTA and stutter for SpeedSTAR biochip and tube reactions and ATG standard reactions

| Locus | Allele | SpeedSTAR biochip reaction | | | | SpeedSTAR tube reaction | | | |
|---|---|---|---|---|---|---|---|---|---|
| | | Signal strength | PHR | NTA (%) | Stutter (%) | Signal strength | PHR | NTA (%) | Stutter (%) |
| D3S1358 | 14 | 1404.218 | 0.79 | 9.08 | | 727.11 | 0.81 | 9.74 | |
| D3S1358 | 15 | 1110.915 | | 8.05 | 10.35 | 895.12 | | 10.50 | 8.14 |
| vWA | 17 | 2338.633 | 0.95 | 6.14 | | 1346.81 | 0.65 | 6.62 | |
| vWA | 18 | 2216.64 | | 6.83 | 12.87 | 875.84 | | 6.78 | 11.96 |
| FGA | 23 | 747.5319 | 0.87 | 4.21 | | 877.22 | 0.96 | 2.54 | |
| FGA | 24 | 648.8992 | | 3.34 | 9.72 | 840.03 | | 2.30 | 8.32 |
| Amelogenin | X | 5645.423 | | 4.04 | | 1324.78 | | 2.02 | |
| D8S1179 | 13 | 3784.38 | | 5.62 | 10.70 | 1012.17 | | 5.47 | 11.56 |
| D21S11 | 30 | 2008.992 | | 3.15 | 13.05 | 787.70 | | 3.45 | 13.29 |
| D18S51 | 15 | 1655.991 | 0.70 | 6.90 | 11.44 | 924.04 | 0.72 | 5.48 | 9.09 |
| D18S51 | 19 | 1157.636 | | 9.53 | 14.13 | 683.76 | | 8.92 | 13.90 |
| D5S818 | 11 | 2904.473 | | 7.56 | 9.65 | 1608.46 | | 3.97 | 8.73 |
| D13S317 | 11 | 3906.373 | | 3.32 | 6.78 | 1867.38 | | 3.21 | 7.74 |
| D7S820 | 10 | 1232.908 | 0.93 | 7.23 | | 647.24 | 0.73 | 8.01 | |
| D7S820 | 11 | 1149.849 | | 10.16 | 7.37 | 469.59 | | 10.00 | 5.96 |

| | Standard ATG reactions | | | | | | | |
|---|---|---|---|---|---|---|---|---|
| | Signal strength | | PHR | | NTA (%) | | Stutter | |
| Locus | Average | STDEV | Average | STDEV | Average | STDEV | Average | STDEV |
| D3S1358 | 831.69 | 167.25 | 0.92 | 0.04 | 1.88 | 0.52 | | |
| D3S1358 | 802.99 | 141.78 | | | 1.54 | 0.34 | 5.31 | 0.23 |
| vWA | 765.61 | 83.69 | 0.90 | 0.08 | 4.22 | 0.44 | | |
| vWA | 736.85 | 88.40 | | | 4.23 | 0.19 | 7.38 | 0.48 |
| FGA | 735.41 | 130.32 | 0.93 | 0.05 | 2.14 | 0.45 | | |
| FGA | 727.02 | 122.82 | | | 1.98 | 0.44 | 7.19 | 0.43 |
| Amelogenin | 1655.65 | 343.77 | | | 3.35 | 0.49 | | |
| D8S1179 | 1405.57 | 105.18 | | | 4.52 | 0.58 | 6.51 | 0.62 |
| D21S11 | 1280.31 | 81.30 | | | 3.00 | 0.66 | 7.33 | 0.60 |
| D18S51 | 879.42 | 137.76 | 0.88 | 0.05 | 4.68 | 0.74 | 7.89 | 0.80 |
| D18S51 | 814.14 | 125.75 | | | 5.95 | 0.68 | 11.16 | 0.52 |
| D5S818 | 1599.08 | 223.78 | | | 3.71 | 0.17 | 4.94 | 0.44 |
| D13S317 | 1486.50 | 196.47 | | | 2.33 | 0.28 | 4.18 | 0.47 |
| D7S820 | 634.96 | 113.82 | 0.89 | 0.08 | 4.69 | 0.99 | | |
| D7S820 | 561.37 | 92.47 | | | 7.67 | 0.72 | 4.57 | 0.62 |

Example 4b

Allele Characterization of Fast PCR Using SpeedSTAR Polymerase in Tubes and Biochips In order to characterize the products of fast PCR reactions from Example 4a, quantification of PHR, incomplete NTA and stutter was performed. Biochip and tube reactions using the SpeedSTAR polymerase show more inter-locus peak height imbalance compared to that for the TaqGold™ reactions. The PHR for alleles generated in biochip reactions is between 0.70 and 0.95 and is approximately the same in tubes; all fall within acceptable interpretation guidelines. Reactions using SpeedSTAR have PHR that are approximately 10% lower than those determined for standard Taq-Gold™ reactions. Similarly, the level of incomplete NTA for most alleles in both biochip and tube reactions using Speed-STAR are approximately the same (2.0 and 10.6%); both are approximately 2 times higher than for TaqGold™ control reactions. The exception is incomplete NTA for the D3S1358 alleles, which is 4.8 to 7 times higher with SpeedSTAR than with TaqGold™; even in this case, the level of incomplete NTA is below 12% for the SpeedSTAR enzyme. Finally, the level of stutter in both biochip and tube based reactions using SpeedSTAR is between approximately 6.0 and 14.1%, on average approximately 1.6-fold higher than that for standard TaqGold™ tube reactions.

The microfluidic biochip reactions using 0.5 ng template DNA generate signal strengths that are approximately 2 times higher than those for standard TaqGold™ reactions using 1 ng template. This result suggests that the SpeedSTAR enzyme in the biochip and the TaqGold™ enzyme in the conventional reaction act with similar efficiencies; the DNA concentration in the biochip is approximately 1.8-fold that in the tube, which corresponds to the 2 fold greater in signal strength. In contrast, the fast tube based reactions are less efficient than the control TaqGold™ reactions; the approximately 40% reduction in product yield is likely the consequence of the poor cycling profile that results when commercial thermal cyclers are used for fast thermal cycling. Even in this circumstance, signal strengths are well over the levels required for interpretation and can be raised significantly by increasing the extension time by a few seconds per cycle (data not shown). Repeatability and reproducibility of the signal strength for fast PCR reactions in biochips and tubes are similar to those in conventional reactions.

The inter-locus allele signal strength for the fast biochip and tube reactions shows a higher level of imbalance as compared to the TaqGold™ reaction. The inter-loci signal strength balance is influenced by numerous factors including primer concentration, annealing temperature and time, and molecular weight of the loci. The STR amplification kit used for these experiments has a set of primer concentrations that are optimized for the TaqGold™ enzyme and the recommended cycling protocols. The signal strengths of the loci can be modified by adjusting the primer concentrations utilized in the amplification reactions (Henegariu et al., *Biotechniques* 1997, 23, 504-11).

The relationship between signal strength and template level for fast biochip and tube reactions is as expected with signal strength generally increasing with template. Good peak morphology is observed for all alleles at high template levels of 4 ng (which generate alleles with signal strengths of greater than 12000 RFU). At template levels of 0.03 ng and below some allele drop-out occurs. This effect is observed when amplification reactions are carried out with limited number of template DNA strands in the solution leading to stochastic amplification (Walsh et al., *PCR Methods Appl.* 1992, 1, 241-250). The presence of readily detectable signal for both the high-signal strength alleles and low-signal strength alleles at a template level of 0.006 ng, demonstrates the high sensitivity of the fast biochip and tube reaction coupled with Genebench-FX™ Series 100 separation and detection, demonstrating the utility of this system for low copy number analysis. Taken together, this data also suggests that the fast PCR approach and the thermal cycler of the invention and Genebench instrumentation have a high template dynamic range.

Example 4c

DNA Template Levels and Allele Characteristics in Fast PCR Reactions

Figure 5A:
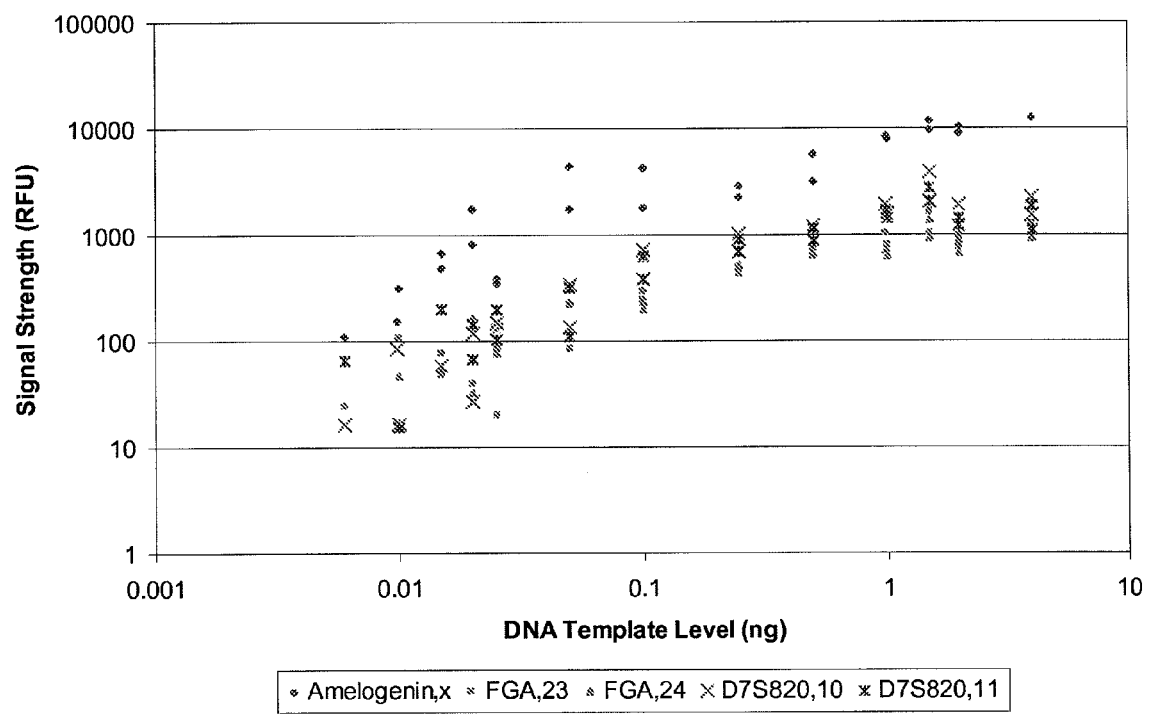
FIG. 5A is a graph showing the effect of DNA template level on signal strength in biochip reactions.
Figure 5B:
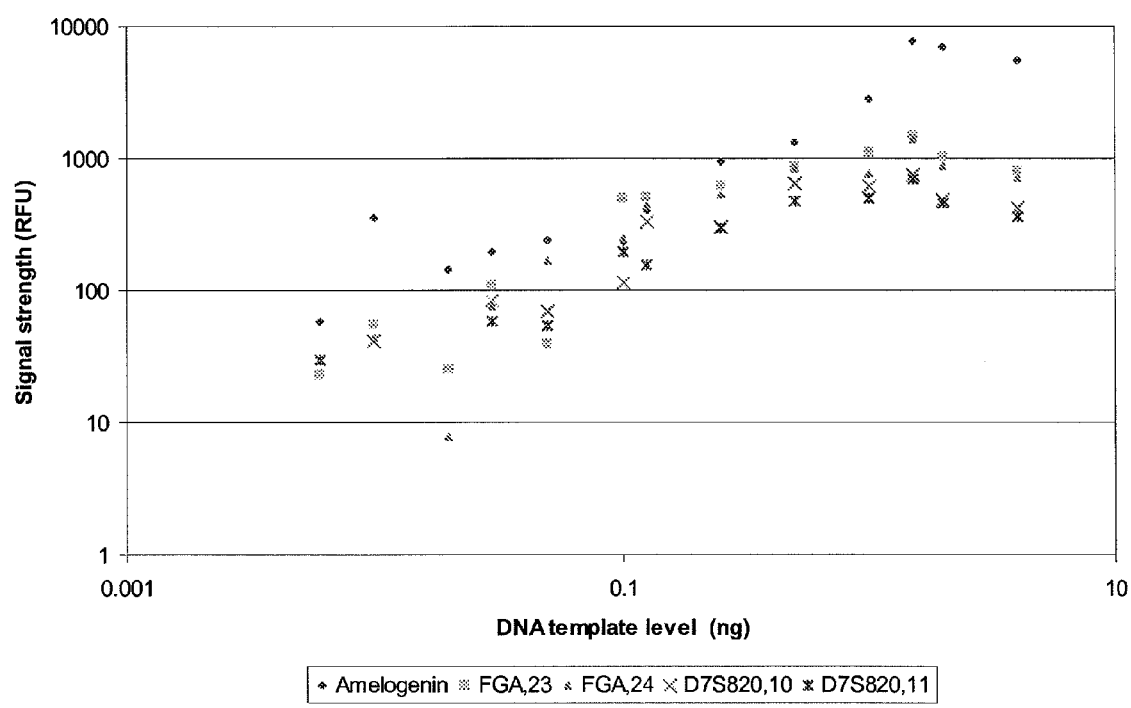
FIG. 5B is a graph showing the effect of DNA template level on signal strength in tube reactions.

The effects of template DNA on signal strength for fast PCR reactions using SpeedSTAR polymerase in (FIG. 5A) biochip and (FIG. 5B) tube reactions are presented in FIGS. 5A and 5B. The alleles selected for analysis were Amelogenin, the allele with the highest signal level in the STR profile and FGA 23 and 24 and D7S820 10 and 11, the alleles with the lowest signal levels in the profile. Signal strengths for all alleles increase as the DNA template level increases from 0.006 ng to 4 ng in both SpeedSTAR biochip and tube reactions. At a template level of 0.006 ng, signal strengths for the amelogenin peak of 111 RFU for biochip and 58 RFU for tube reactions were observed. At a template level of 4 ng, signal strengths of 12680 RFU were seen for biochip and 5570 RFU for tube reactions. All alleles observed in both reaction types showed good peak morphology.

Figure 6A:
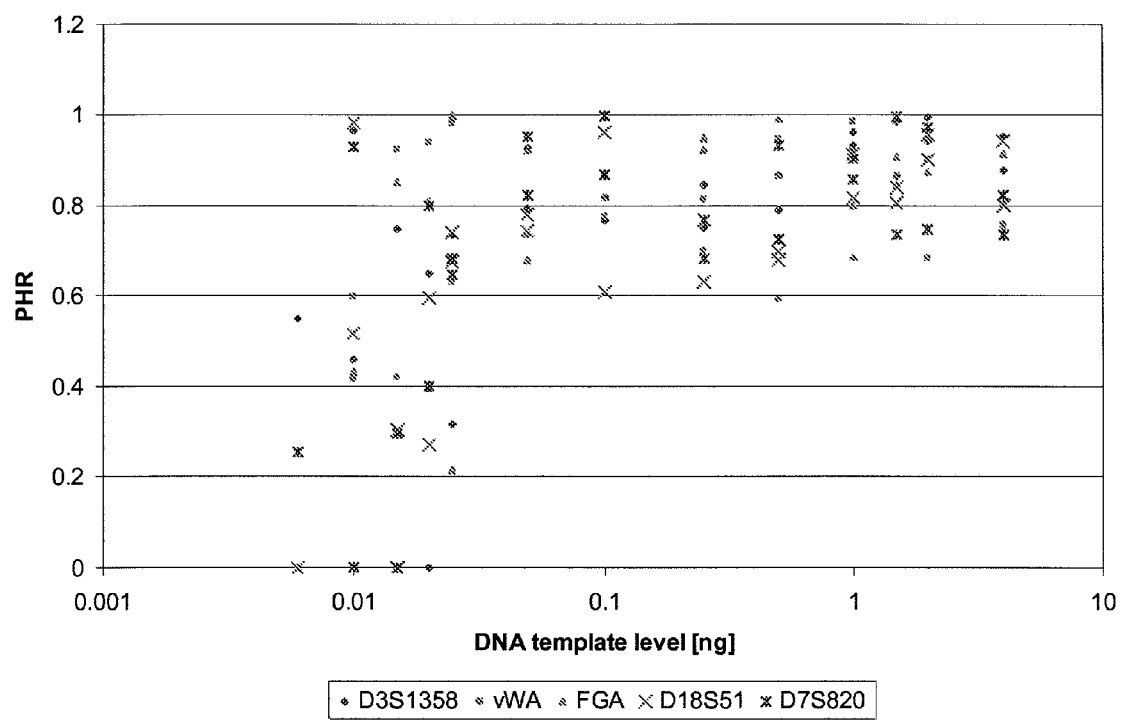
FIG. 6A is a graph showing the effect of DNA template level on heterozygous peak height ratio (PHR) in biochip reactions.
Figure 6B:
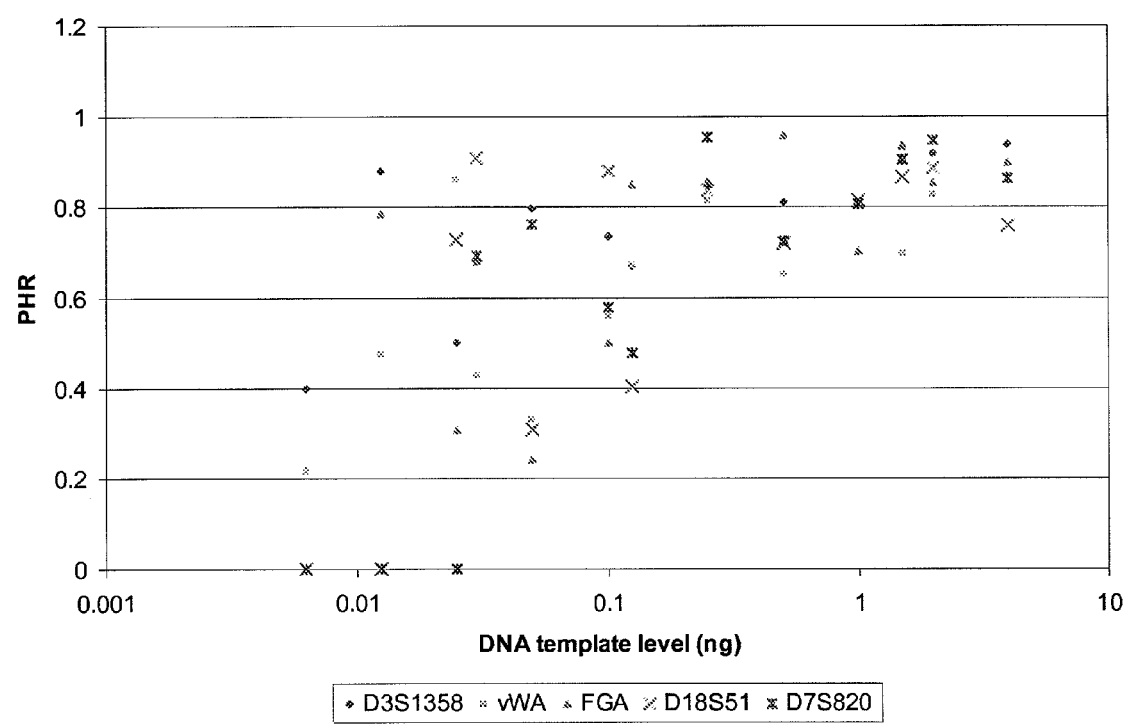
FIG. 6B is a graph showing the effect of DNA template level on PHR in tube reactions.

For fast biochip reactions (FIG. 6A), PHR is between 0.6 and 1.0 for template levels ranging from 0.05 to 4.0 ng. For template levels below 0.05 ng, PHR decreases until 0.025 ng, when instances of allelic dropouts occur and PHR of zero are observed. Similar results are observed for fast tube reactions, although they generally exhibit somewhat lower PHR than biochips reactions (FIG. 6B). For biochip reactions, the level of incomplete NTA is 15% or less for template levels of 2.0 ng and below. For tube reactions, the incomplete NTA levels surpass 15% at template levels of 1 ng and increase dramatically by 4 ng.

Figure 7A:
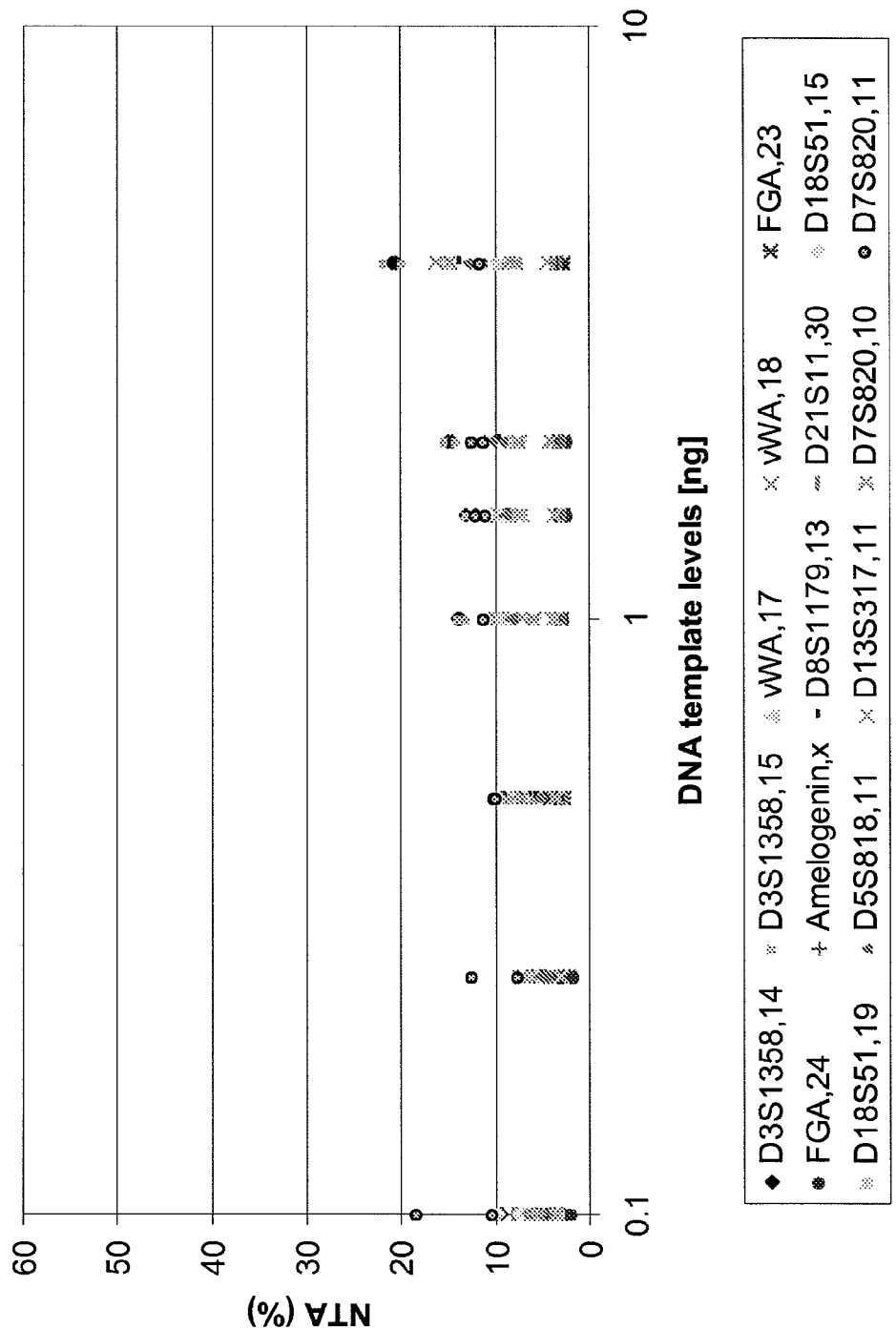
FIG. 7A is a graph showing the effect of DNA template level on non-template nucleotide addition (NTA) in biochip reactions.
Figure 7B:
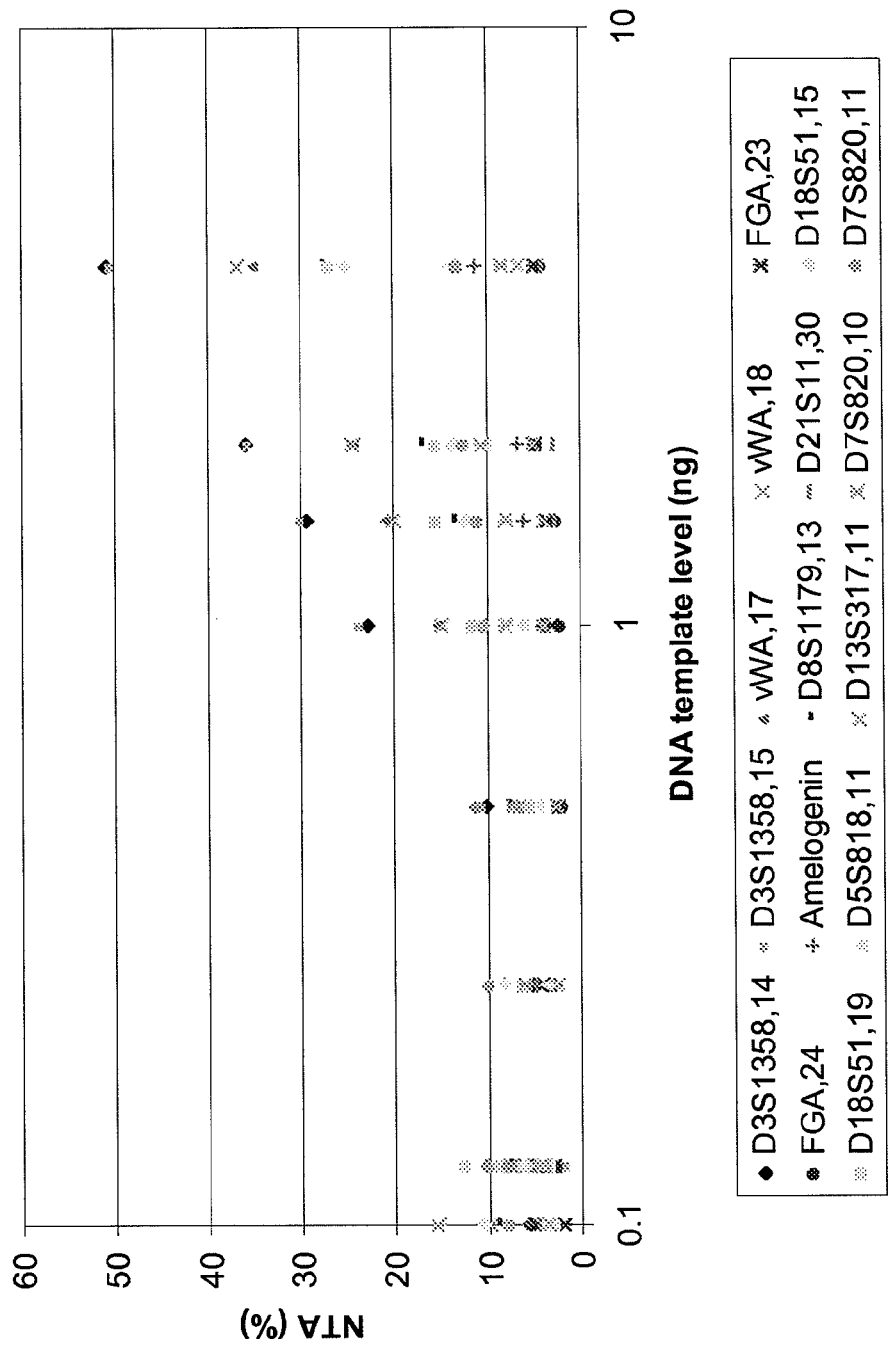
FIG. 7B is a graph showing the effect of DNA template level on NTA in tube reactions
Figure 8A:
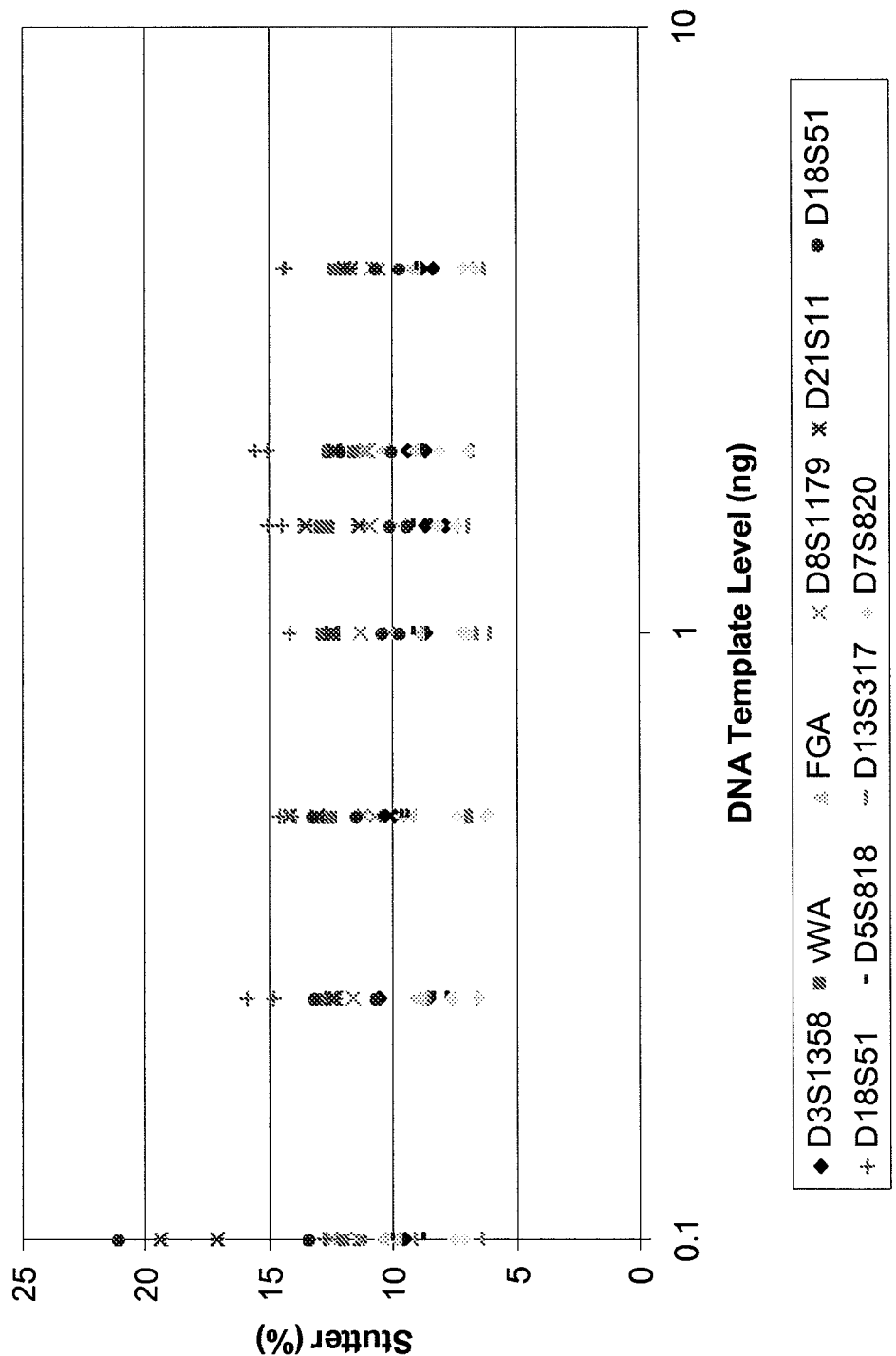
FIG. 8A is a graph showing the effect of DNA template level on stutter in biochip reactions.
Figure 8B:
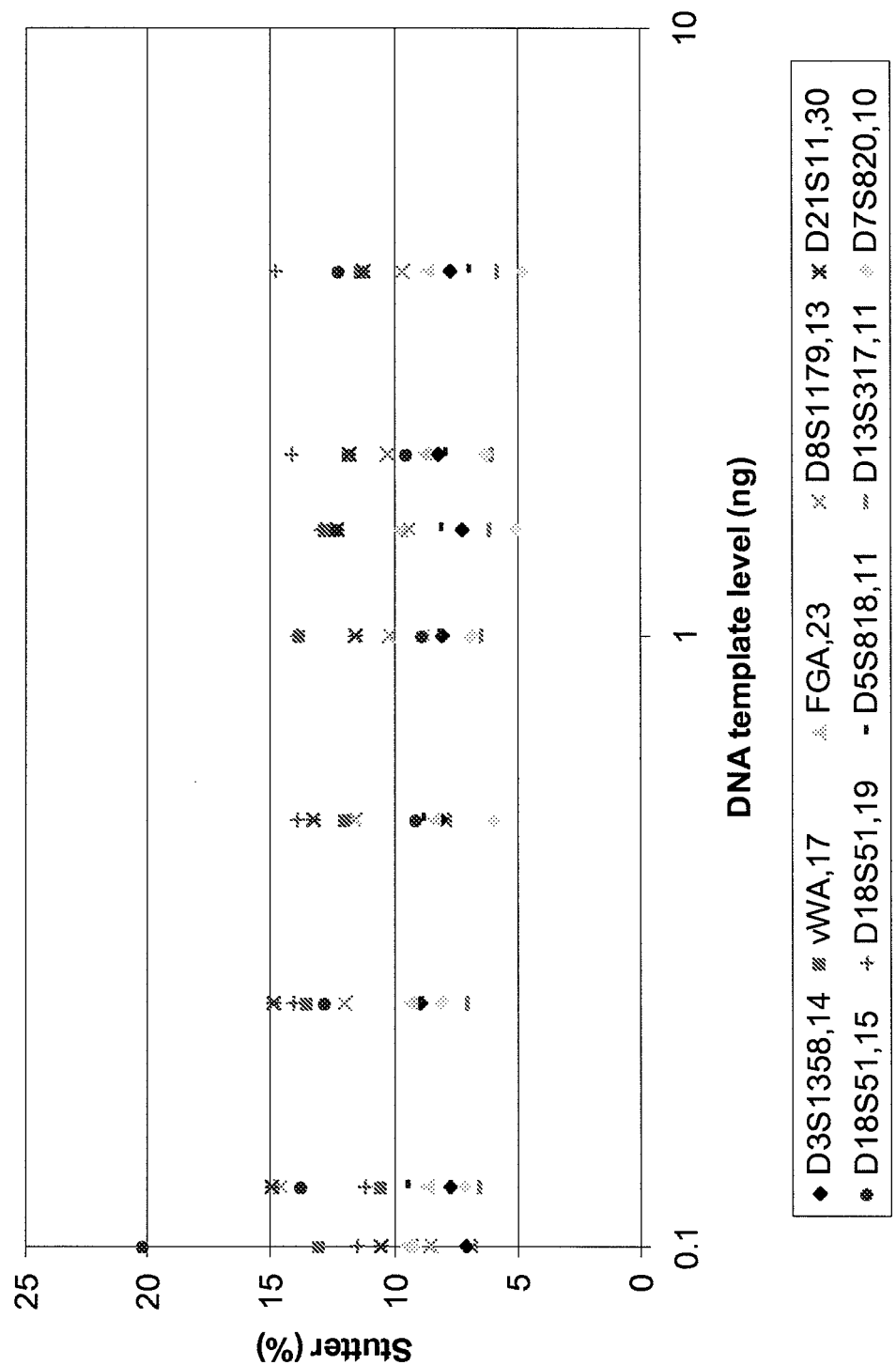
FIG. 8B is a graph showing the effect of DNA template level on stutter in tube reactions

Two major differences between biochip and tube reactions are the temperature profiles of the reaction solutions and the relative concentration of template and polymerase. The level of incomplete NTA decreases as more polymerase is available. For biochip reactions experimental data show that over a DNA template range from 0.5-4.0 ng the level of incomplete NTA decreases by approximately 50% as the amount of SpeedSTAR polymerase increases from 0.3 U to 1.2 U (FIGS. 7A and 7B). The level of stutter for fast biochip and tube reactions was relatively constant and generally less than 15% for all alleles over a template level range of 0.25-4.0 ng (FIGS. 8A and 8B).

The speed of an STR amplification reaction is only relevant if the reaction itself generates actionable data that meets forensic interpretation guidelines. The FBI has general guidelines that are used for STR interpretation, and individual laboratories set thresholds that must be met before a profile can be considered acceptable based on their validation work (Holt et al., *J. Forensic Sci.* 2002, 47(1), p. 66-96; LaFountain et al., *J. Forensic Sci.*, 2001, 46(5), 1191-8).

The conditions presented herein can generate fast STR profiles that meet these guidelines. PHR for 0.5 ng template in biochip and tube reactions meet with the interpretation guidelines that state a level of 0.6 or greater is required and are consistent with previously reported results (Leclair et al., *J. Forensic Sci.* 2004, 49, 968-80). For higher DNA template amounts, PHR remain relatively constant but are lower than those for the 1 ng TaqGold™ reactions. For low copy numbers, the PHR is dominated by amplification due to stochastic fluctuations.

The level of incomplete NTA is based on the ability of the polymerase to fully adenylate all STR amplicons. For conventional amplification, this is accomplished by attaching a "pigtail" to the primer and increasing the final extension time. The level of incomplete NTA for 0.5 ng biochips and tube reactions described herein are within interpretation guidelines.

Levels of incomplete NTA increase with increasing DNA template (a consequence of the increasing ratio of DNA to polymerase) and can be reduced by increasing the amount of polymerase, extension time per cycle, and final extension time. The later two approaches are not well-suited to fast interpretational guidelines and are also consistent with previously cited reports. As expected, the level of stutter appears to be independent of the DNA template level.

Example 4d

Repeatability and Reproducibility Studies

The repeatability and reproducibility of the fast biochip (Table 3A) and tube (Table 3B) reactions using the Speed-STAR polymerase were evaluated by performing 24 identical PCR reactions in 3 PCR biochips and by performing 5 identical tube reactions. For biochip reactions, the confidence value (CV) for signal strength ranges from 17 to 24% and for tube reactions from 15 to 34%. The CV for standard TaqGold™ reactions is between 6 and 21%.

TABLE 3

Reproducibility of SpeedSTAR biochip (3A) and tube (3B) reactions

| Allele | Signal Strength (RFU) | | | | PHR | | | | NTA (%) | | | | Stutter (%) | | | |
|---|---|---|---|---|---|---|---|---|---|---|---|---|---|---|---|---|
| | Average | STDEV | Max | Min | Average | STDEV | Max | Min | Average | STDEV | Max | Min | Average | STDEV | Max | Min |
| A: SpeedSTAR biochip reactions | | | | | | | | | | | | | | | | |
| D3S1358, 14 | 1235.40 | 271.43 | 1963.95 | 781.79 | 0.85 | 0.11 | 1.00 | 0.63 | 9.11 | 1.77 | 11.86 | 6.64 | | | | |
| D3S1358, 15 | 1066.65 | 251.75 | 1793.70 | 689.23 | | | | | 8.97 | 1.80 | 12.08 | 6.53 | 8.78 | 0.63 | 9.84 | 7.67 |
| vWA, 17 | 2765.49 | 551.47 | 3818.46 | 1732.31 | 0.81 | 0.12 | 0.98 | 0.56 | 6.19 | 1.27 | 8.25 | 4.76 | | | | |
| vWA, 18 | 2274.33 | 398.37 | 3197.88 | 1379.49 | | | | | 6.22 | 1.34 | 8.29 | 4.71 | 12.95 | 0.66 | 14.35 | 11.78 |
| FGA, 23 | 884.74 | 153.51 | 1276.87 | 620.51 | 0.84 | 0.11 | 0.99 | 0.61 | 2.51 | 0.58 | 3.51 | 1.03 | | | | |
| FGA, 24 | 794.52 | 176.07 | 1109.30 | 376.41 | | | | | 2.68 | 0.48 | 3.52 | 1.71 | 10.10 | 0.95 | 12.18 | 8.63 |
| AMEL | 5085.29 | 1138.51 | 7276.15 | 3271.82 | | | | | 3.70 | 0.40 | 4.54 | 3.01 | | | | |
| D8S1179, 13 | 3787.27 | 778.68 | 5700.08 | 2420.29 | | | | | 7.35 | 0.74 | 8.82 | 6.17 | 10.96 | 0.53 | 12.08 | 10.01 |
| D21S11, 30 | 1914.04 | 424.28 | 2725.91 | 1005.45 | | | | | 2.91 | 0.61 | 4.14 | 2.04 | 12.74 | 0.85 | 14.44 | 10.73 |
| D18S51, 15 | 2248.76 | 429.94 | 3056.15 | 1475.43 | | | | | 5.80 | 2.08 | 7.99 | 0.00 | 10.61 | 0.64 | 11.54 | 9.04 |
| D18S51, 19 | 1843.92 | 358.13 | 2549.69 | 1271.08 | 0.83 | 0.10 | 0.99 | 0.59 | 5.90 | 2.23 | 8.19 | 0.00 | 14.52 | 0.85 | 16.64 | 12.96 |
| D5S818, 11 | 2734.70 | 500.56 | 3846.65 | 1629.74 | | | | | 9.04 | 1.88 | 12.07 | 6.34 | 8.90 | 0.33 | 9.89 | 8.35 |
| D13S317, 11 | 4097.95 | 701.10 | 5279.96 | 2724.10 | | | | | 3.02 | 0.85 | 6.39 | 2.25 | 6.87 | 0.42 | 7.95 | 6.09 |
| D7S820, 10 | 1877.24 | 384.59 | 3262.80 | 1397.95 | 0.84 | 0.09 | 1.00 | 0.69 | 6.68 | 0.60 | 7.67 | 5.67 | | | | |
| D7S820, 11 | 1594.27 | 309.99 | 2336.39 | 1124.30 | | | | | 10.60 | 0.68 | 11.81 | 9.19 | 7.26 | 0.47 | 7.99 | 6.42 |
| | CV Min: 17% | | | | CV Min: 11% | | | | CV Min: 6% | | | | CV Min: 4% | | | |
| | CV Max: 24% | | | | CV Max: 14% | | | | CV Max: 28% | | | | CV Max: 9% | | | |
| B: SpeedSTAR tube reactions | | | | | | | | | | | | | | | | |
| D3S1358, 14 | 1718.86 | 464.62 | 2321.62 | 1249.71 | 0.86 | 0.08 | 0.94 | 0.74 | 19.51 | 0.44 | 20.04 | 18.84 | | | | |
| D3S1358, 15 | 1455.28 | 285.03 | 1719.04 | 1110.96 | | | | | 19.68 | 0.78 | 20.71 | 18.56 | 8.34 | 0.49 | 8.88 | 7.65 |
| vWA, 17 | 1934.44 | 299.00 | 2150.18 | 1483.24 | 0.83 | 0.11 | 0.98 | 0.71 | 12.12 | 0.22 | 12.32 | 11.75 | | | | |
| vWA, 18 | 1722.47 | 450.99 | 2439.38 | 1257.89 | | | | | 12.04 | 0.27 | 12.29 | 11.65 | 12.72 | 0.50 | 13.37 | 12.18 |
| FGA, 23 | 1625.37 | 289.29 | 2020.33 | 1275.75 | 0.91 | 0.08 | 0.99 | 0.80 | 3.57 | 0.21 | 3.84 | 3.28 | | | | |
| FGA, 24 | 1561.32 | 346.77 | 2003.50 | 1185.22 | | | | | 3.07 | 0.21 | 3.30 | 2.75 | 9.57 | 0.53 | 10.22 | 8.90 |
| AMEL | 3669.80 | 844.56 | 4967.47 | 2799.39 | | | | | 5.02 | 0.27 | 5.41 | 4.68 | | | | |
| D8S1179, 13 | 2447.48 | 658.60 | 3268.31 | 1820.49 | | | | | 8.20 | 0.40 | 8.61 | 7.58 | 10.47 | 0.45 | 10.86 | 9.72 |
| D21S11, 30 | 1628.98 | 436.18 | 2147.27 | 1222.17 | | | | | 4.85 | 0.33 | 5.26 | 4.46 | 11.78 | 0.28 | 12.14 | 11.54 |
| D18S51, 15 | 1603.23 | 545.46 | 2261.97 | 1066.52 | 0.79 | 0.17 | 0.95 | 0.61 | 8.30 | 0.34 | 8.67 | 7.91 | 9.67 | 0.31 | 10.09 | 9.30 |
| D18S51, 19 | 1296.20 | 434.98 | 2043.27 | 963.18 | | | | | 8.79 | 0.99 | 10.49 | 7.91 | 13.56 | 0.88 | 14.69 | 12.28 |
| D5S818, 11 | 3412.10 | 894.75 | 4629.47 | 2506.84 | | | | | 6.27 | 0.17 | 6.47 | 6.02 | 8.38 | 0.31 | 8.86 | 8.03 |
| D13S317, 11 | 3093.19 | 749.20 | 3987.13 | 2204.34 | | | | | 3.94 | 0.14 | 4.16 | 3.81 | 6.49 | 0.25 | 6.86 | 6.25 |
| D7S820, 10 | 1009.46 | 228.75 | 1297.92 | 780.76 | 0.93 | 0.03 | 0.98 | 0.90 | 7.86 | 0.65 | 8.55 | 6.86 | | | | |
| D7S820, 11 | 945.50 | 208.75 | 1228.39 | 705.49 | | | | | 12.13 | 1.53 | 14.38 | 10.56 | 6.52 | 0.34 | 7.02 | 6.15 |
| | CV Min: 15% | | | | CV Min: 3% | | | | CV Min: 2% | | | | CV Min: 2% | | | |
| | CV Max: 34% | | | | CV Max: 21% | | | | CVMax: 13% | | | | CV Max: 6% | | | | multiplexed amplification, as they increase the reaction time. Increasing polymerase concentration is effective and compatible with fast PCR. Stutter is a result of DNA strand slippage during extension (Walsh et al., *Nucleic Acids Res.* 1996, 24(14), 2807-12). The level of stutter described here for the 0.5 ng biochip and tube reactions fall within the The CV for PHR is up to 14% for biochips and 21% for tube reactions, compared to the 5% to 10% range observed for standard TaqGold™ reactions. CVs for incomplete NTA in biochip reactions vary between 6% and 28%, and for tube reactions between 2 to 13%. Again, these variations are similar to the 4 to 28% range observed for standard Taq- Gold™ reactions. The CVs for stutter in biochips are 4 to 9%, in tubes 2 to 6%, and are also similar to the range of 4-13% observed for standard TaqGold™ reactions.

Example 4e

Compatibility with Other Commercially Available STR Kits

Figure 9A:
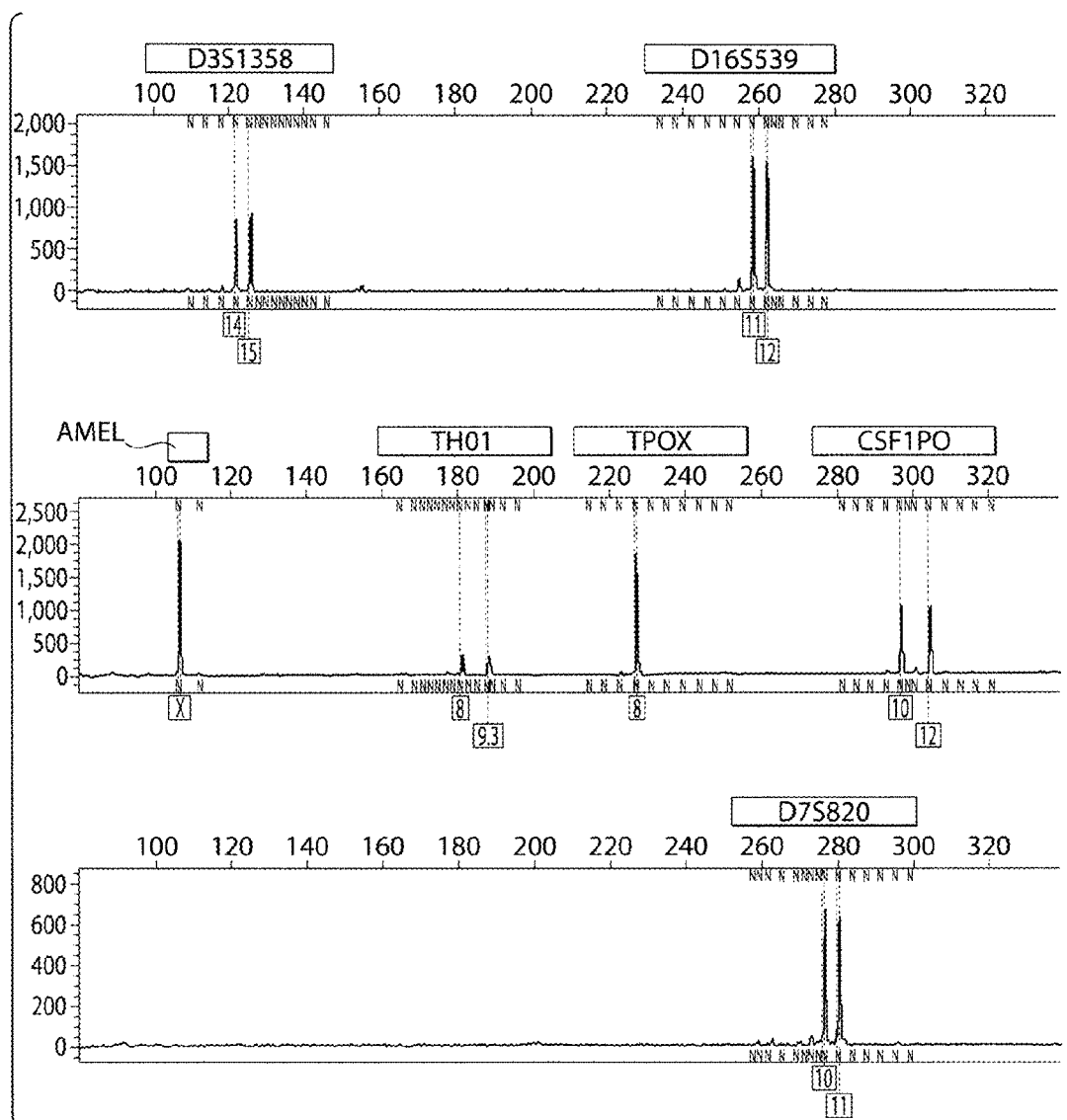
FIG. 9A is a graph showing the profile for biochip generated with the COfiler™ primer set using 1 ng template DNA.
Figure 9B:
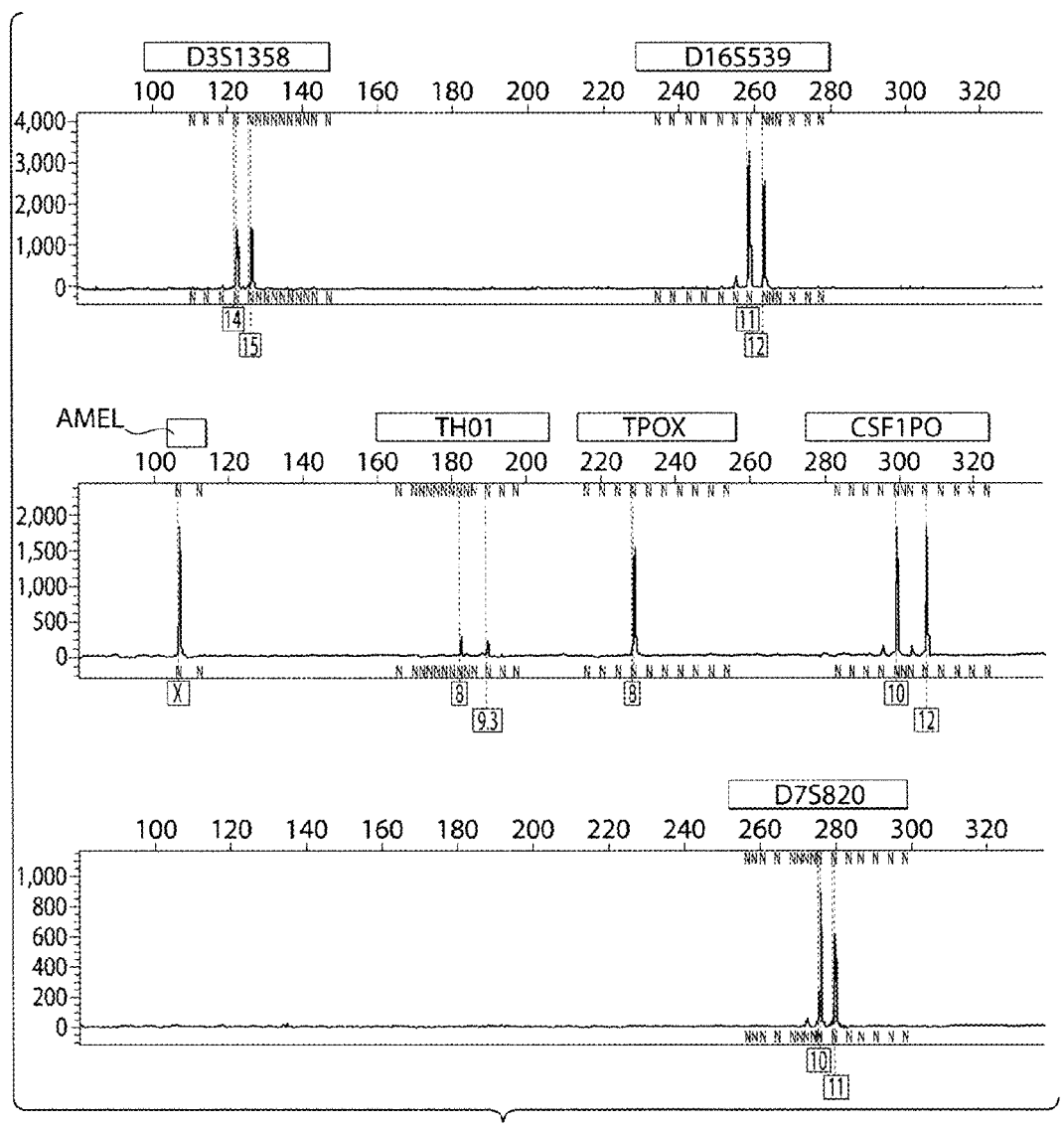
FIG. 9B is a graph showing the profile for a tube reaction generated with the COfiler™ primer set using 1 ng template DNA.
Figure 9C:
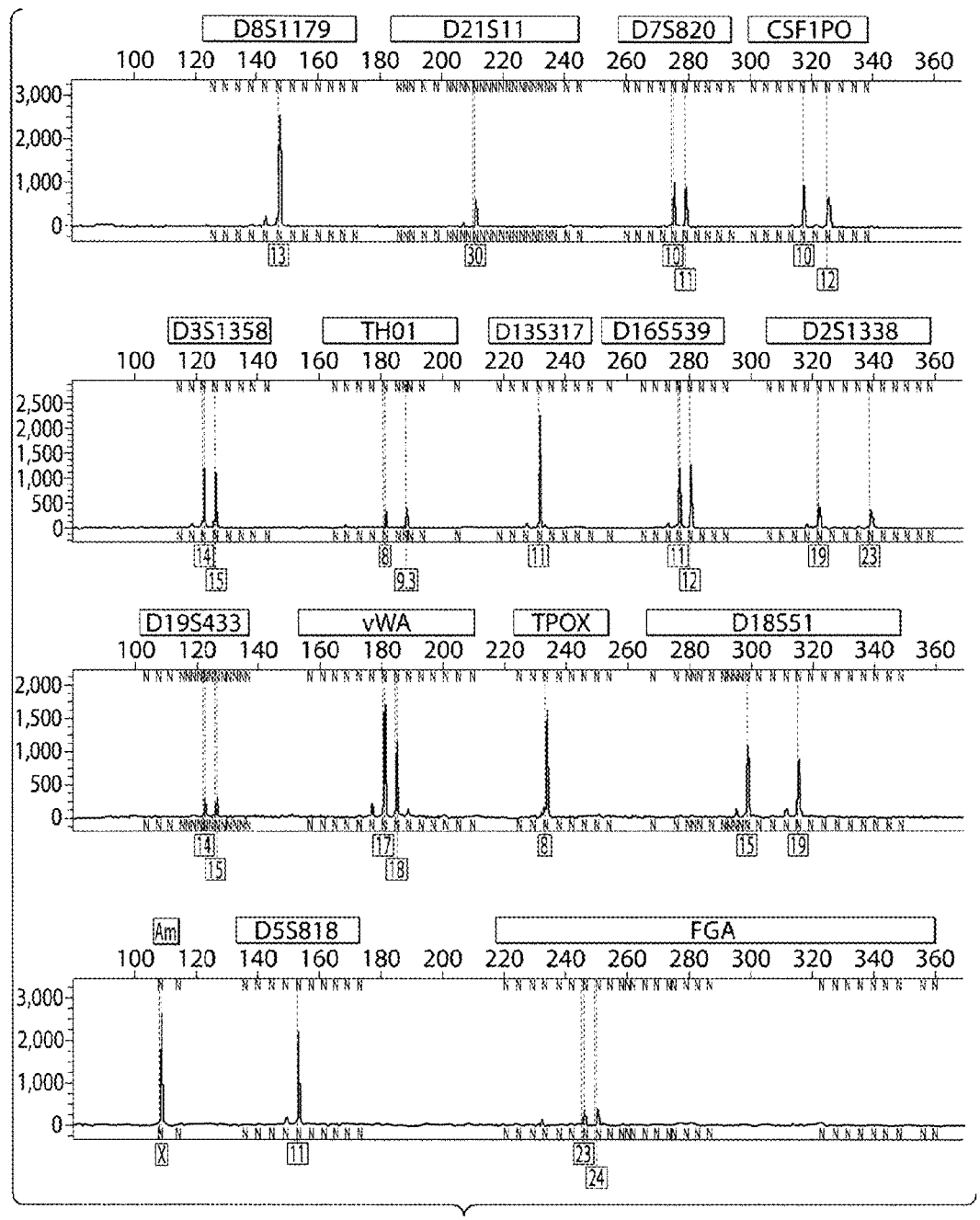
FIG. 9C is a graph showing the profile for biochip generated with the Identifiler™ primer set using 1 ng template DNA.
Figure 9D:
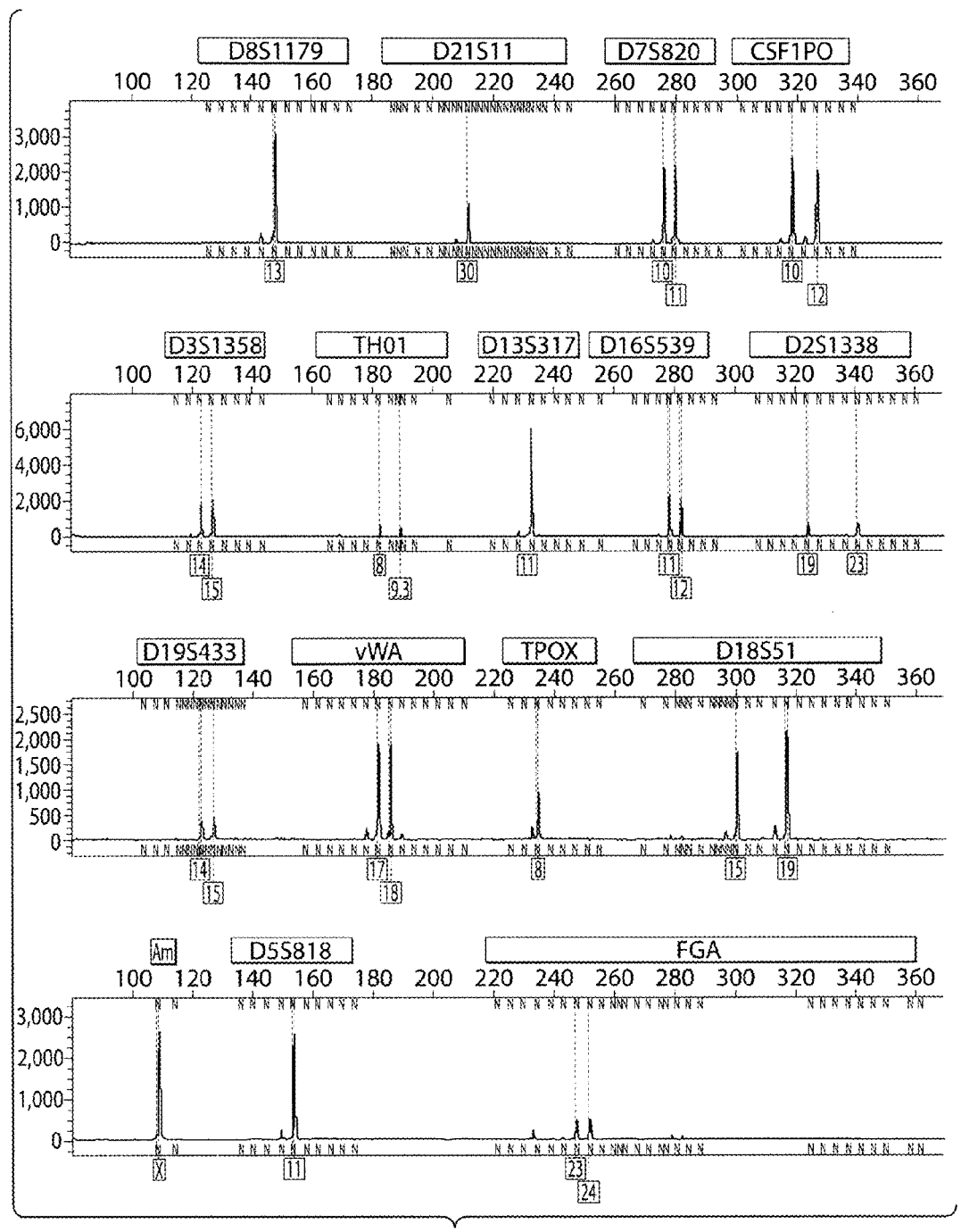
FIG. 9D is a graph showing the profile for a tube reaction generated with the Identifiler™ primer set using 1 ng template DNA.

Using the same fast biochip and tube conditions described above, a series of samples were evaluated using primer sets from the COfiler™ and Identifiler™ kits. FIGS. 9A and 9B show the achievement of full profiles using these primer sets using the thermal cycler of the invention, the SpeedSTAR enzyme, and the protocols described herein. Each is suitable for these commercially available kits as well. Although full profiles were achieved, imbalance in the signal strengths across the loci was observed.

Example 5

Fast Sequencing with the Thermal Cycler

The thermal cycling instrument and methodology can also be applied to fast DNA sequencing reactions. In this implementation of the fast thermal cycler, the instrumentation and biochip are the same as that used for PCR. Different reaction solutions, polymerase and cycling temperatures are applied for the sequencing reaction. The currently commercially available sequencing reactions take 49 min (for GE Amersham DYEnamic™ ET Terminato Cycle Sequencing Kit) and 2.25 hr (for AB Big Dye V3.1. Utilizing the NetBio thermal cycler, with conventional reagents, allowed the sequencing reaction time to be reduced to 21 minutes.

Fast sequencing has been achieved using the thermocycler disclosed herein and biochip comprising 16 lanes. The final reaction volume in the chips was 7 µL. Half strength sequencing reactions were set up with the DYEnamic™ ET Terminator Cycle Sequencing Kit from GE Healthcare following the manufacturer's protocol. All volumes were scaled down accordingly to accommodate the 7 µL, final volume. Template for the reaction was 0.1 pmol B. subtilus with a fragment size of 343 bp.

Figure 10:
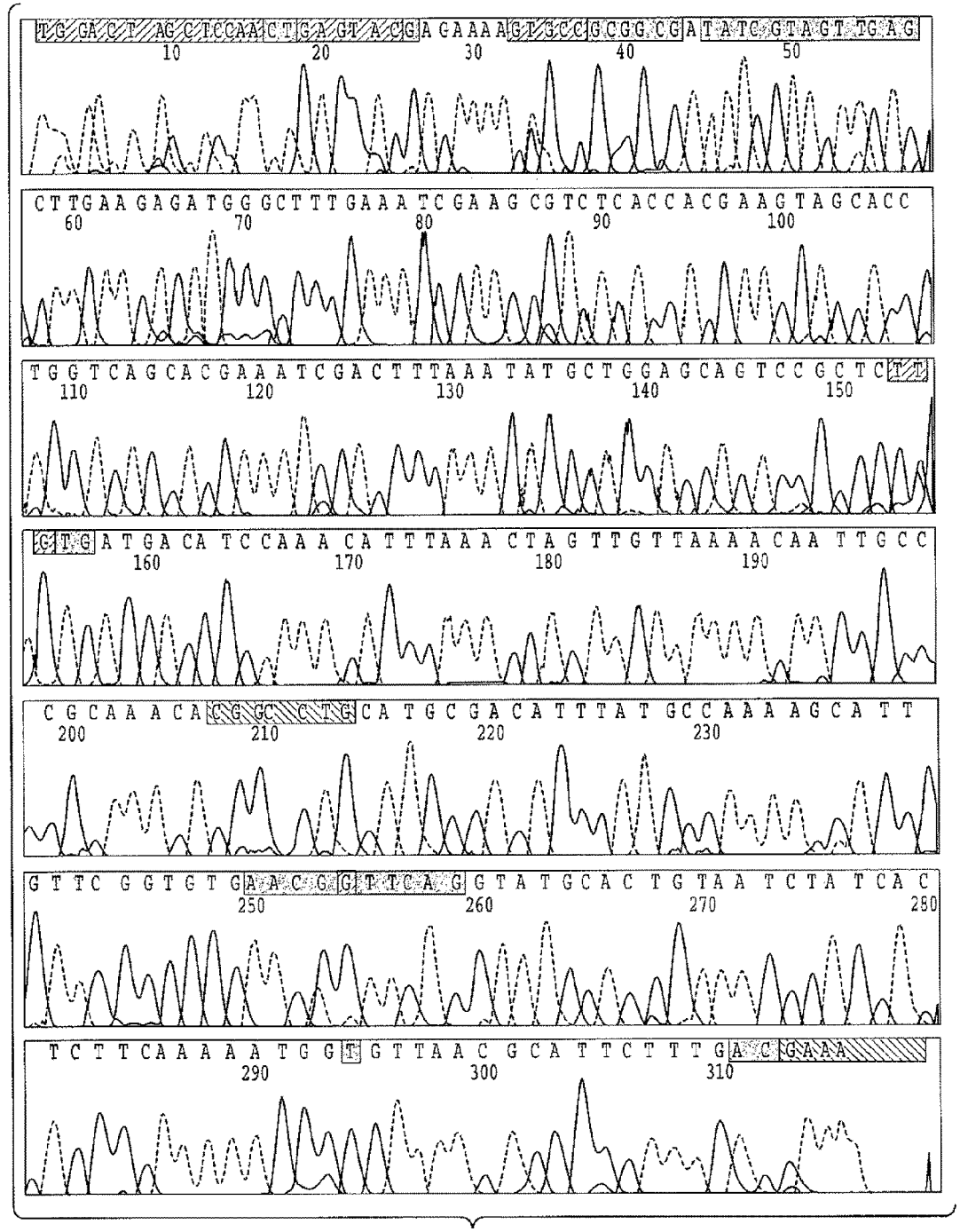
FIG. 10 is a graph showing the profile for an embodiment of a sequencing reaction, as described in Example 5.
Figure 11:
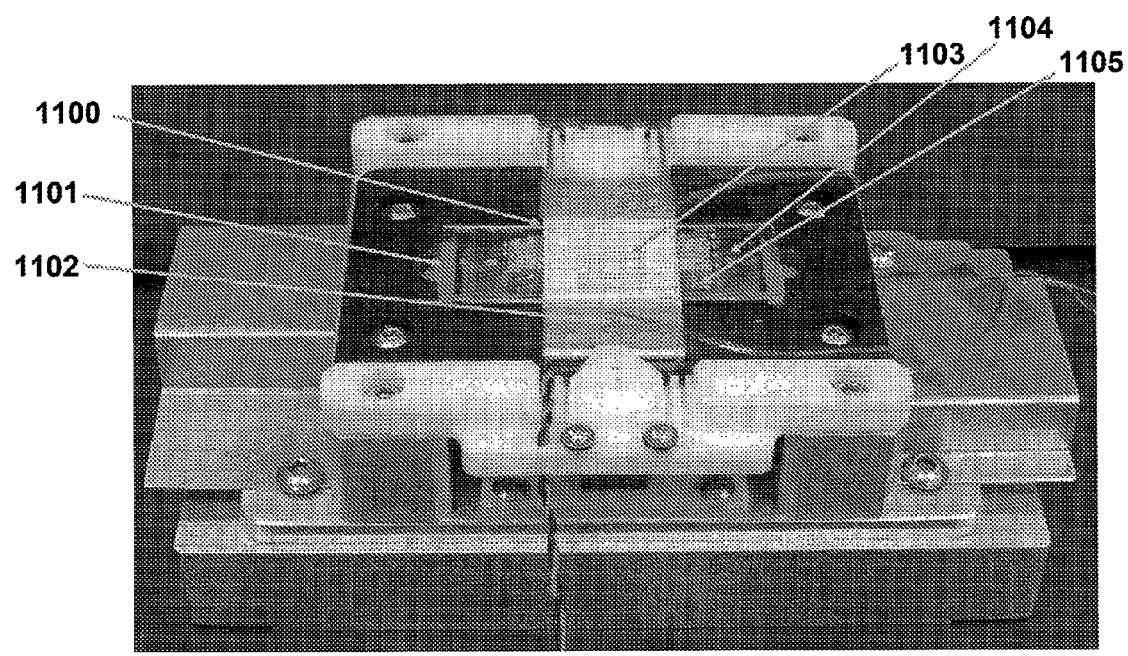
FIG. 11 shows a view from above a thermal cycler comprising a TCE (1100), biochip (1101), thermosensor (1102), thermoelectric cooler (1103), heat sink (1104), and heat sink thermosensor (1105), where the chip compression element has been removed for clarity.

Three cycling protocols were demonstrated with the first protocol consisting of 30 cycles of (20 s at 95° C., 15 s at 50° C. and 60 s at 60° C.) (total cycling time is 51.7 min), the second protocol consisting of 30 cycles of 5 s at 95° C., 15 s at 50° C. and 30 s at 60° C. (total cycling time is 29 min) and a third protocol consisting of 30 cycles of 5 s at 95° C., 10 s at 50° C. and 20 s at 60° C. (total cycling time of 21.6 min). Each sequencing reaction was cleaned-up with ethanol precipitated, and separated on Genebench FX Series 100. The average PHRED scores for sequencing a 343 bp PCR product for the 3 cycling protocols were 282, 287, and 279 respectively; demonstrating that sequencing of a 343 bp product can be achieved in chip in less than 22 min. FIG. 10 shows the DNA sequence of the fast DNA sequencing protocol.

In general, biochip based multiplexed amplification of one or more nucleic acids utilizing the systems and methods described herein have the advantage of providing amplified nucleic acid products in significantly shorter overall reaction times with respect to reactions run in thin-walled tubes and utilizing presently commercialized thermal cycling units.

The invention claimed is:

1. A method for simultaneously amplifying of a plurality of loci in a nucleic acid solution comprising:

providing in single solutions contained in a plurality of reaction chambers located in a biochip, samples having at least ten and up to 250 target nucleic acid loci to be amplified, with at least ten and up to 250 different primer pairs, each primer pair hybridizing to one of the at least ten and up to 250 loci to be amplified, said solution further comprising:
(i) one or more buffers;
(ii) one or more salts;
(iii) a nucleic acid polymerase; and
(iv) nucleotides; and
providing a TCE, comprising a means for heating and cooling, at least one thermosensor, a controller that receives signals from said at least one thermosensor and a power supply, said at least one thermosensor positioned and configured to measure the effective temperature of each of the single solutions in the reaction chambers of the biochip and to provide feedback to the TCE to heat or cool the solution to set or maintain the solution at a desired temperature;
simultaneously amplifying said plurality of loci by using the at least one thermosensor, the controller and the TCE to sequentially thermally cycle the temperature of the nucleic acid solution in each reaction chamber between a denaturing state, an annealing state, and an extension state for a predetermined number of cycles at heating and cooling rates of about 4-150° C./sec, and minimizing the transition times between the extension, denaturation, and annealing states to yield a plurality of amplified loci in each reaction chamber in 97 minutes or less.

2. The method of claim 1, further comprising:
holding the a plurality of reaction solutions at a final state to provide one or a plurality of amplified nucleic acid products.

3. A method for simultaneously amplifying 5 or more loci in a nucleic acid solution comprising:

providing in single solutions contained in a plurality of reaction chambers located in a biochip, samples having at least five target nucleic acid loci to be amplified, with at least five different primer pairs, each primer pair hybridizing to one of at least five loci, said solution further comprising:
(i) one or more buffers;
(ii) one or more salts;
(iii) a nucleic acid polymerase; and
(iv) nucleotides; and
providing a TCE, comprising a means for heating and cooling, at least one thermosensor, a controller that receives signals from said at least one thermosensor and a power supply, said at least one thermosensor positioned and configured to measure the effective temperature of each of the single solutions in the reaction chambers of the biochip and to provide feedback to the TCE to heat or cool the solution to set or maintain the solution at a desired temperature;
simultaneously amplifying said plurality of loci by using the at least one thermosensor, the controller and the TCE to sequentially thermally cycle the temperature of the nucleic acid solution in each reaction chamber between a denaturing state, an annealing state, and an extension state for a predetermined number of cycles at heating and cooling rates of about 4-1 50° C./sec, and minimizing the transition times between the extension, denaturation, and annealing states to yield 5 or more amplified loci in each reaction chamber in 97 minutes or less.

4. The method of claim 1 or 3 wherein the biochip is plastic.

5. The method of claim 1 or 3, wherein the amplified loci are produced in less than 45 minutes.

6. The method of claim 3 further comprising, prior to the sequential thermal cycling,
heating the one or a plurality of reaction solutions to a first temperature suitable for hot-start activation of the nucleic acid polymerases; and
holding the one or a plurality of reaction solutions at the first temperature for a first period of time suitable for hot-start activation of the nucleic acid polymerases.

7. The method of claim 6, wherein the first period of time is less than 90 seconds.

8. The method of claim 6 wherein the first temperature is about 90 to about 99° C.

9. The method claim 5, wherein the nucleic acid polymerase has an extension rate of at least 100 bp/sec.

10. The method of claim 5, wherein each reaction chamber has a volume of less than 100 μL.

11. The method of claim 5, wherein each reaction chamber is separated from a thermal cycler by less than 200 μm.

12. The method of claim 5, wherein each nucleic acid solution comprises about 1 to about 1000 copies of a target nucleic acid.

13. The method claim 5, wherein the nucleic acid polymerase is SpeedSTAR, PHUSION, Hot MasterTaq™, PHUSION Mpx, PyroStart, KOD, Z-Taq, or CS3AC/LA.

14. The method of claim 5, wherein analysis of each of the amplified nucleic acid products satisfies forensic interpretation guidelines.

15. The method of claim 5, wherein the denaturing state is about 95° C. for about 4 seconds.

16. The method of claim 5, wherein the annealing state is about 59° C. for about 15 seconds.

17. The method of claim 5, wherein the extension state is about 72° C. for about 7 seconds.

18. The method claim 5, wherein the final state is about 70° C. for about 90 seconds.

19. The method claim 5, wherein the one or a plurality of reaction solutions are cooled from the denaturing state to the annealing state at a first cooling rate of about 10 to about 50° C./sec.

20. The method of claim 5, wherein the one or a plurality of reaction solutions are heated from the annealing state to the extension state at a first heating rate of about 10 to about 50° C./sec.

21. The method claim 5, wherein the one or a plurality of reaction solutions are heated from the extension state to the denaturing state at a second heating rate of about 10 to about 50° C./sec.

22. The method of claim 5, wherein the one or a plurality of amplified nucleic acid products are obtained in about 10 to about 90 minutes.

23. The method of claim 5, wherein each reaction solution comprises about 0.005 to about 10 ng of a target nucleic acid.

24. The method of claim 5, wherein the target nucleic acid comprises a human nucleic acid, microbial nucleic acid, or viral nucleic acid.

25. The method of claim 5, wherein 10 to 250 loci are simultaneously amplified.

26. The method of claim 5, wherein the loci comprise amelogenin, D8S 1179, D21S11, D7S820, CFS1PO, D3S1358, TH01, D13S317, D16S539, D2S1338, D19S433, vWA, TPDX, D18S51, D5S818, FGA, or a plurality thereof.

27. The method of claim 5, wherein the predetermined number of cycles is between about 10 and about 50 cycles.

28. The method of claim 5, wherein one or a plurality of thin-wall reaction tubes comprise the one or a plurality of reaction chambers.

* * * * *